US008585717B2

(12) United States Patent
Sorrentino et al.

(10) Patent No.: US 8,585,717 B2
(45) Date of Patent: *Nov. 19, 2013

(54) SINGLE STROKE ENDOSCOPIC SURGICAL CLIP APPLIER

(75) Inventors: Gregory Sorrentino, Wallingford, CT (US); Kenneth H. Whitfield, New Haven, CT (US)

(73) Assignee: Covidien LP, Mansfield, MA (US)

( * ) Notice: Subject to any disclaimer, the term of this patent is extended or adjusted under 35 U.S.C. 154(b) by 739 days.

This patent is subject to a terminal disclaimer.

(21) Appl. No.: 12/539,069

(22) Filed: Aug. 11, 2009

(65) Prior Publication Data

US 2010/0057102 A1    Mar. 4, 2010

Related U.S. Application Data

(60) Provisional application No. 61/092,796, filed on Aug. 29, 2008.

(51) Int. Cl.
    *A61B 17/10* (2006.01)
(52) U.S. Cl.
    USPC .......................................................... 606/143
(58) Field of Classification Search
    USPC .................. 606/142, 143, 213, 219, 157; 227/175.1, 176.1
    See application file for complete search history.

(56) References Cited

U.S. PATENT DOCUMENTS

| 3,120,230 | A | 2/1964 | Skold |
| 3,638,847 | A | 2/1972 | Noiles et al. |
| 4,242,902 | A | 1/1981 | Green |
| 4,296,751 | A | 10/1981 | Blake, III et al. |
| 4,372,316 | A | 2/1983 | Blake, III et al. |
| 4,408,603 | A | 10/1983 | Blake, III et al. |
| 4,480,640 | A | 11/1984 | Becht |
| 4,480,641 | A | 11/1984 | Failla et al. |
| 4,487,204 | A | 12/1984 | Hrouda |

(Continued)

FOREIGN PATENT DOCUMENTS

| EP | 0 085 931 A2 | 8/1983 |
| EP | 0 324 166 A2 | 7/1989 |

(Continued)

OTHER PUBLICATIONS

European Search Report corresponding to EP 09252053; date of mailing is Dec. 1, 2009; date of completion of Search is Nov. 24, 2009 (3 Pages).

(Continued)

*Primary Examiner* — Corrine M McDermott
*Assistant Examiner* — Christina Lauer

(57) ABSTRACT

An apparatus for application of surgical clips to body tissue is provided and includes a handle assembly; a shaft assembly including a housing extending distally from the handle assembly and defining a longitudinal axis; a plurality of surgical clips disposed within the shaft assembly; a jaw mounted adjacent a distal end portion of the shaft assembly, the jaw being movable between an open spaced-apart condition and a closed approximated condition; and a pusher bar reciprocally disposed within the housing of the shaft assembly and being detachably connectable to the housing of the shaft assembly, the pusher bar being configured to load a distal-most surgical clip into the jaws during distal movement and remain connected to the housing of the shaft assembly and in a distally advanced position during an approximation of the jaws.

22 Claims, 45 Drawing Sheets

(56) References Cited

U.S. PATENT DOCUMENTS

| | | | |
|---|---|---|---|
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A * | 6/1987 | Klieman et al. .............. 606/143 |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |

(56) References Cited

U.S. PATENT DOCUMENTS

| | | |
|---|---|---|
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuildin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |

(56) References Cited

U.S. PATENT DOCUMENTS

| | | |
|---|---|---|
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,320,692 B1 | 1/2008 | Bender et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,344,544 B2 | 3/2008 | Bender et al. |
| 7,357,805 B2 | 4/2008 | Masuda et al. |
| 7,357,806 B2 | 4/2008 | Rivera et al. |
| 7,407,074 B2 | 8/2008 | Ortiz et al. |
| 7,419,495 B2 | 9/2008 | Menn et al. |
| 7,431,724 B2 | 10/2008 | Manetakis et al. |
| 7,458,978 B1 | 12/2008 | Bender et al. |
| 7,473,258 B2 | 1/2009 | Clauson et al. |
| 7,485,124 B2 | 2/2009 | Kuhns et al. |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |

(56) References Cited

U.S. PATENT DOCUMENTS

| | | |
|---|---|---|
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079912 A1 | 4/2006 | Whitfield et al. |
| 2006/0079913 A1 | 4/2006 | Whitfield |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1* | 4/2007 | Whitfield et al. ............ 606/142 |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045978 A1 | 2/2008 | Kuhns et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0114377 A1 | 5/2008 | Shibata et al. |
| 2008/0114378 A1 | 5/2008 | Matsushita |
| 2008/0125796 A1 | 5/2008 | Graham |
| 2008/0132915 A1 | 6/2008 | Buckman et al. |
| 2008/0140089 A1 | 6/2008 | Kogiso et al. |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0188872 A1 | 8/2008 | Duff |
| 2008/0207995 A1 | 8/2008 | Kortenbach et al. |
| 2008/0208217 A1 | 8/2008 | Adams |
| 2008/0228199 A1 | 9/2008 | Cropper et al. |
| 2008/0228202 A1 | 9/2008 | Cropper et al. |
| 2008/0243143 A1 | 10/2008 | Kuhns et al. |
| 2008/0243145 A1 | 10/2008 | Whitfield et al. |
| 2008/0255589 A1 | 10/2008 | Blakeney et al. |
| 2008/0294178 A1 | 11/2008 | Kortenbach et al. |
| 2008/0306491 A1 | 12/2008 | Cohen et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312666 A1 | 12/2008 | Ellingwood et al. |
| 2008/0312670 A1 | 12/2008 | Lutze et al. |
| 2008/0319456 A1 | 12/2008 | Hart |
| 2010/0274262 A1 | 10/2010 | Schulz et al. |

FOREIGN PATENT DOCUMENTS

| | | |
|---|---|---|
| EP | 0 392 750 A1 | 10/1990 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0732078 A | 9/1996 |
| EP | 0 755 655 A | 1/1997 |
| EP | 0 769 274 A1 | 4/1997 |
| EP | 0 769 275 | 4/1997 |
| EP | 0 834 286 | 4/1998 |
| EP | 1 317 906 | 6/2003 |
| EP | 1 609 427 A1 | 12/2005 |
| EP | 1 712 191 A2 | 10/2006 |
| EP | 1 813 199 A1 | 8/2007 |
| EP | 1 908 423 A | 4/2008 |
| EP | 1 908 423 A2 | 4/2008 |
| EP | 1 913 881 A1 | 4/2008 |
| EP | 2 229 895 A1 | 9/2010 |
| JP | 2003 033361 A | 2/2003 |

(56) References Cited

FOREIGN PATENT DOCUMENTS

| WO | WO 2005/091457 | 9/2005 |
|---|---|---|
| WO | WO 2006/042076 | 4/2006 |
| WO | WO 2006/042084 | 4/2006 |
| WO | WO 2006/042110 | 4/2006 |
| WO | WO 2008/118928 A2 | 10/2008 |
| WO | WO 2008/127968 A | 10/2008 |

OTHER PUBLICATIONS

European Search Report corresponding to EP 09252051; date of mailing is Jan. 28, 2010; date of completion of Search is Dec. 21, 2009 (3 Pages).
European Search Report corresponding to EP 09252050; date of mailing is Jan. 21, 2010; date of completion of Search is Dec. 23, 2009 (3 Pages).
European Search Report corresponding to EP 09252054; date of mailing is Jan. 22, 2010; date of completion of Search is Jan. 7, 2010 (3 Pages).
Extended European Search Report corresponding to EP 10252079.8, date of mailing is Mar. 17, 2011; date of completion of Search is Mar. 8, 2011 (3 Pages).
Extended European Search Report corresponding to EP 09252056.8, date of mailing is Feb. 5, 2010; date of completion of Search is Jan. 8, 2010 (3 Pages).
Extended European Search Report corresponding to EP 10250497.4, date of mailing is May 12, 2010; date of completion of Search is May 4, 2010 (6 Pages).
European Search Report corresponding to EP 05810218.7, mailed on May 20, 2011; completed on Apr. 18, 2011; 3 pages.
European Search Report corresponding to EP 05807612.6, mailed on May 20, 2011; completed on May 2, 2011; 3 pages.
Extended European Search Report corresponding to EP 10251737.2, mailed on May 20, 2011; completed on May 9, 2011; 4 pages.
The extended European Search Report corresponding to European Application No. EP 11250214.1, completed May 25, 2011; mailed Jun. 1, 2011; (3 Pages).
International Search Report for application EP 07 25 3905 dated Feb. 7, 2008.
International Search Report from European Application No. EP 07 25 3807 mailed Aug. 1, 2008.
International Search Report from PCT Application No. PCT/US08/58185 dated Sep. 9, 2008.
International Search Report from PCT Application No. PCT/US08/59859 dated Sep. 18, 2008.
The extended European Search Report from Application No. EP 07 25 3807 Nov. 26, 2008.
European Search Report corresponding to European Application No. EP 05 80 2686.5, completed Jan. 9, 2012; mailed Jan. 18, 2012; (3 Pages).
The extended European Search Report corresponding to European Application No. EP 12 15 1313.9, completed Mar. 20, 2012 and mailed Apr. 12, 2012; (5 Pages).
The extended European Search Report corresponding to European Application No. EP 12 16 1291.5, completed Apr. 24, 2012 and mailed May 4, 2012; (5 Pages).
The extended European Search Report corresponding to European Application No. EP 12 16 2288.0, completed Jun. 4, 2012 and mailed Jul. 7, 2012; (6 Pages).
The extended European Search Report corresponding to European Application No. EP 12 16 5891.8, completed Jun. 12, 2012 and mailed Jun. 20, 2012; (6 Pages).
European Search Report (5 pages) for EP12164955—mailing date Sep. 4, 2012.
European Search Report for corresponding EP 09252049 date of mailing is Jan. 12, 2010 (3 pages).

\* cited by examiner

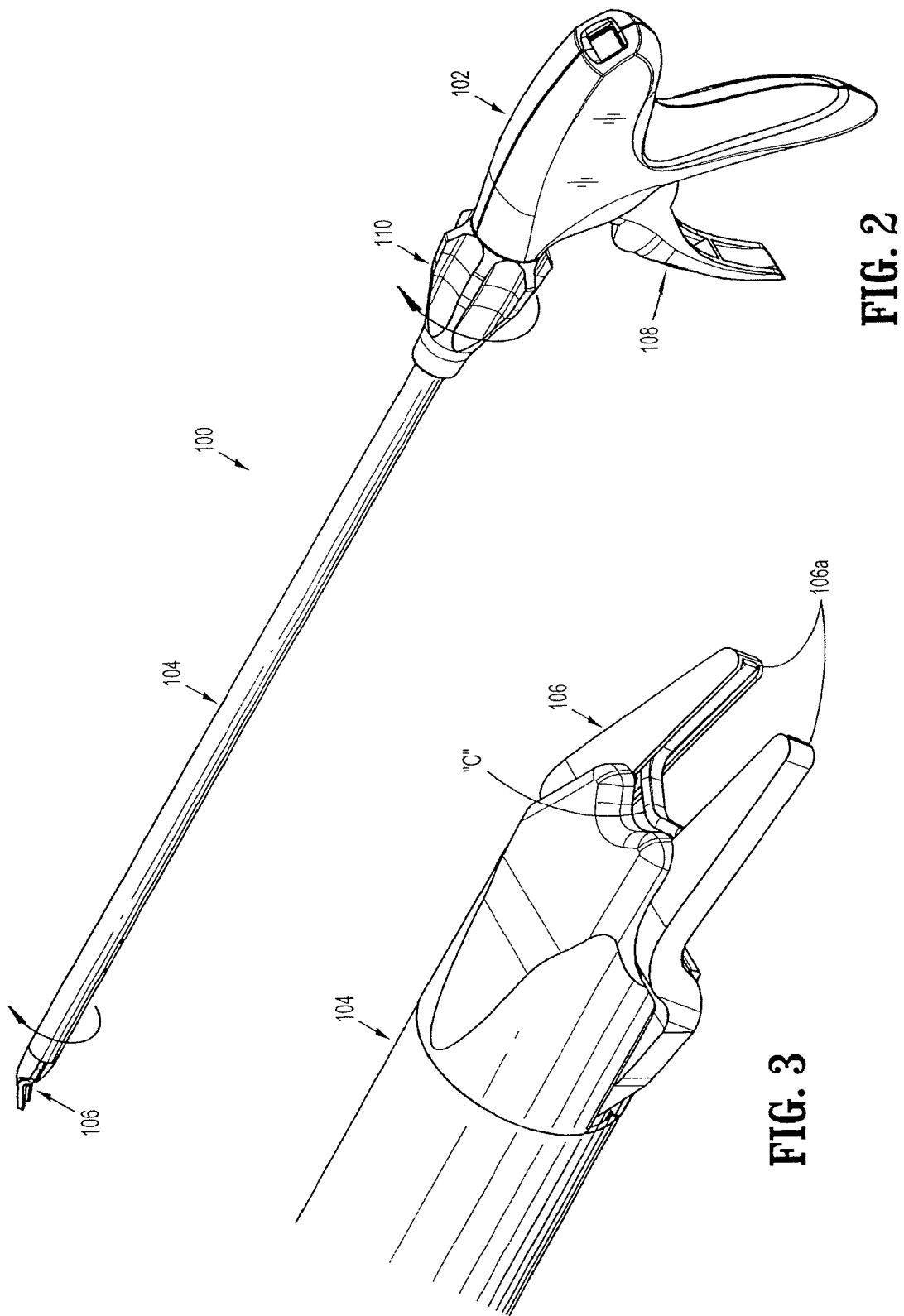

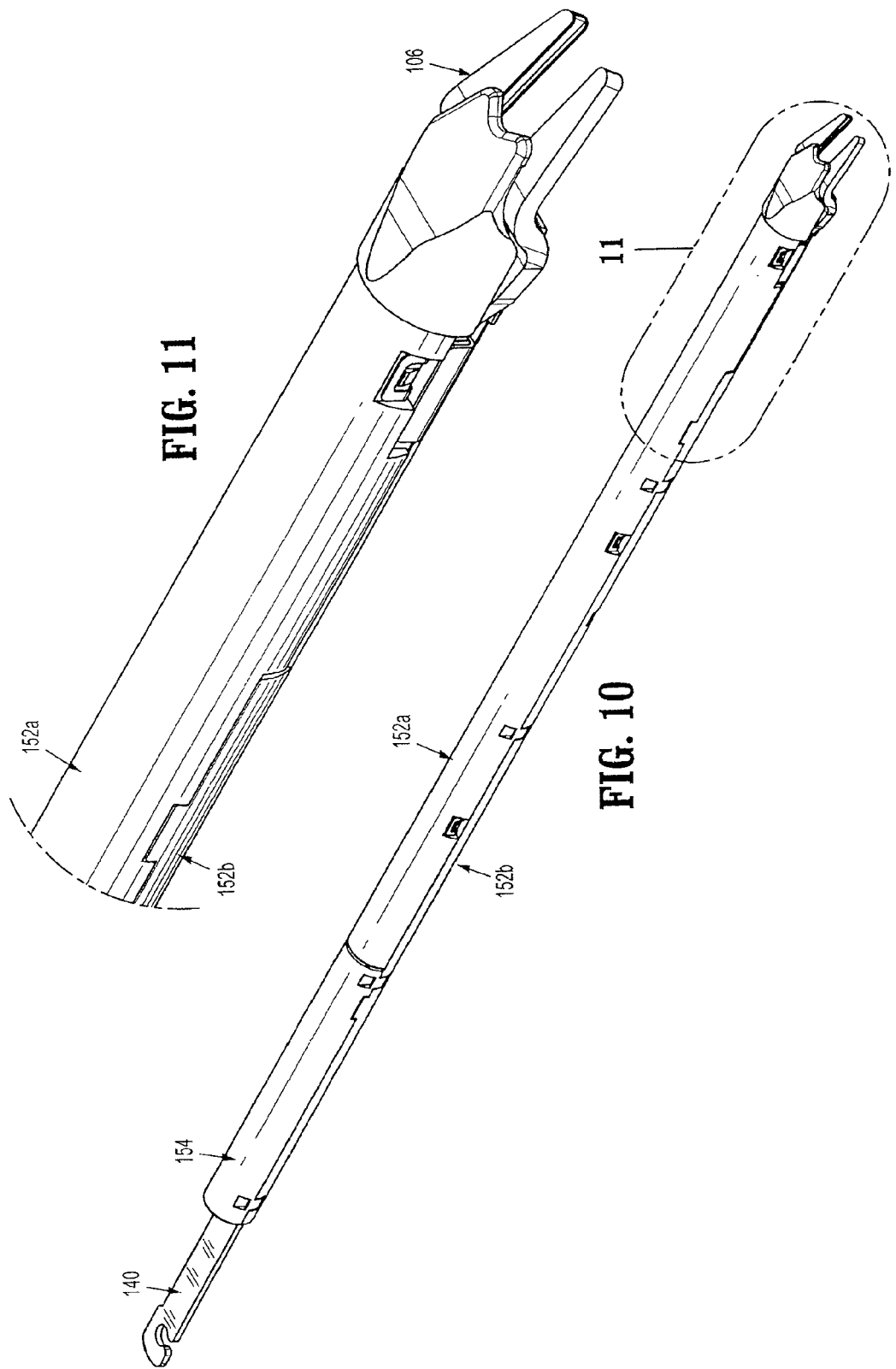

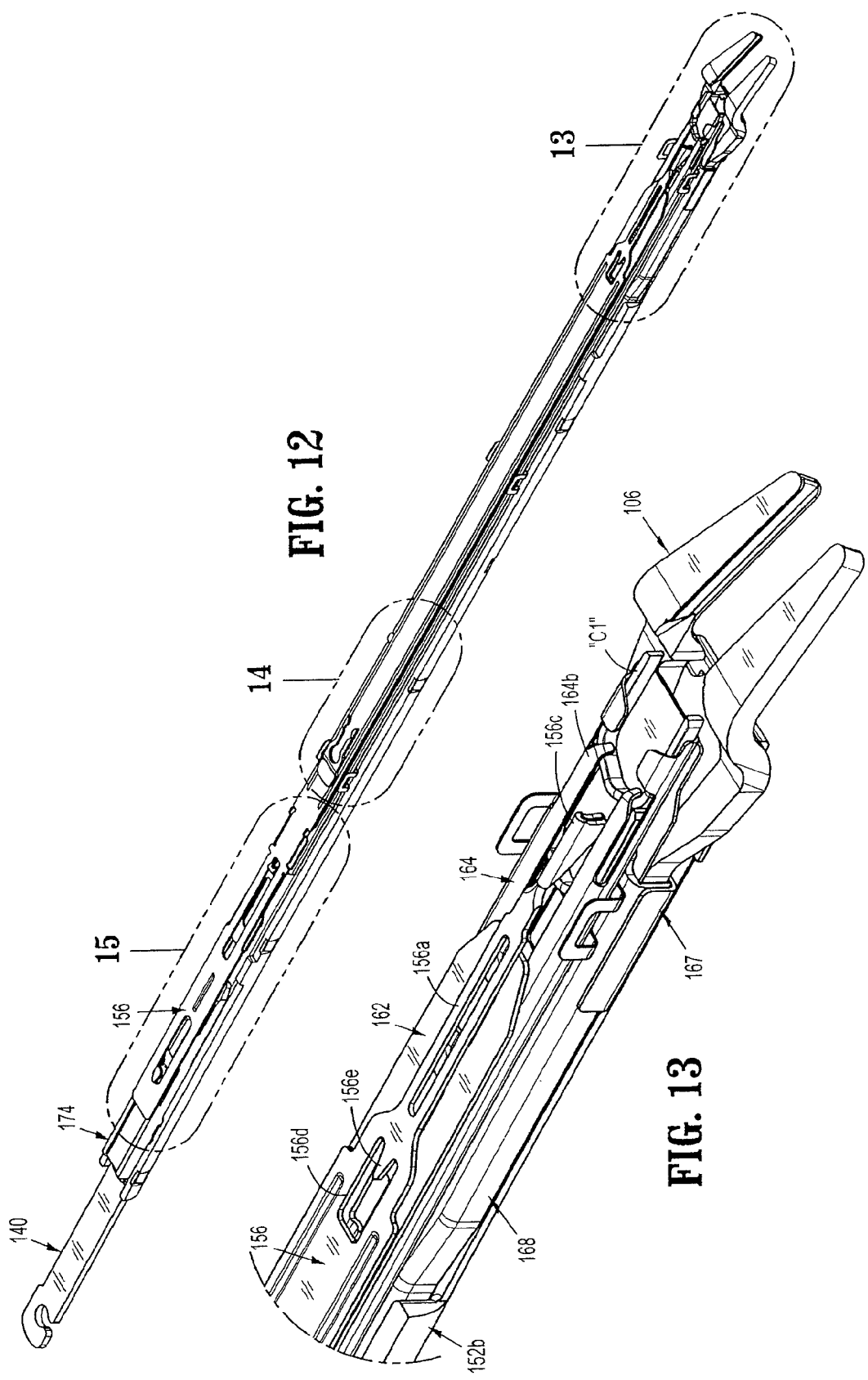

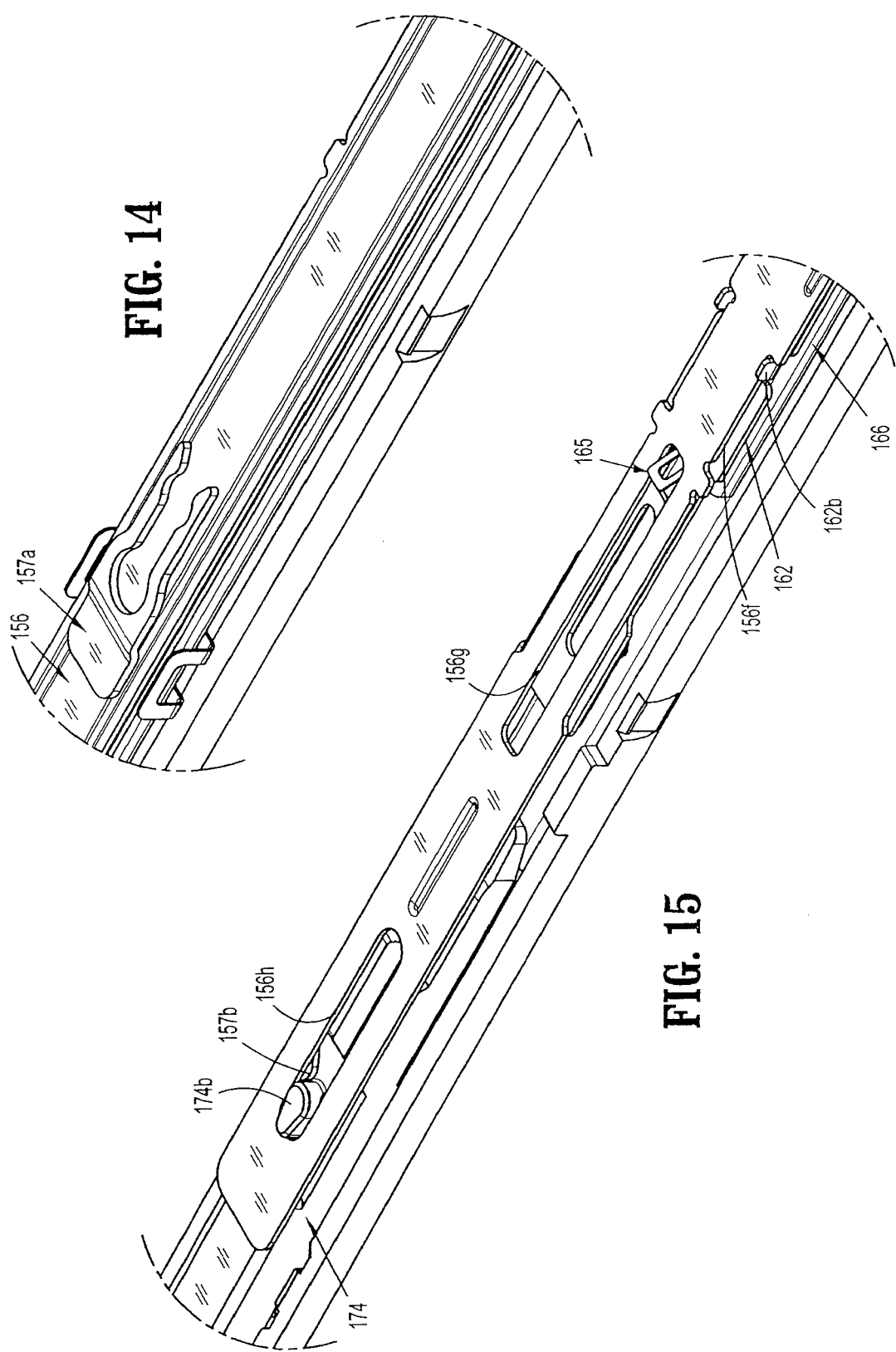

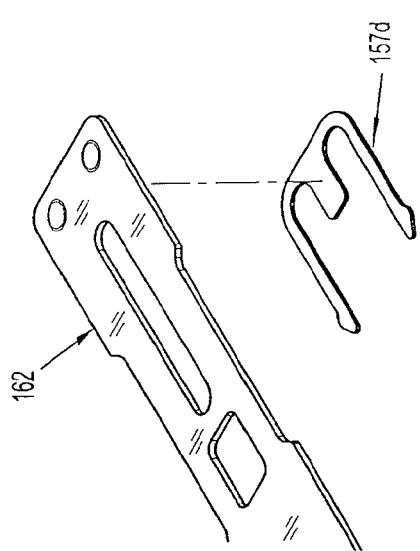
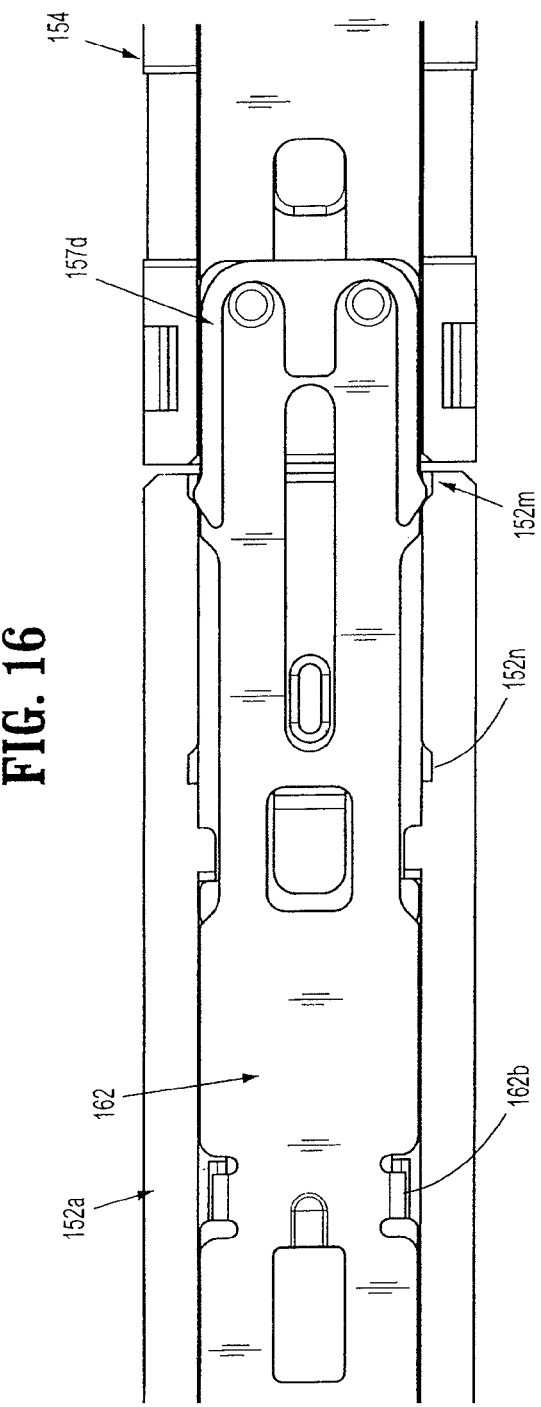
FIG. 16
FIG. 17

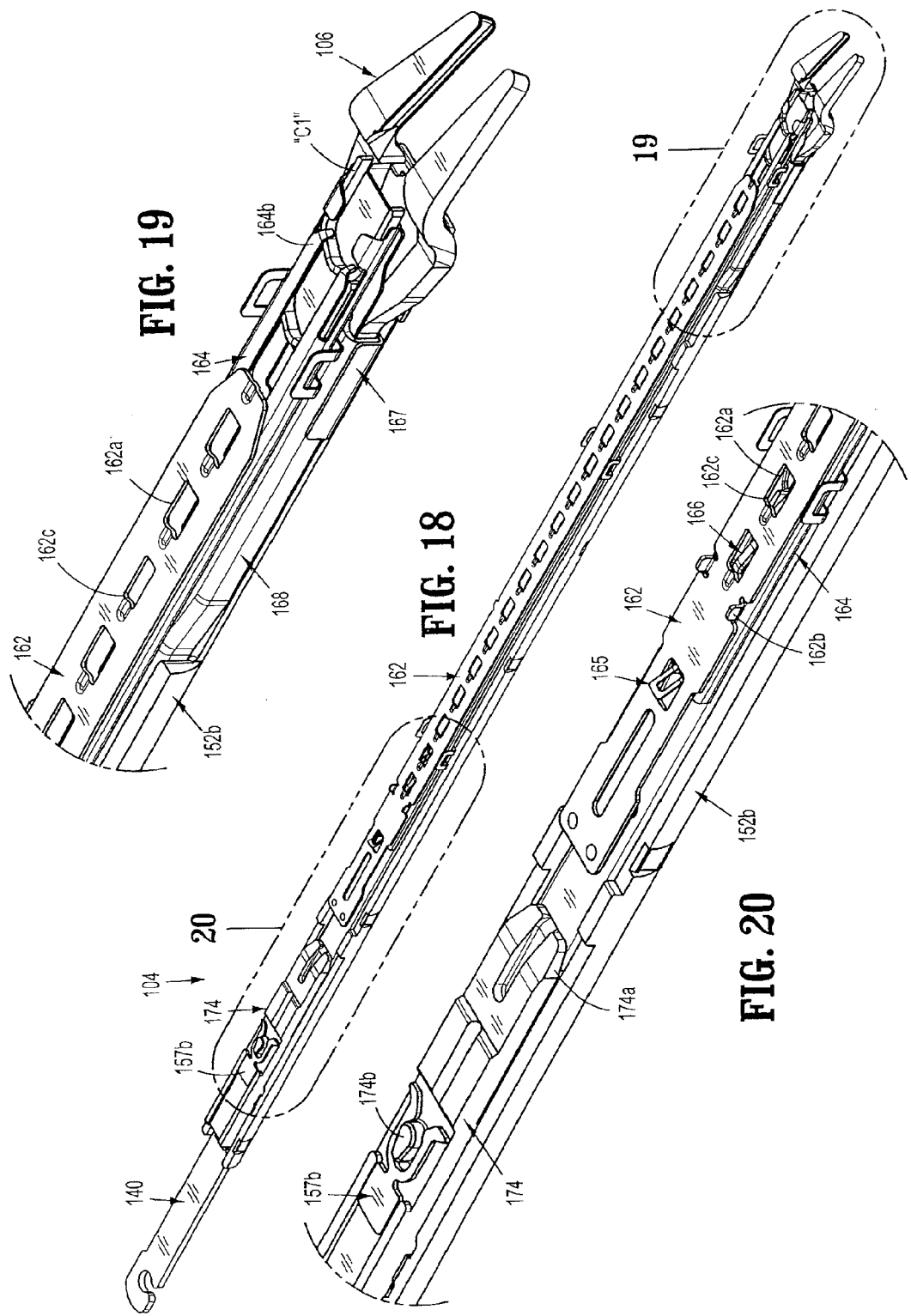

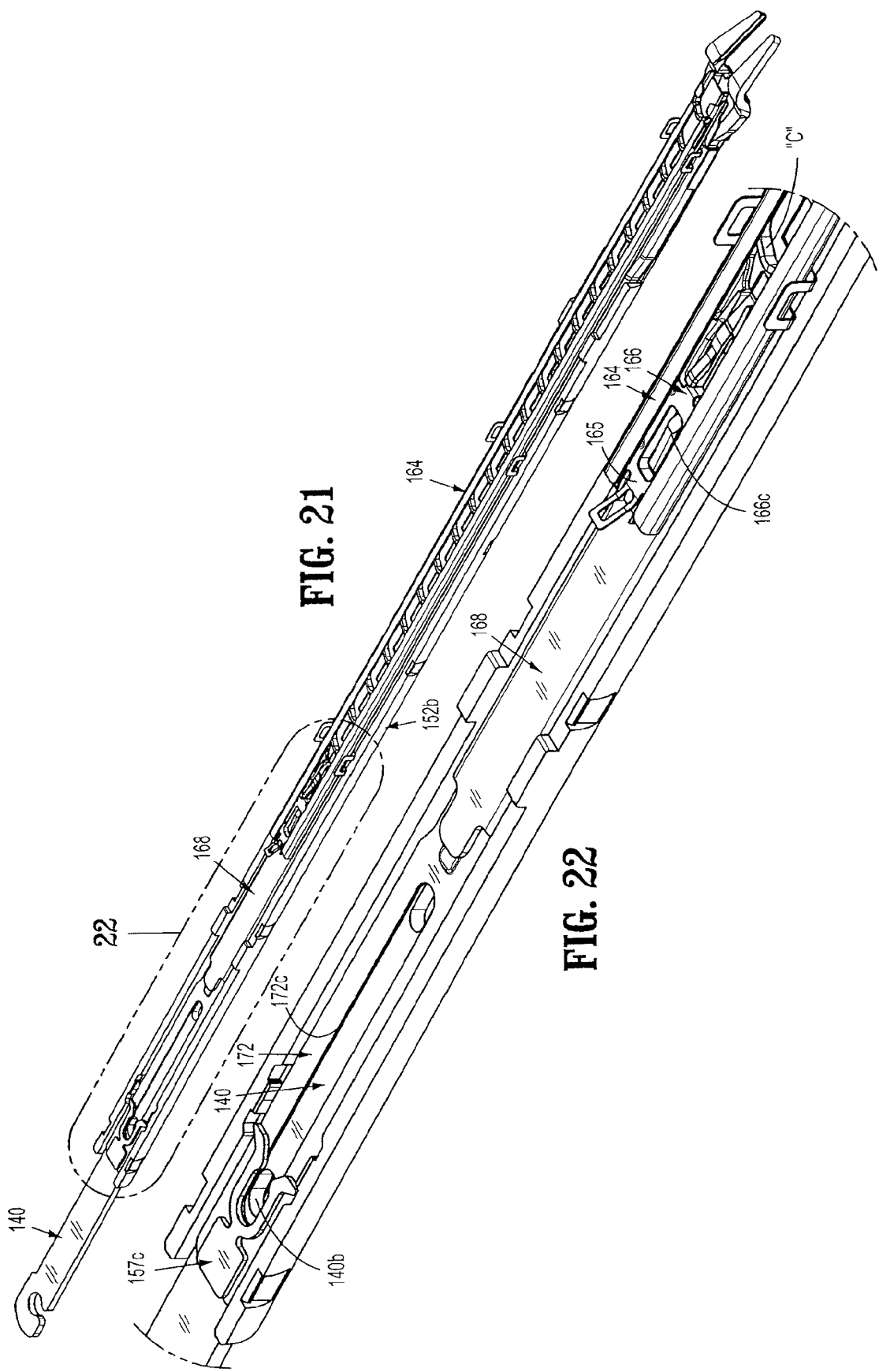

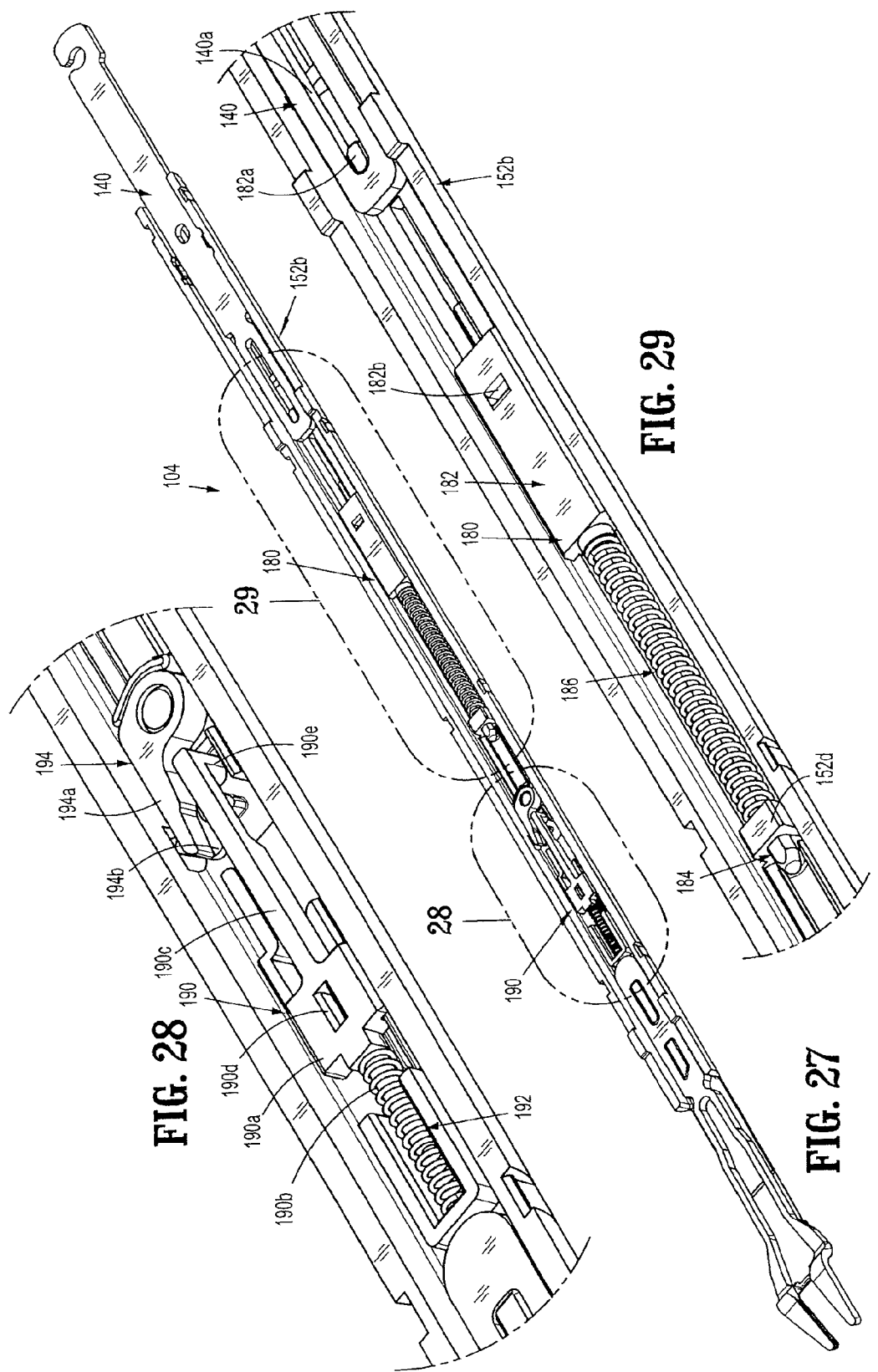

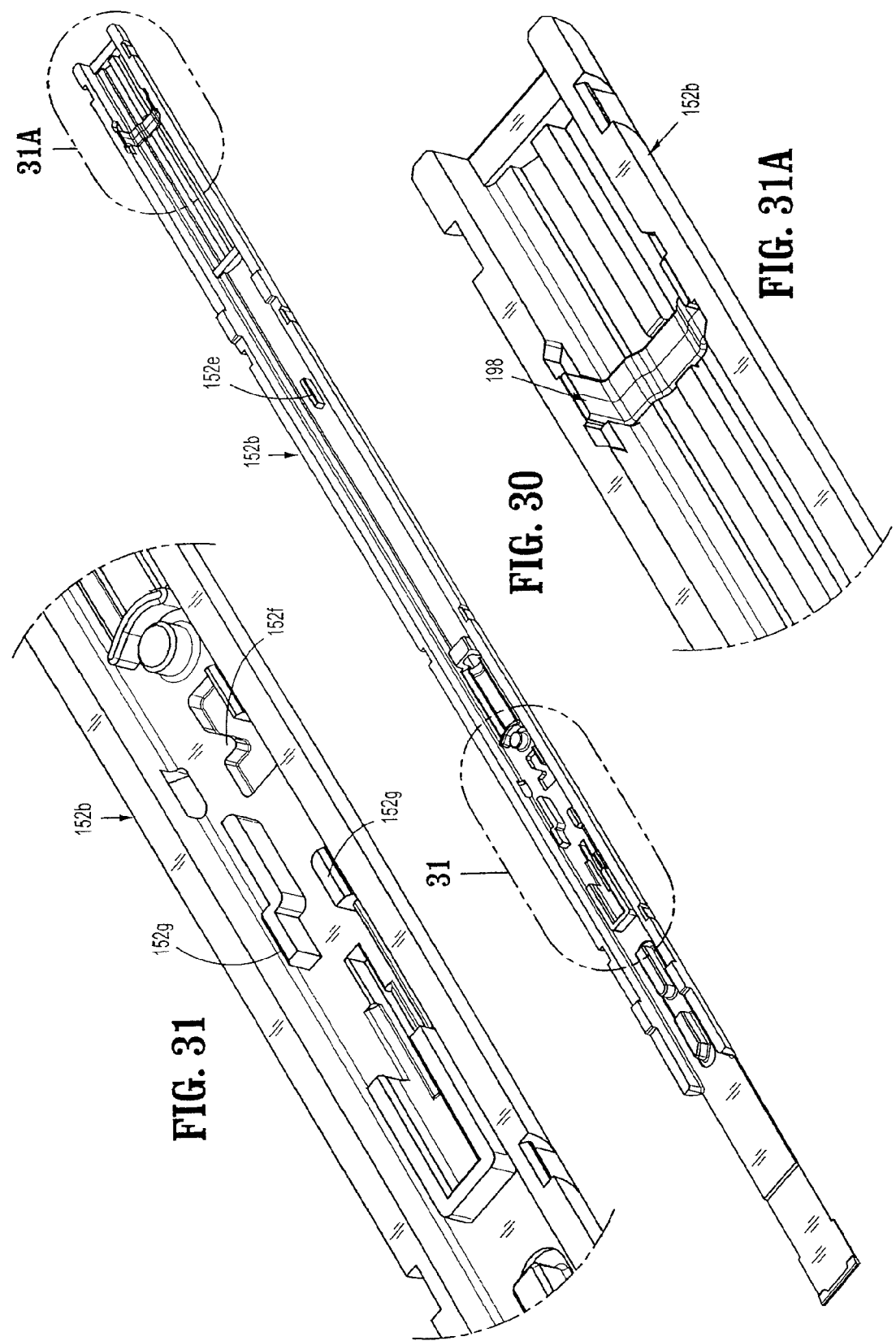

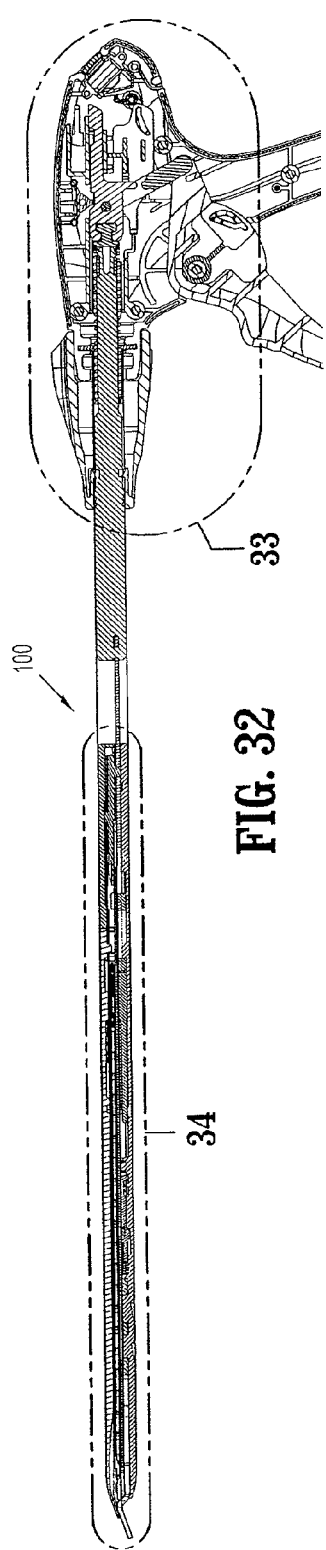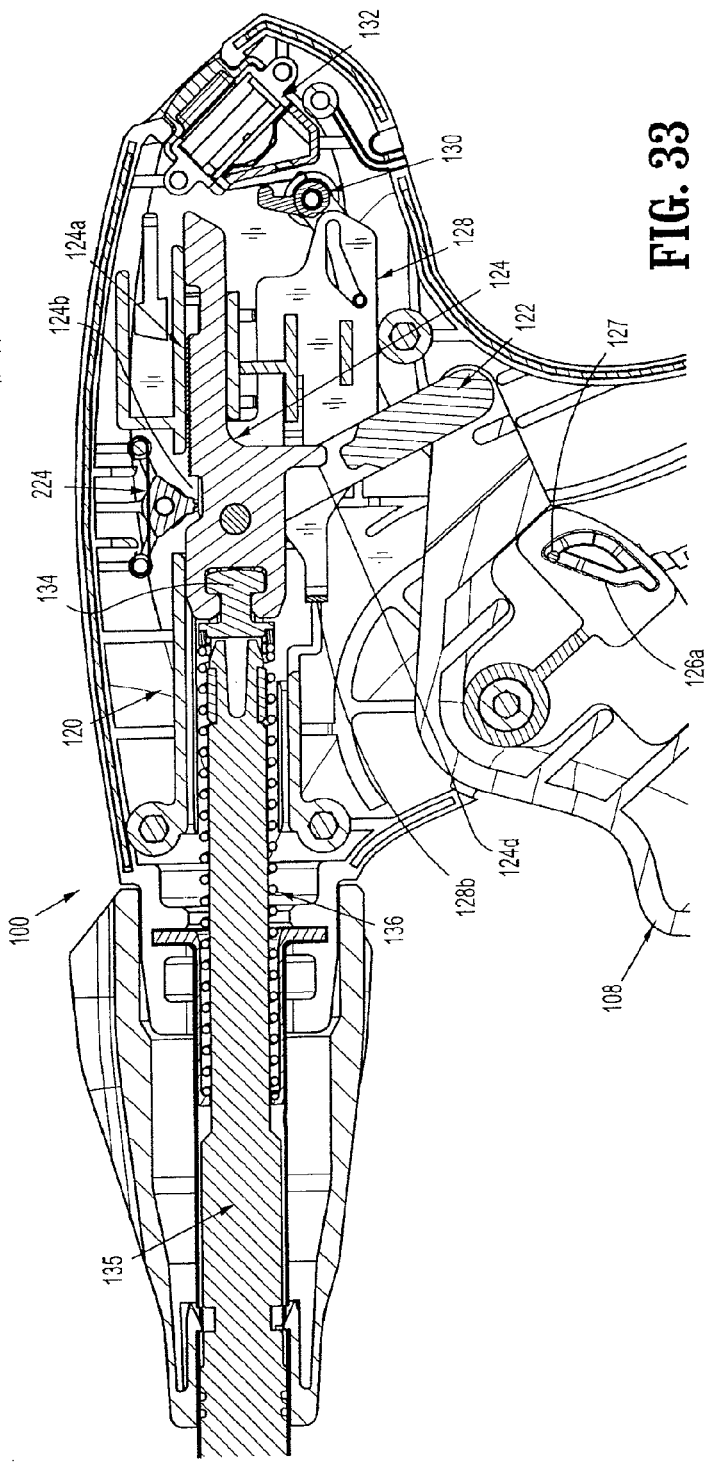

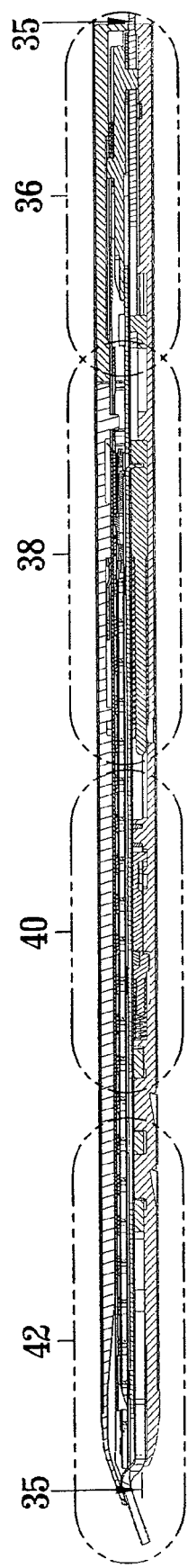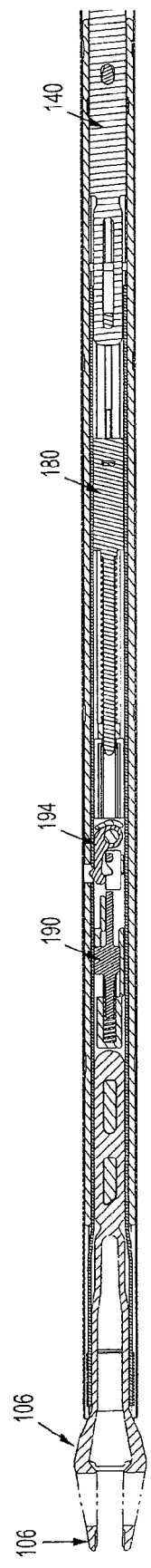
FIG. 34
FIG. 35

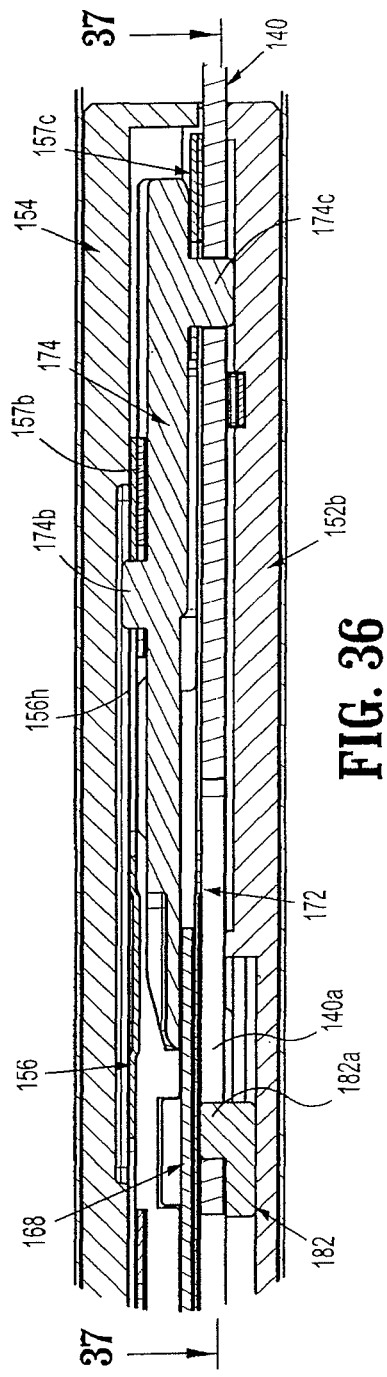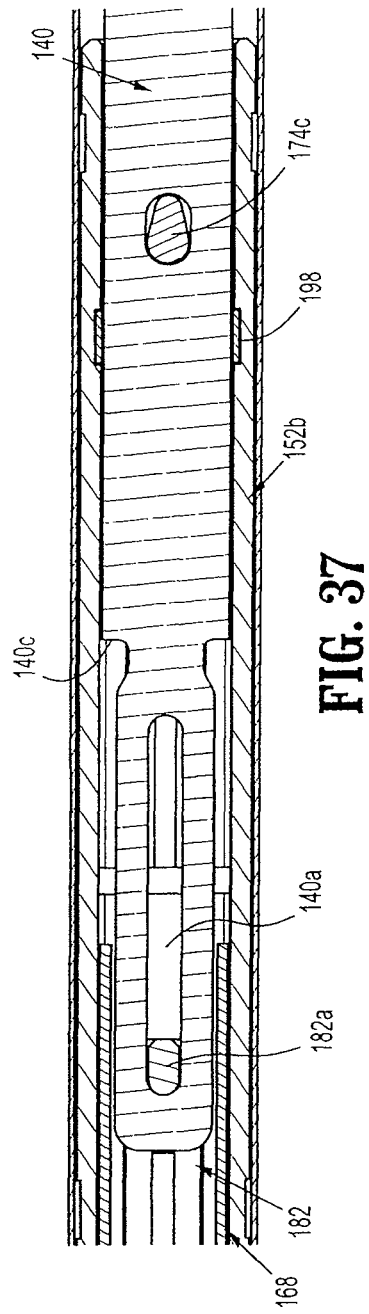

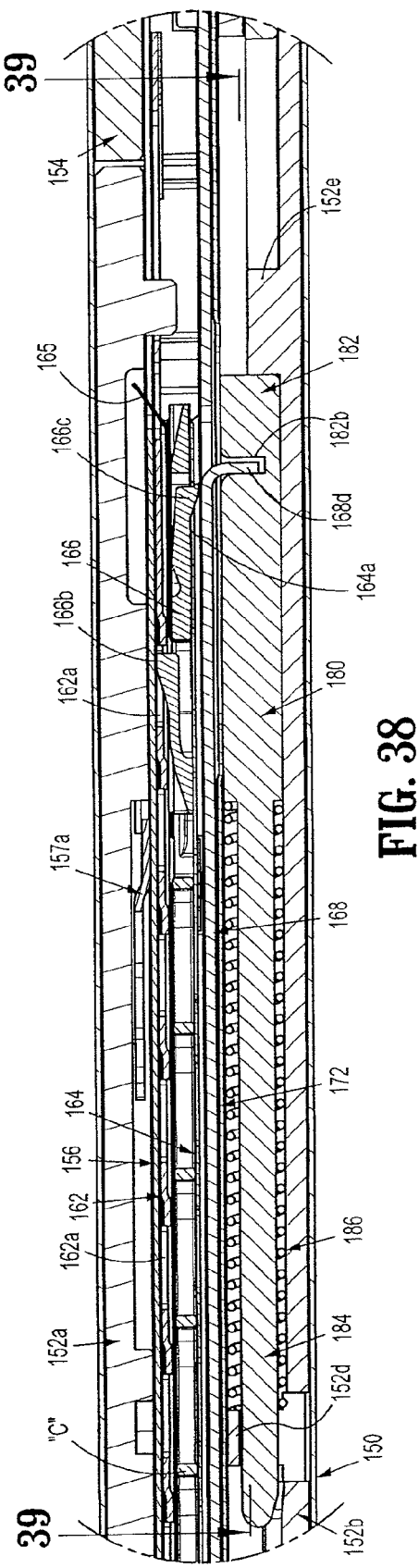
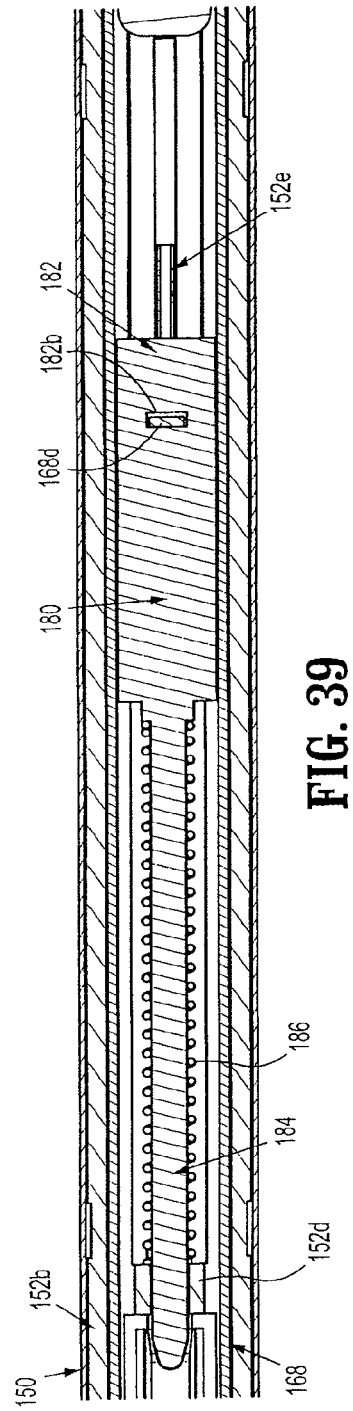
FIG. 38
FIG. 39

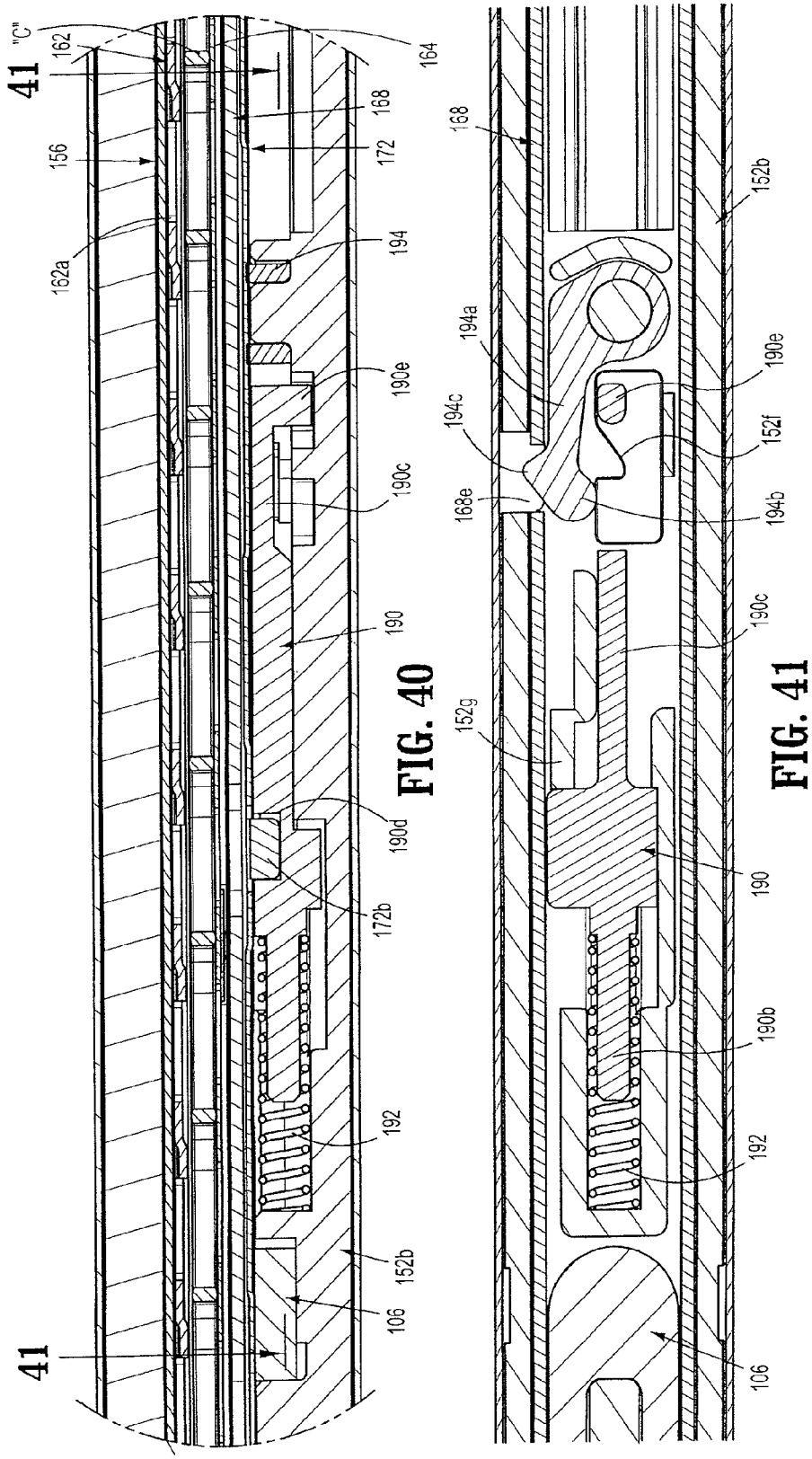

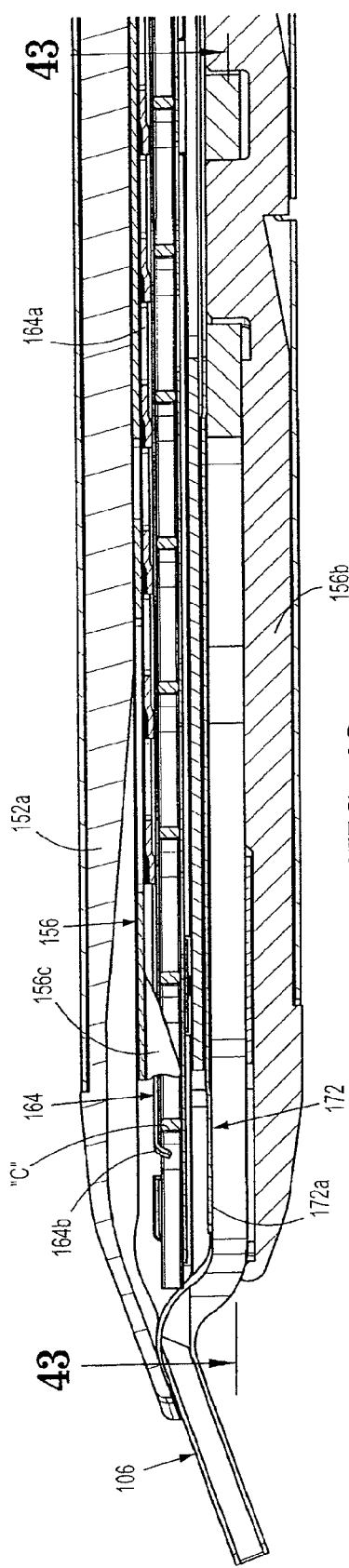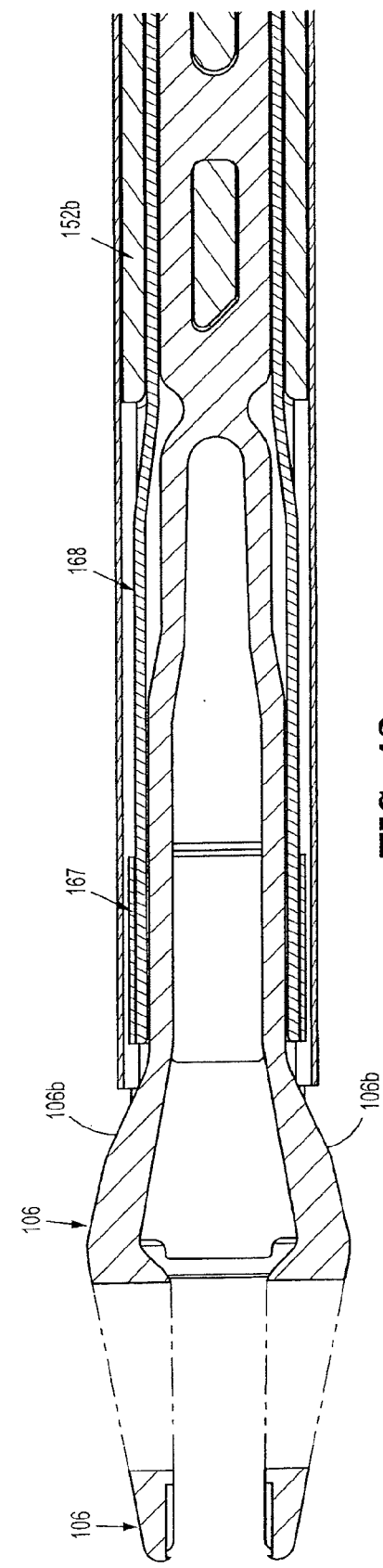

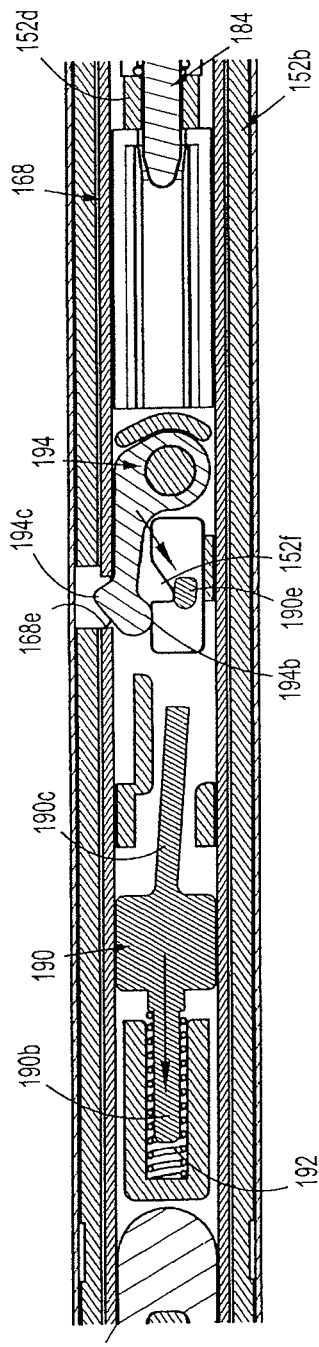
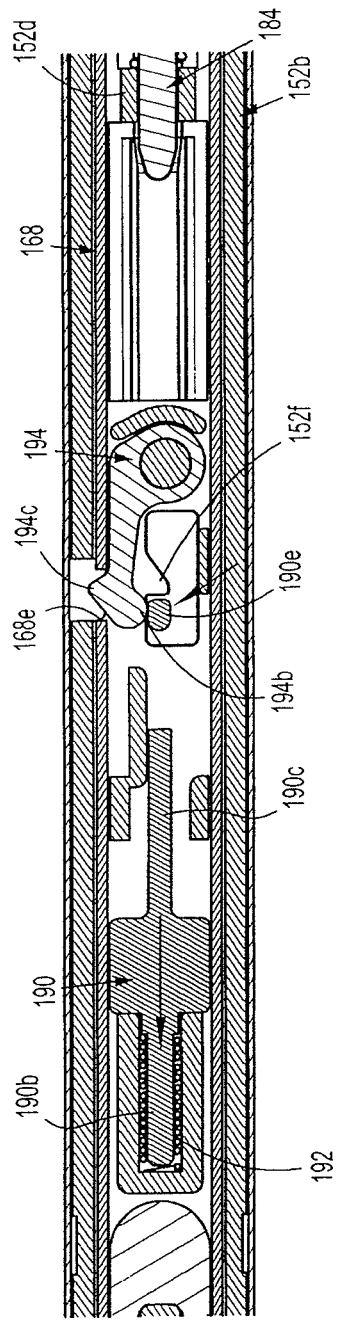
FIG. 48
FIG. 49

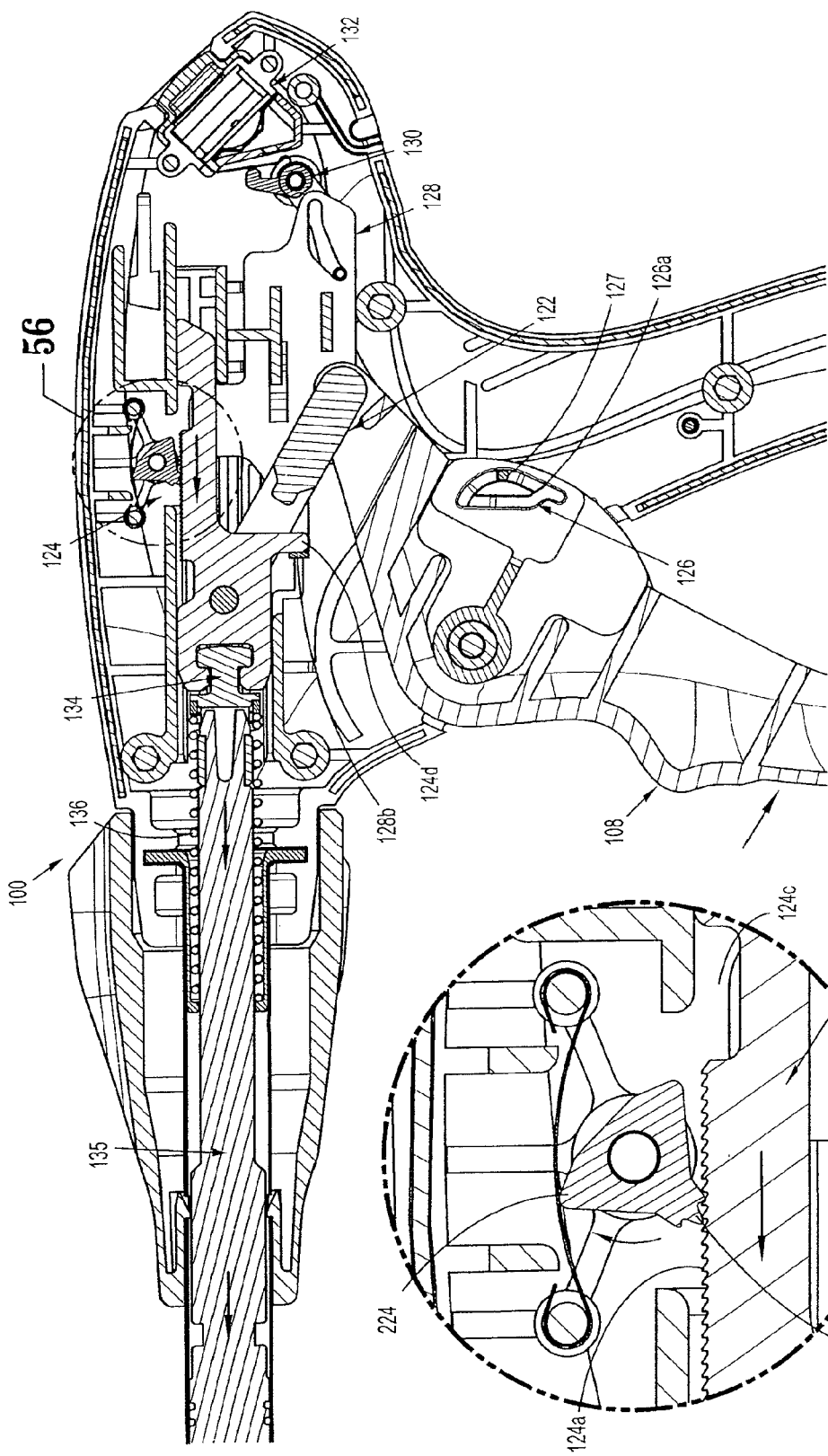

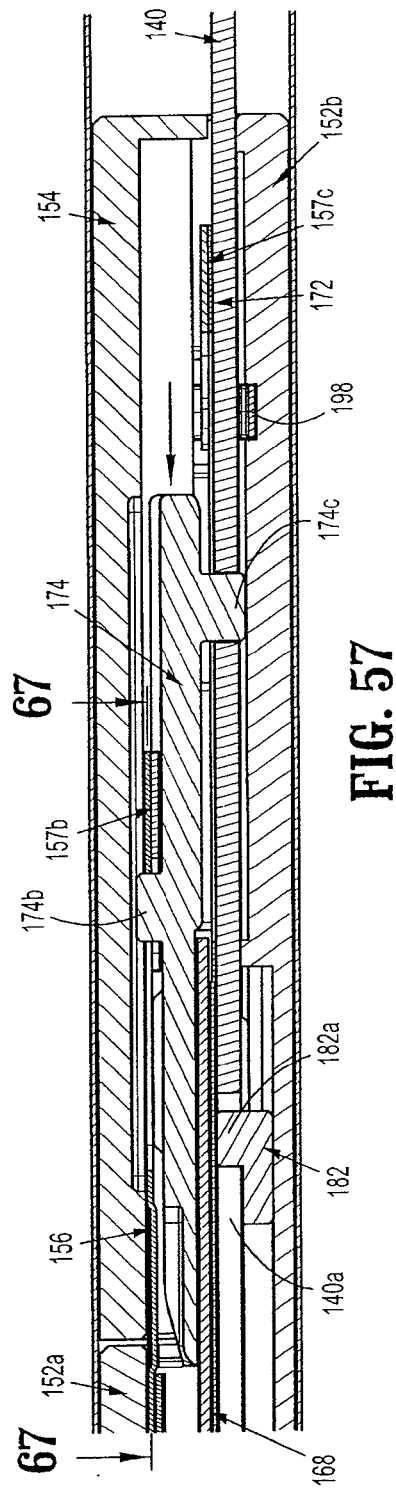
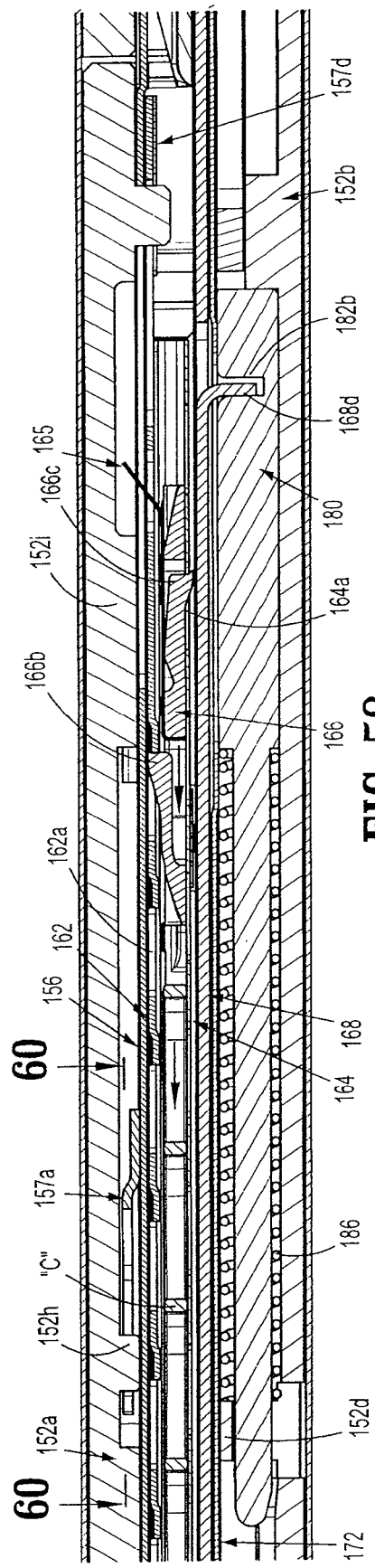
FIG. 57
FIG. 58

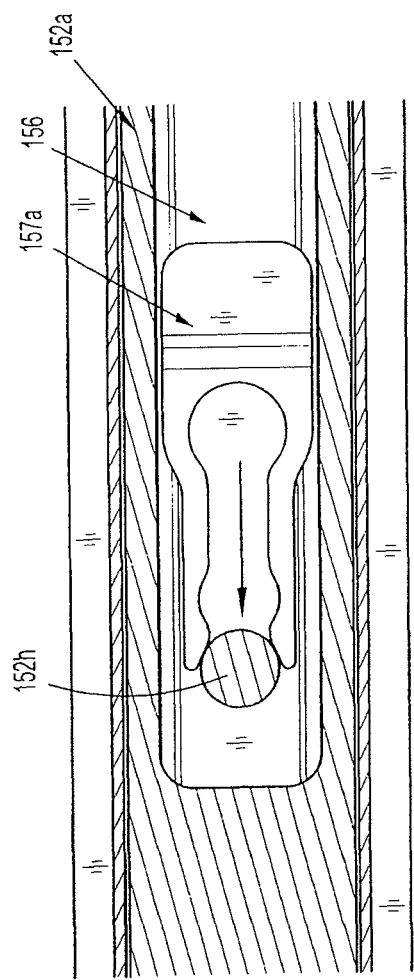
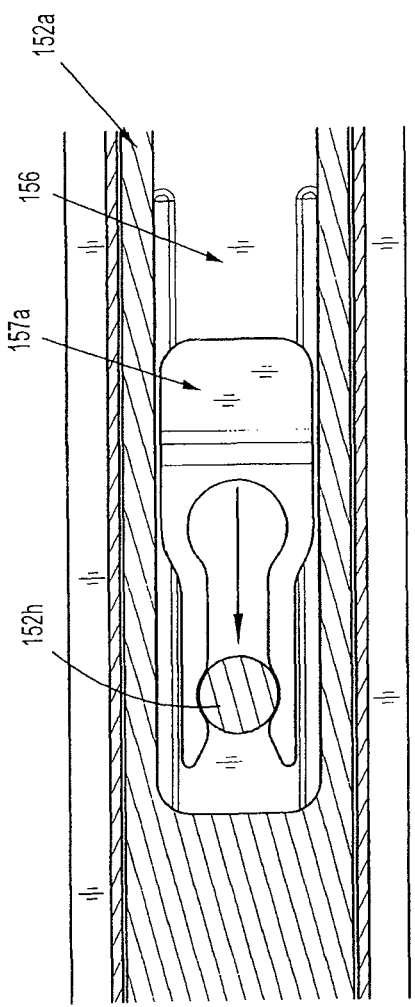
FIG. 59
FIG. 60

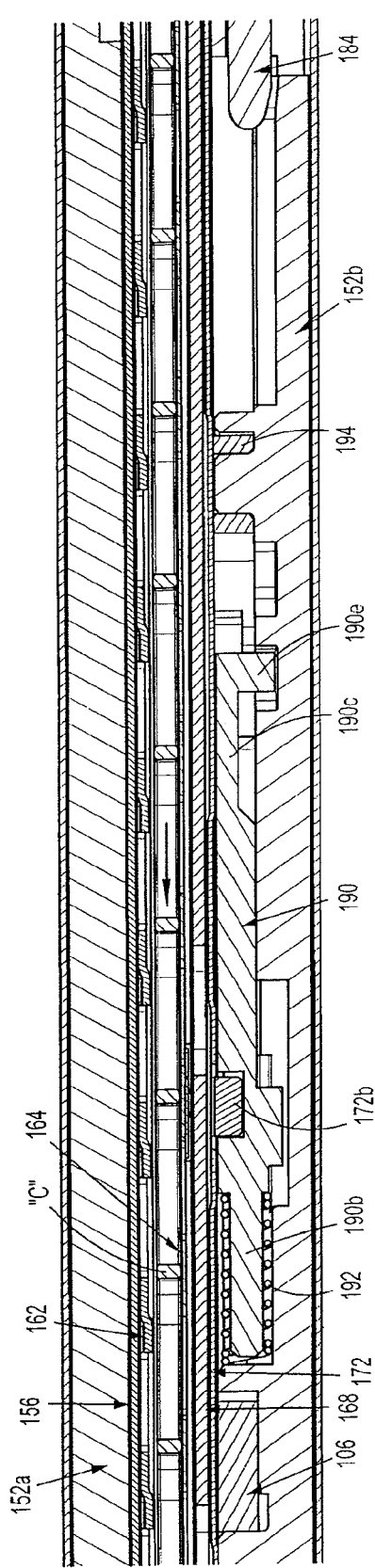
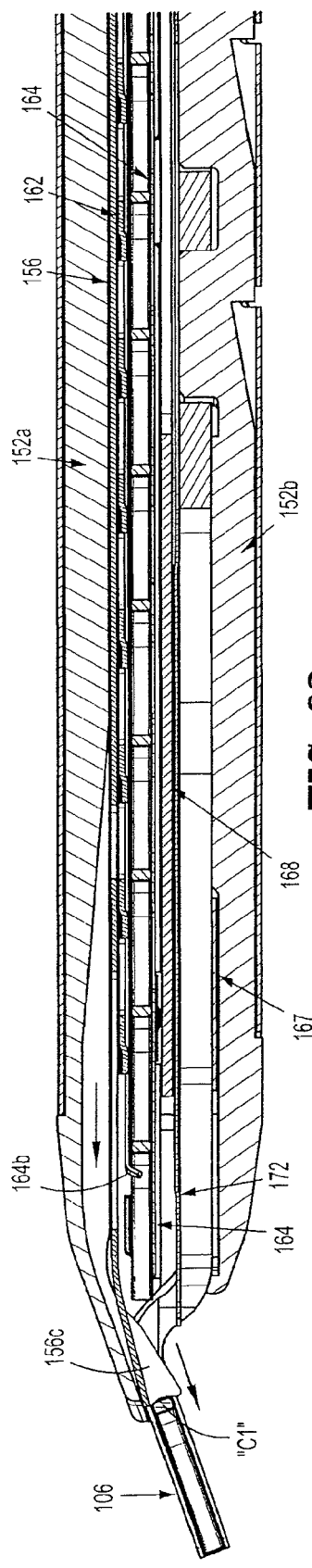
FIG. 61
FIG. 62

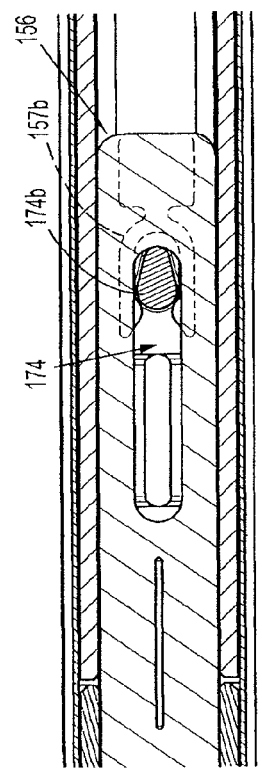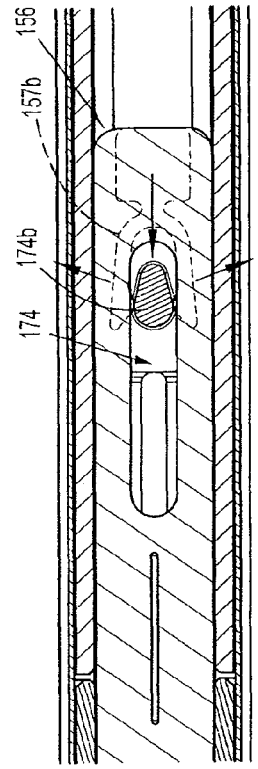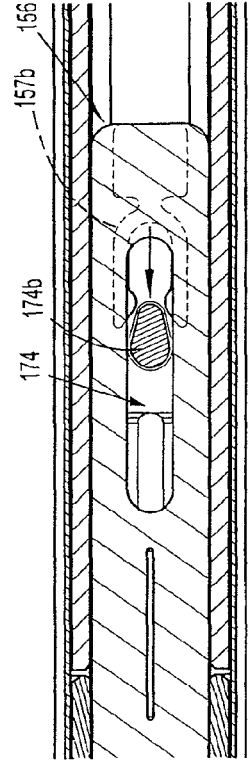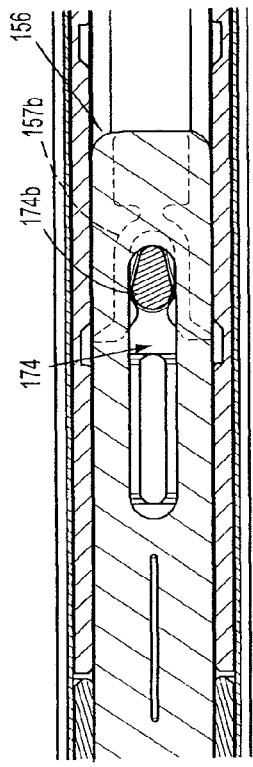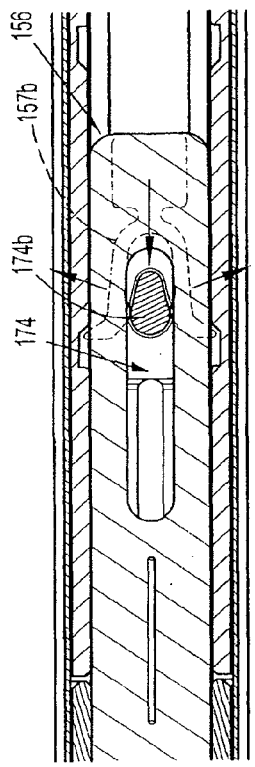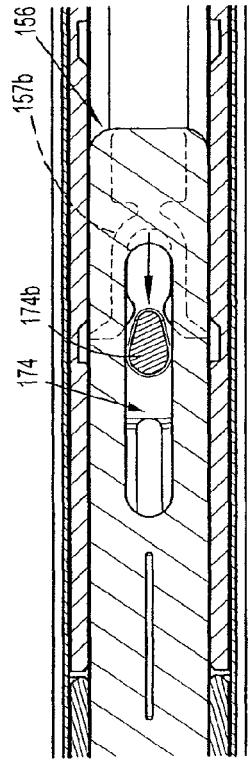

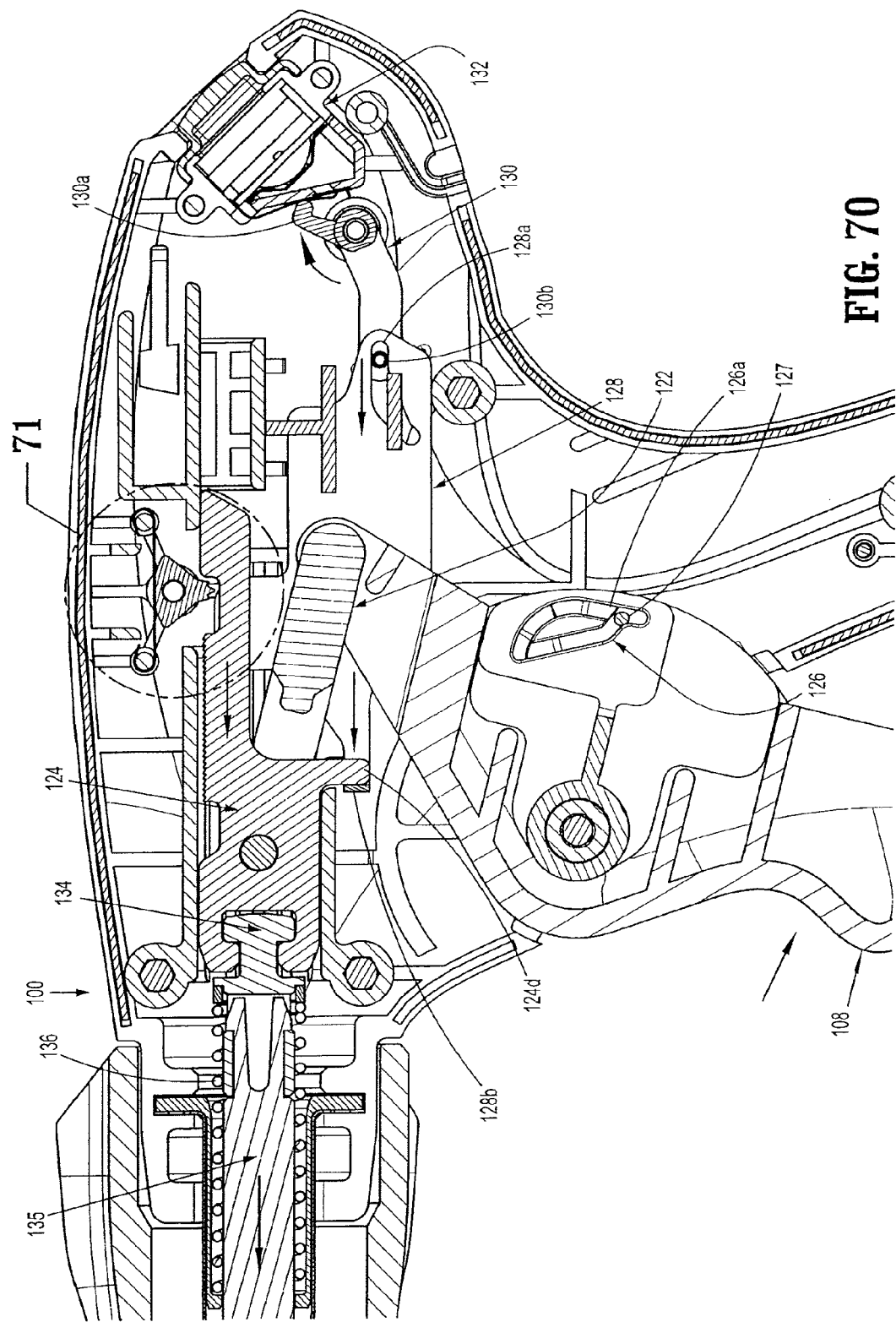

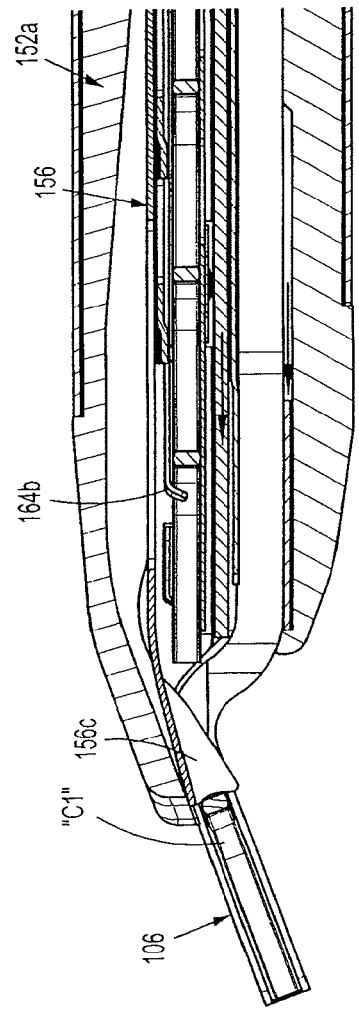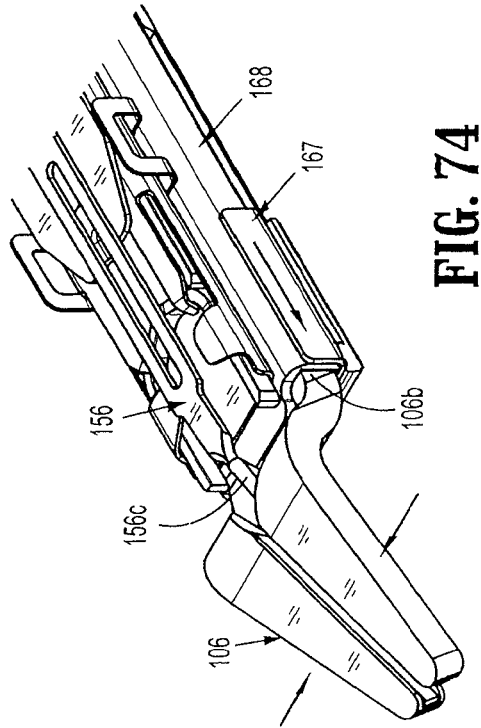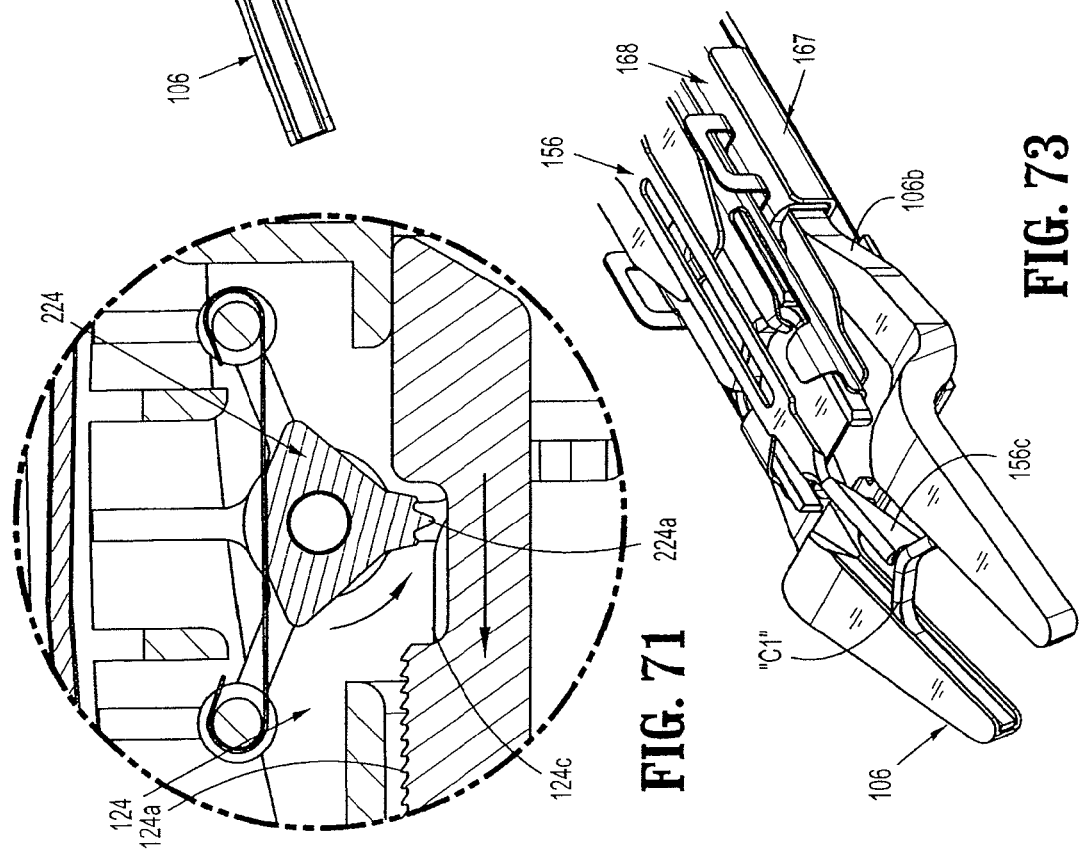

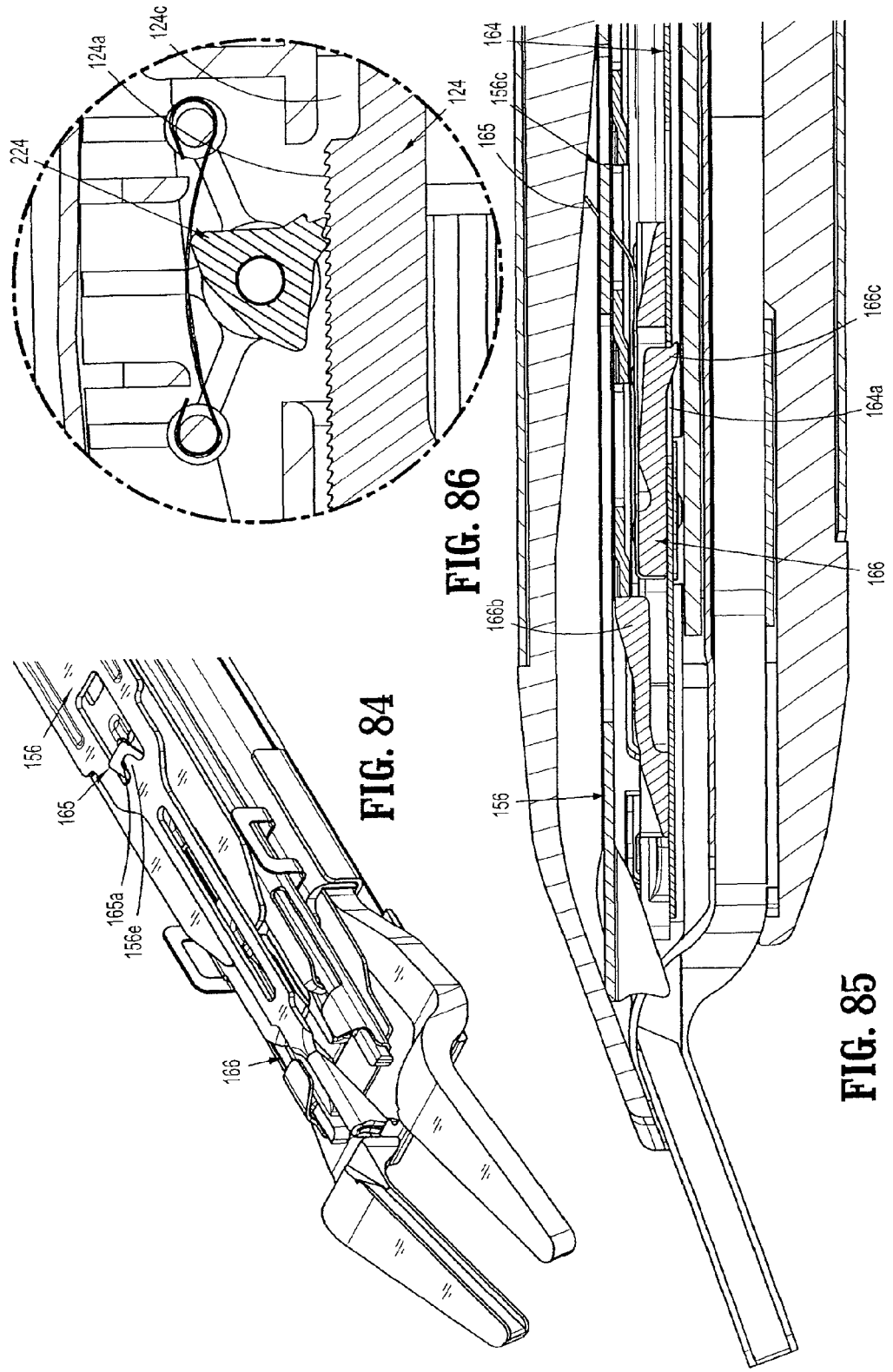

SINGLE STROKE ENDOSCOPIC SURGICAL CLIP APPLIER

CROSS REFERENCE TO RELATED APPLICATION

The present application claims the benefit of and priority to U.S. Provisional Application Ser. No. 61/092,796 filed on Aug. 29, 2008, the entire contents of which are incorporated herein by reference.

BACKGROUND

1. Technical Field

The present disclosure relates to surgical clip appliers and, more particularly, to a novel endoscopic surgical clip applier.

2. Background of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such single clip appliers are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 to Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity. One significant design goal is that the surgical clip be loaded between the jaws without any compression of the clip from the loading procedure. Such bending or torque of the clip during loading often has a number of unintended consequences. Such compression during loading may alter slightly the alignment of the clip between the jaws. This will cause the surgeon to remove the clip from between the jaws for discarding the clip. Additionally such preloading compression may slight compress parts of the clip and change a geometry of the clip. This will cause the surgeon to remove the compressed clip from between the jaws for discarding the clip.

Endoscopic or laparoscopic procedures are often performed remotely from the incision. Consequently, application of clips may be complicated by a reduced field of view or reduced tactile feedback for the user at the proximal end of the device. It is therefore desirable to improve the operation of the instrument by providing indication to the user of a firing of an individual clip, the depletion of the clips contained in the loading unit, or any other surgical event. It is also desirable to provide a surgical clip applier that promotes a successful loading of the clip and that wedges the jaws of the surgical clip applier open, then loads the clip between the jaws in order to prevent any damage or excessive compression of the clip and prevents compression of the jaws on the clip before firing.

SUMMARY

The present disclosure relates to novel endoscopic surgical clip appliers.

According to an aspect of the present disclosure, an apparatus for application of surgical clips to body tissue is provided. The apparatus includes a handle assembly; a shaft assembly extending distally from the handle assembly and defining a longitudinal axis; a plurality of surgical clips disposed within the shaft assembly; a jaw mounted adjacent a distal end portion of the shaft assembly, the jaw being movable between an open spaced-apart condition and a closed approximated condition; and a pusher bar reciprocally disposed within the shaft assembly, the pusher bar being configured to load a distal-most surgical clip into the jaws while the jaws are in the open condition and remain in contact with the loaded surgical clip during an approximation of the jaws.

The pusher bar may include a pusher formed at a distal end thereof. The pusher may have a narrow profile for contacting the loaded surgical staple at a single location. The pusher may define a plane that is oriented substantially orthogonal to a plane of the loaded surgical staple.

The apparatus may further include a connector plate reciprocally disposed within the shaft assembly. The connector plate may be selectively connected to the pusher bar. In use, during an initial distal movement of the connector plate, the pusher bar may be distally advanced and during a further distal movement of the connector plate the connector plate may be disconnected from the pusher bar.

The pusher bar may include a first spring clip supported thereon for selectively engaging a feature of the shaft assembly when the pusher bar is in an advanced position for selectively maintaining the pusher bar in the advanced position. The pusher bar may further include a second spring clip supported thereon for selectively engaging a first feature of the connector plate. The first feature of the connector plate may selectively disengage from the second spring clip following the initial distal movement of the connector plate.

The apparatus may further include an advancer plate reciprocally disposed within the shaft assembly. The advancer plate may include at least one fin selectively engageable by a shoulder of the pusher bar. In use, the shoulder of the pusher bar may engage the at least one fin of the advancer plate during a distal and a proximal movement of the pusher bar to effectuate one of a distal and proximal movement of the advancer plate.

The apparatus may further include a clip follower slidably supported in the shaft assembly for urging the plurality of surgical clips in a distal direction. The clip follower may include a first tab projecting from a first surface thereof and a second tab projecting from a second surface thereof. In use, the first tab of the clip follower may engage the advancer plate as the advancer plate is moved distally such that the clip follower is moved distally to advance the plurality of surgical clips, and wherein the second tab of the clip follower may engage a stationary feature as the advancer plate is moved proximally such that the clip follower remains stationary.

The apparatus may further include a clip carrier disposed in the shaft assembly, wherein the clip carrier is configured to retain the plurality of surgical clips and the clip follower, and wherein the second tab of the clip follower may engage features formed in the clip carrier.

The clip follower may be incrementally advanced through the shaft assembly. The clip follower may include a catch extending from a surface thereof, wherein the catch may engage the pusher bar following firing of a last surgical clip and may prevent movement of the pusher bar in a proximal direction.

The apparatus may further include a ratchet assembly disposed in the handle assembly. The ratchet assembly may be prevented from re-setting when the pusher bar does not return to a proximal position.

The apparatus may further include a counter supported in the housing assembly. The counter may provide an indication when a surgical clip has been fired.

The apparatus may further include an indicator supported in the housing assembly. The indicator may provide at least one of an audible and a tactile indication when at least one of a surgical clip is loaded into the jaws, a surgical clip is fired and the apparatus is re-set.

The apparatus may further include a wedge plate reciprocally disposed within the shaft assembly. The wedge plate may be movable between a position where a distal end thereof is disposed in the jaws and a position where the distal end thereof is free from said jaws. The wedge plate may further include a third spring clip supported thereon for selectively engaging a second feature of the connector plate, wherein the second feature of the connector plate selectively disengages from the third spring clip following an initial distal movement of the connector plate.

The apparatus may further include a drive bar actuatable by the handle assembly and connected to the connector plate for effecting movement of the connector plate. The apparatus may further include a drive channel reciprocally disposed within the shaft assembly, wherein the drive bar selectively engages the drive channel to effect translation of the drive channel. A distal end of the drive channel may engage a surface of the jaws upon distal advancement thereof to effectuate approximation of the jaws.

The drive channel may actuate a wedge lock release upon distal advancement thereof to cause proximal movement of the wedge plate to withdraw the distal end of the wedge plate from the jaws and permit the drive channel to approximate the jaws.

The shaft assembly may be rotatable, about the longitudinal axis, with respect to the handle assembly. The shaft assembly may include a guard supported therein, wherein the guard may prevent the third spring clip from splaying outwardly as the third spring clip translates thereacross.

The wedge plate and/or the drive channel may be biased to a proximal position.

According to another aspect of the present disclosure, an apparatus for application of surgical clips to body tissue is provided. The apparatus includes a handle assembly; a shaft assembly extending distally from the handle assembly and defining a longitudinal axis; a plurality of surgical clips disposed within the shaft assembly; a jaw mounted adjacent a distal end portion of the shaft assembly, the jaw being movable between an open spaced-apart condition and a closed approximated condition; and a clip follower slidably supported in the shaft assembly for urging the plurality of surgical clips in a distal direction. The clip follower includes a first tab projecting from a first surface thereof and a second tab projecting from a second surface thereof. The first tab of the clip follower engages the advancer plate as the advancer plate is moved distally such that the clip follower is moved distally to advance the plurality of surgical clips, and the second tab of the clip follower engages a stationary feature as the advancer plate is moved proximally such that the clip follower remains stationary.

The apparatus may further include an advancer plate reciprocally disposed within the shaft assembly. The advancer plate may define a plurality of windows formed along a length thereof. In use, the first tab of the clip follower may selectively engage a window of the plurality of windows as the advancer plate reciprocates.

The apparatus may further include a pusher bar reciprocally disposed within the shaft assembly. The pusher bar may be configured to load a distal-most surgical clip into the jaws while the jaws are in the open condition and remain in contact with the loaded surgical clip during an approximation of the jaws.

The advancer plate may include at least one fin selectively engageable by a shoulder of the pusher bar. The shoulder of the pusher bar may engage the at least one fin of the advancer plate during a distal and a proximal movement of the pusher bar to effectuate one of a distal and proximal movement of the advancer plate.

The pusher bar may include a pusher formed at a distal end thereof, wherein the pusher has a narrow profile for contacting the loaded surgical staple at a single location. The pusher may define a plane that is oriented substantially orthogonal to a plane of the loaded surgical staple.

The apparatus may further include a connector plate reciprocally disposed within the shaft assembly. The connector plate may be selectively connected to the pusher bar. In use, during an initial distal movement of the connector plate the pusher bar may be distally advanced and during a further distal movement of the connector plate the connector plate may be disconnected from the pusher bar.

The pusher bar may include a first spring clip supported thereon for detachably connecting to a feature of the shaft assembly when the pusher bar is in an advanced position for maintaining the pusher bar in the advanced position. The pusher bar may further include a second spring clip supported thereon for detachably connecting to a first feature of the connector plate, wherein the first feature of the connector plate disconnects from the second spring clip following the initial distal movement of the connector plate.

The apparatus may further include a clip carrier disposed in the shaft assembly. The clip carrier may be configured to retain the plurality of surgical clips and the clip follower. The second tab of the clip follower may engage features formed in the clip carrier. The clip follower may be incrementally advanced through the shaft assembly. The clip follower may include a catch extending from a surface thereof. The catch may engage the pusher bar following firing of a last surgical clip and may prevent movement of the pusher bar in a proximal direction.

The apparatus may further include a ratchet assembly disposed in the handle assembly. The ratchet assembly may be prevented from re-setting when the pusher bar does not return to a proximal position.

The apparatus may further include a counter supported in the housing assembly, wherein the counter may provide an indication when a surgical clip has been loaded or fired. The apparatus may further include an indicator supported in the housing assembly, wherein the indicator may provide at least one of an audible and a tactile indication when at least one of a surgical clip is loaded into the jaws, a surgical clip is fired and the apparatus is re-set.

The apparatus may further include a wedge plate reciprocally disposed within the shaft assembly. The wedge plate may be movable between a position where a distal end thereof is disposed in the jaws and a position where the distal end thereof is free from said jaws. The wedge plate may further include a third spring clip supported thereon for selectively engaging a second feature of the connector plate, wherein the second feature of the connector plate may selectively disengage from the third spring clip following an initial distal movement of the connector plate.

The apparatus may further include a drive bar actuatable by the handle assembly and connected to the connector plate for effecting movement of the connector plate. The apparatus may further include a drive channel reciprocally disposed within the shaft assembly, wherein the drive bar may selectively engage the drive channel to effect translation of the drive channel, and wherein a distal end of the drive channel may engage a surface of the jaws upon distal advancement thereof to effectuate approximation of the jaws. The drive channel may actuate a wedge lock plate upon distal advancement thereof to cause proximal movement of the wedge plate to withdraw the distal end of the wedge plate from the jaws and may permit the drive channel to approximate the jaws.

The shaft assembly may be rotatable, about the longitudinal axis, with respect to the handle assembly. The shaft assembly may include a cuff supported therein, wherein the cuff may prevent the third spring clip from splaying outwardly as the third spring clip translates thereacross.

The wedge plate and/or drive channel may be biased to a proximal position.

According to a further aspect of the present disclosure an apparatus for application of surgical clips to body tissue is provided wherein the apparatus includes a handle assembly and a shaft assembly extending distally from the handle assembly and defining a longitudinal axis. The handle assembly includes a trigger and a drive bar reciprocally translatable by the trigger upon an actuation thereof. The shaft assembly includes a housing; a plurality of surgical clips disposed within the housing; a jaw mounted adjacent a distal end portion of the housing, the jaw being movable between an open spaced-apart condition and a closed approximated condition; a pusher bar reciprocally disposed within the housing, the pusher bar being configured to load a distal-most surgical clip into the jaws while the jaws are in the open condition and remain in contact with the loaded surgical clip during an approximation of the jaws; an advancer plate reciprocally disposed within the housing, adjacent to the pusher bar, the advancer plate including at least one fin selectively engageable by a shoulder of the pusher bar, wherein the shoulder of the pusher bar engages the at least one fin of the advancer plate during a distal and a proximal movement of the pusher bar to effectuate one of a distal and proximal movement of the advancer plate; a clip carrier disposed within the housing adjacent the advancer plate, wherein the clip carrier is configured to retain the plurality of surgical clips; a clip follower slidably supported in the clip carrier at a location proximal of the plurality of surgical clips, the clip follower being configured to urge the plurality of surgical clips in a distal direction, the clip follower including a first tab projecting from a first surface thereof and a second tab projecting from a second surface thereof, wherein the first tab of the clip follower engages the advancer plate as the advancer plate is moved distally such that the clip follower is moved distally to advance the plurality of surgical clips, and wherein the second tab of the clip follower engages the clip carrier as the advancer plate is moved proximally such that the clip follower remains stationary; a drive channel reciprocally disposed within the housing adjacent the clip carrier, wherein the drive bar selectively engages the drive channel to effect translation of the drive channel, wherein a distal end of the drive channel engages a surface of the jaws upon distal advancement thereof to effectuate approximation of the jaws; and a wedge plate reciprocally disposed within the housing adjacent the drive channel, the wedge plate being movable between a position where a distal end thereof is disposed in the jaws and a position where the distal end thereof is free from said jaws.

The pusher bar may include a pusher formed at a distal end thereof. The pusher may have a narrow profile for contacting the loaded surgical staple at a single location. The pusher may define a plane that is oriented substantially orthogonal to a plane of the loaded surgical staple. The pusher bar may include a first spring clip supported thereon for selectively engaging a feature of the housing of shaft assembly when the pusher bar is in an advanced position for selectively maintaining the pusher bar in the advanced position. The pusher bar may further include a second spring clip supported thereon for selectively engaging a first feature of the connector plate, wherein the first feature of the connector plate selectively disengages from the second spring clip following the initial distal movement of the connector plate.

The clip follower may be incrementally advanced through the shaft assembly. The clip follower may include a catch extending from a surface thereof. In use, the catch may engage the pusher bar following firing of a last surgical clip and may prevent movement of the pusher bar in a proximal direction.

The handle assembly may further include a ratchet assembly disposed therein. In use, the ratchet assembly may be prevented from re-setting when the pusher bar does not return to a proximal position. The handle assembly may further include a counter supported in the housing assembly, wherein the counter may provide an indication when a surgical clip has been fired. The handle assembly may still further include an indicator supported therein. The indicator may provide at least one of an audible and a tactile indication indicating an event. For example, the event may be at least one of a surgical clip is loaded into the jaws, a surgical clip is fired and the apparatus is re-set.

The wedge plate may further include a third spring clip supported thereon for selectively engaging a second feature of the connector plate. In use, the second feature of the connector plate may selectively disengage from the third spring clip following an initial distal movement of the connector plate.

The shaft assembly may include a wedge plate lock. In use, the drive channel may actuate the wedge plate lock upon distal advancement thereof to cause proximal movement of the wedge plate to withdraw the distal end of the wedge plate from the jaws and permit the drive channel to approximate the jaws.

The shaft assembly may be rotatable, about the longitudinal axis, with respect to the handle assembly. The shaft assembly may include a cuff supported in the housing, wherein the cuff prevents the third spring clip from splaying outwardly as the third spring clip translates thereacross.

The wedge plate and/or the drive channel may be biased to a proximal position.

BRIEF DESCRIPTION OF THE DRAWINGS

The present clip applier will be more fully appreciated as the same becomes better understood from the following detailed description when considered in connection with the following drawings, in which:

FIG. 2 is a rear, perspective view of the clip applier of FIG. 1 illustrating a rotation of a shaft assembly thereof;

FIG. 3 is a front, perspective view of a distal end of the shaft assembly of the clip applier of FIGS. 1 and 2;

FIG. 10 is a right side, front perspective view of the shaft assembly of FIG. 9, shown in an assembled condition;

FIG. 11 is an enlarged view of the indicated area of detail of FIG. 10;

FIG. 12 is a right side, front perspective view of the shaft assembly of FIGS. 9-11, shown with an upper housing removed therefrom;

FIG. 13 is an enlarged view of the indicated area of detail of FIG. 12;

FIG. 14 is an enlarged view of the indicated area of detail of FIG. 12;

FIG. 15 is an enlarged view of the indicated area of detail of FIG. 12;

FIG. 16 is a perspective view, with parts separated, of a proximal end of a pusher bar and a snap clip of the shaft assembly of FIGS. 9-15;

FIG. 17 is a bottom, plan view of the shaft assembly of FIGS. 9-15, illustrating the proximal end of the pusher bar and the snap clip disposed in the upper housing;

FIG. 18 is a right side, front perspective view of the shaft assembly of FIGS. 9-17, shown with an upper housing and the pusher bar removed therefrom;

FIG. 19 is an enlarged view of the indicated area of detail of FIG. 18;

FIG. 20 is an enlarged view of the indicated area of detail of FIG. 18;

FIG. 21 is a right side, front perspective view of the shaft assembly of FIGS. 9-20, shown with an upper housing, the pusher bar and an advancer plate removed therefrom;

FIG. 22 is an enlarged view of the indicated area of detail of FIG. 21;

FIG. 27 is a left side, front perspective view of the shaft assembly of FIGS. 9-26, shown with an upper housing, the pusher bar, the advancer plate, the clip carrier, the drive channel and a wedge plate removed therefrom;

FIG. 28 is an enlarged view of the indicated area of detail of FIG. 27;

FIG. 29 is an enlarged view of the indicated area of detail of FIG. 27;

FIG. 30 is a left side, front perspective view of a lower housing of the shaft assembly of FIGS. 9-29;

FIG. 31 is an enlarged view of the indicated area of detail of FIG. 30;

FIG. 31A is an enlarged view of the indicated area of detail of FIG. 30;

FIG. 32 is a longitudinal, cross-sectional view of the clip applier of FIGS. 1-31A, illustrating the clip applier in an unactuated condition;

FIG. 33 is an enlarged view of the indicated area of detail of FIG. 32;

FIG. 34 is a longitudinal, cross-sectional view of a distal end of the shaft assembly of the clip applier of FIGS. 1-31A;

FIG. 35 is a cross-sectional view as taken through 35-35 of FIG. 34;

FIG. 36 is an enlarged view of the indicated area of detail of FIG. 34;

FIG. 37 is a cross-sectional view as taken through 37-37 of FIG. 36;

FIG. 38 is an enlarged view of the indicated area of detail of FIG. 34;

FIG. 39 is a cross-sectional view as taken through 39-39 of FIG. 38;

FIG. 40 is an enlarged view of the indicated area of detail of FIG. 34;

FIG. 41 is a cross-sectional view as taken through 41-41 of FIG. 40;

FIG. 42 is an enlarged view of the indicated area of detail of FIG. 34;

FIG. 43 is a cross-sectional view as taken through 43-43 of FIG. 42;

FIGS. 48 and 49 are enlarged views of the cross-section taken through 41-41 of FIG. 40 of the shaft assembly, during the initial actuation of the clip applier;

FIG. 55 is a longitudinal, cross-sectional view of the clip applier of FIGS. 1-54, illustrating the clip applier during a further actuation thereof;

FIG. 56 is an enlarged view of the indicated area of detail of FIG. 55;

FIG. 57 is an enlarged view of the indicated area of detail 36 of FIG. 34, during the further actuation of the clip applier;

FIG. 58 is an enlarged view of the indicated area of detail 40 of FIG. 34, during the further actuation of the clip applier;

FIGS. 59 and 60 are longitudinal, cross-sectional views of the shaft assembly illustrating a movement of the pusher bar during the further actuation of the clip applier, and a connection of a clip supported thereon to a boss of the upper housing;

FIG. 61 is an enlarged view of the indicated area of detail 40 of FIG. 34, during the further actuation of the clip applier;

FIG. 62 is an enlarged view of the indicated area of detail 42 of FIG. 34, during the further actuation of the clip applier;

FIGS. 67-69 are longitudinal cross-sectional views of the shaft assembly illustrating a movement of a connector plate during the further actuation of the clip applier;

FIGS. 67A-69A are longitudinal cross-sectional views of the shaft assembly illustrating a movement of a connector plate during the further actuation of the clip applier, according to an alternate embodiment of the present disclosure;

FIG. 70 is a longitudinal, cross-sectional view of the clip applier of FIGS. 1-69, illustrating the clip applier during a final actuation thereof;

FIG. 71 is an enlarged view of the indicated area of detail of FIG. 70;

FIG. 72 is an enlarged view of the indicated area of detail 42 of FIG. 34, during the final actuation of the clip applier;

FIGS. 73 and 74 are front, perspective views of the distal end of the shaft assembly illustrating an actuation of the jaws during the final actuation of the clip applier;

FIG. 84 is front, perspective view of a distal end of the shaft assembly when the clip applier is in a locked-out condition;

FIG. 85 is an enlarged view of the indicated area of detail 42 of FIG. 34, when the clip applier is in a locked-out condition; and FIG. 86 is an enlarged view of the indicated area of detail 71 of FIG. 70, when the clip applier is in a locked-out condition.

DETAILED DESCRIPTION OF EMBODIMENTS

Figure 1:
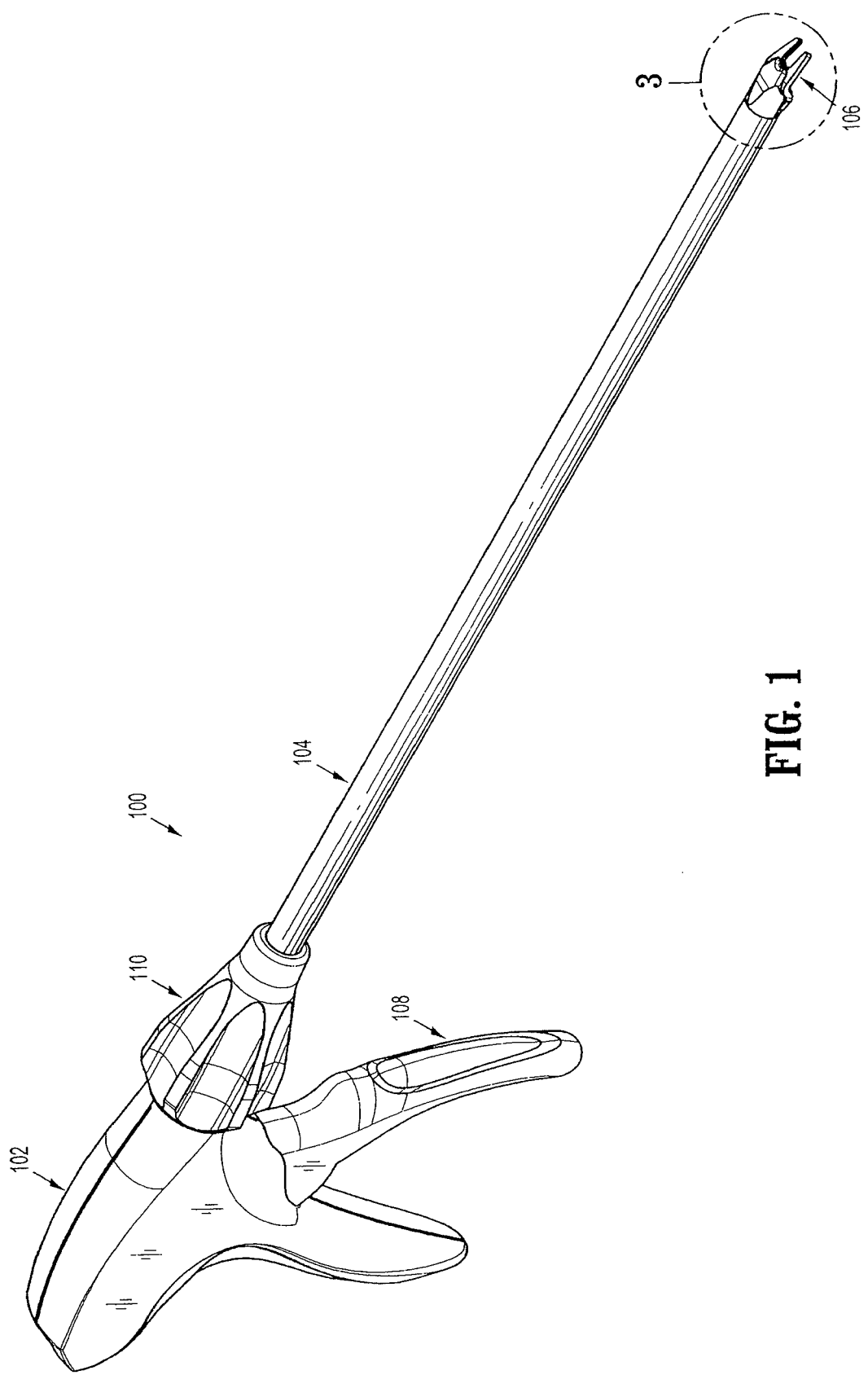
FIG. 1 is a front, perspective view of a surgical clip applier according to an embodiment of the present disclosure.
Figure 4:
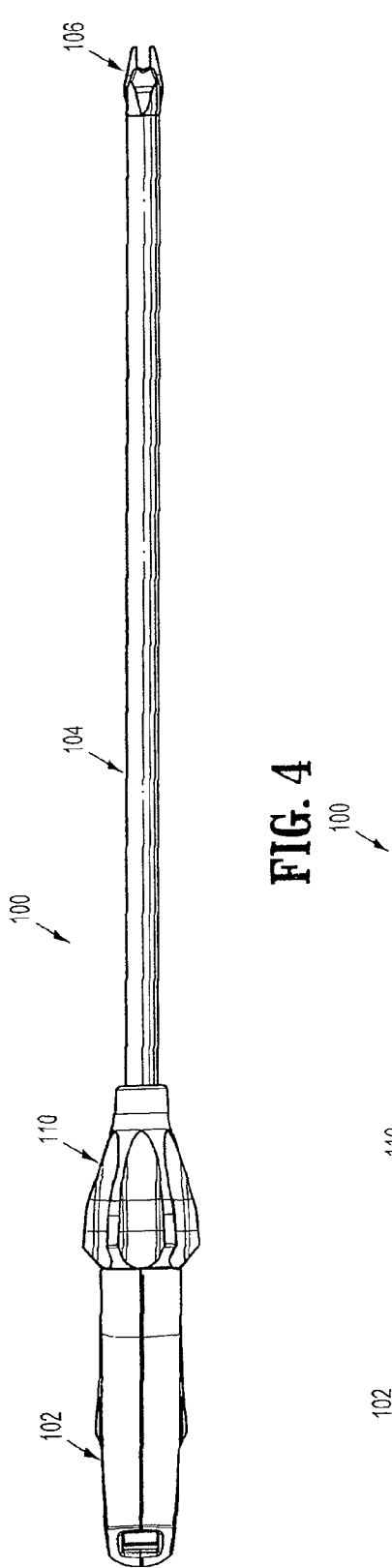
FIG. 4 is a top, plan view of the clip applier of FIGS. 1 and 2.
Figure 5:
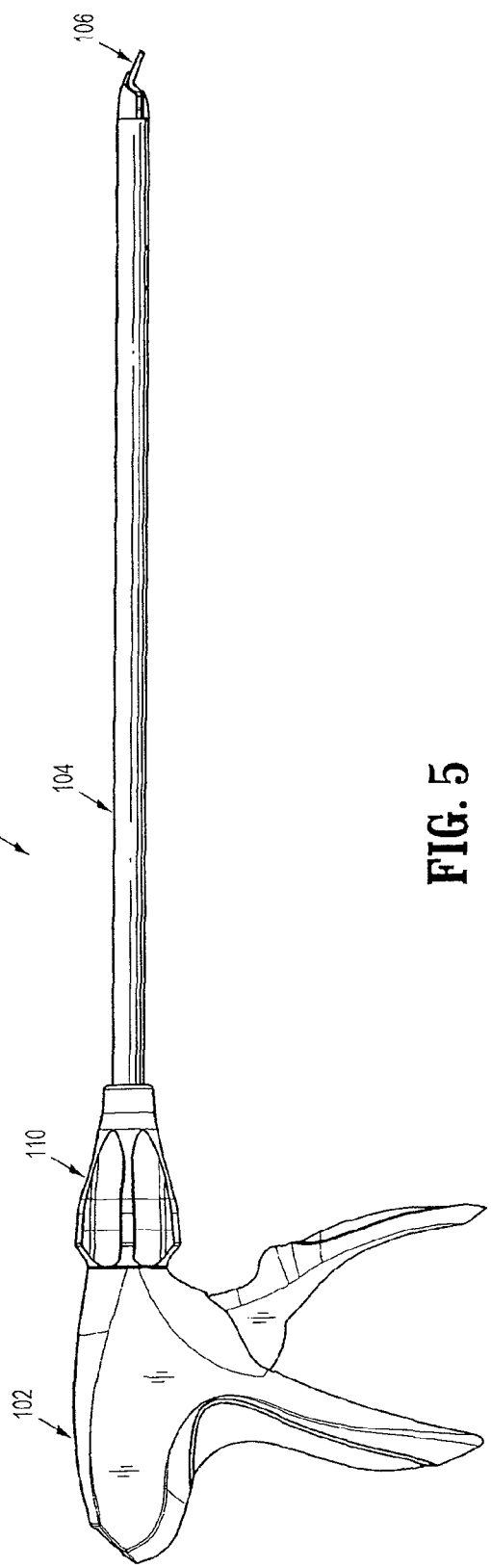
FIG. 5 is a side, elevational view of the clip applier of FIGS. 1 and 2.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-5, a surgical clip applier in accordance with an embodiment of the present disclosure is generally designated as 100. Clip applier 100 includes a handle assembly 102 and an endoscopic portion including a shaft assembly 104 extending distally from handle assembly 102.

Shaft assembly 104 has an outer diameter of about 10 mm. Shaft assembly 104 may have various elongated or shortened lengths depending on intended use, such as, for example, in bariatric surgery.

As seen in FIGS. 1-5, surgical clip applier 100 includes a pair of jaws 106 mounted on a distal end of shaft assembly 104 and actuatable by a trigger 108 of handle assembly 102. Jaws 106 are formed of a suitable biocompatible material such as, for example, stainless steel or titanium and define a channel 106a therebetween for receipt of a surgical clip "C" therein. When jaws 106 are in an open or un-approximated condition relative to each other, a width of jaws 106 measures greater than an outer diameter of shaft assembly 104.

Jaws 106 are mounted in the distal end of shaft assembly 104 such that they are longitudinally stationary relative thereto. A knob 110 may be rotatably mounted on a distal end of handle assembly 102 and affixed to shaft assembly 104 to transmit and/or provide 360° rotation to shaft assembly 104 and jaws 106 about a longitudinal axis thereof (see FIG. 2).

Referring now to FIGS. 1-8, handle assembly 102 of surgical clip applier 100 is shown. Handle assembly 102 includes a housing 103 having a first or right side half-section 103a and a second or left side half-section 103b. Handle assembly 102 includes a trigger 108 pivotably supported between right side half-section 103a and left side half-section 103b. Handle assembly 102 defines a window 103c formed in housing 103 for supporting and displaying a counter mechanism, as will be discussed in greater detail below. Housing 103 of handle assembly 102 may be formed of a suitable plastic material.

Housing 103 supports a drive assembly 120 between right side half-section 103a and left side half-section 103b. Drive assembly 120 includes a wishbone link 122 having a first end pivotally connected to trigger 108, and a second end pivotally connected to a crank plate 124. As seen in FIGS. 6-9, drive assembly 120 further includes a drive connector 134 rotatably connected to crank plate 124, a plunger 135 interconnected to drive connector 134, and a spring 136 supported on drive connector 134. Plunger 135 defines a longitudinal slot 135a configured and adapted to receive a proximal end of a drive bar 140 therein.

Figure 9:
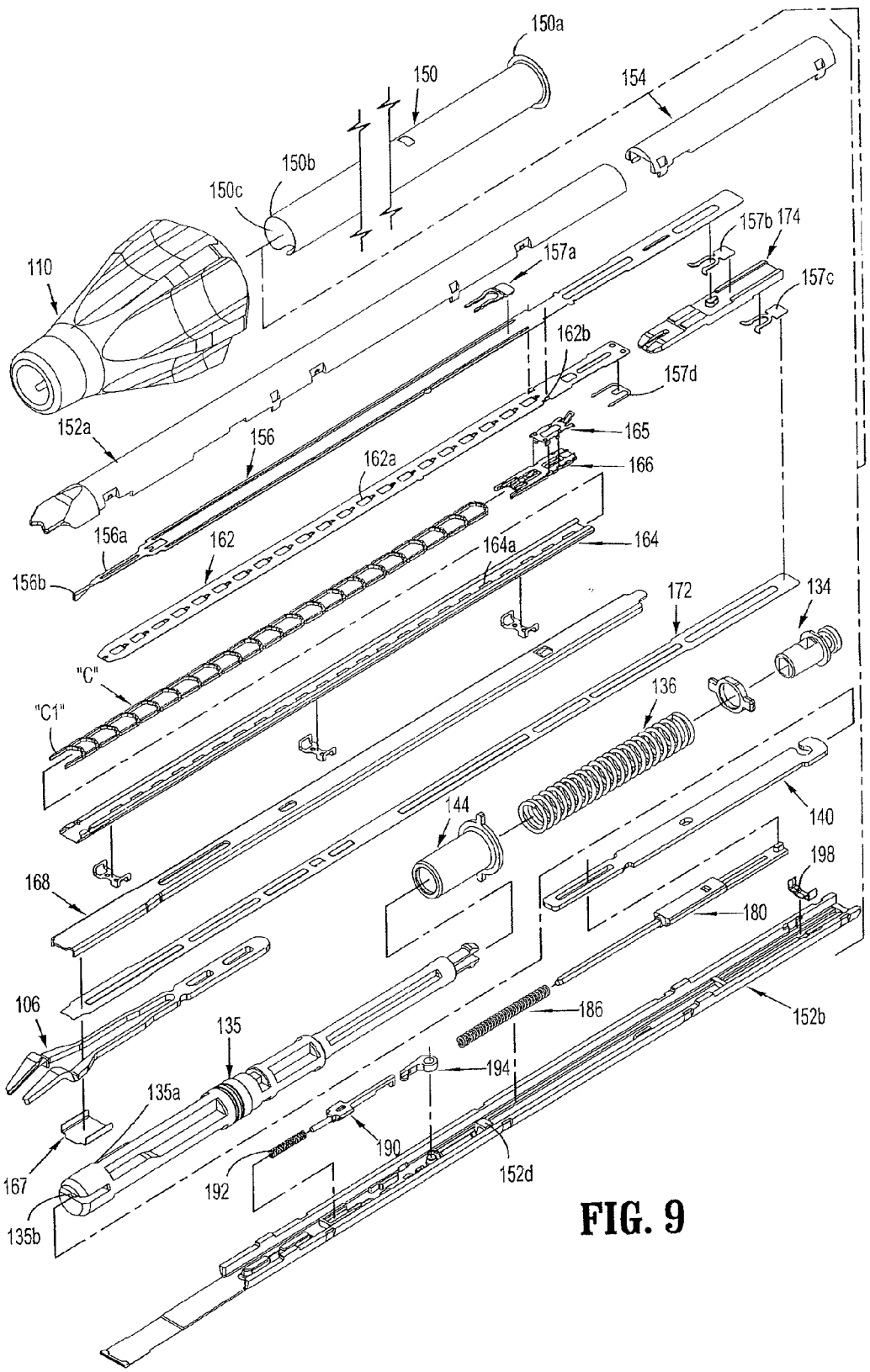
FIG. 9 is a perspective view, with parts separated, of the shaft assembly of the clip applier of FIGS. 1-5.

Drive bar 140 is connected to plunger 135 via an integral pin 135b (see FIG. 9). A cap 144 is provided through which plunger 135 extends. A seal (not shown) is provided to create an air-tight seal between plunger 135 and an outer tube 150.

Figure 6:
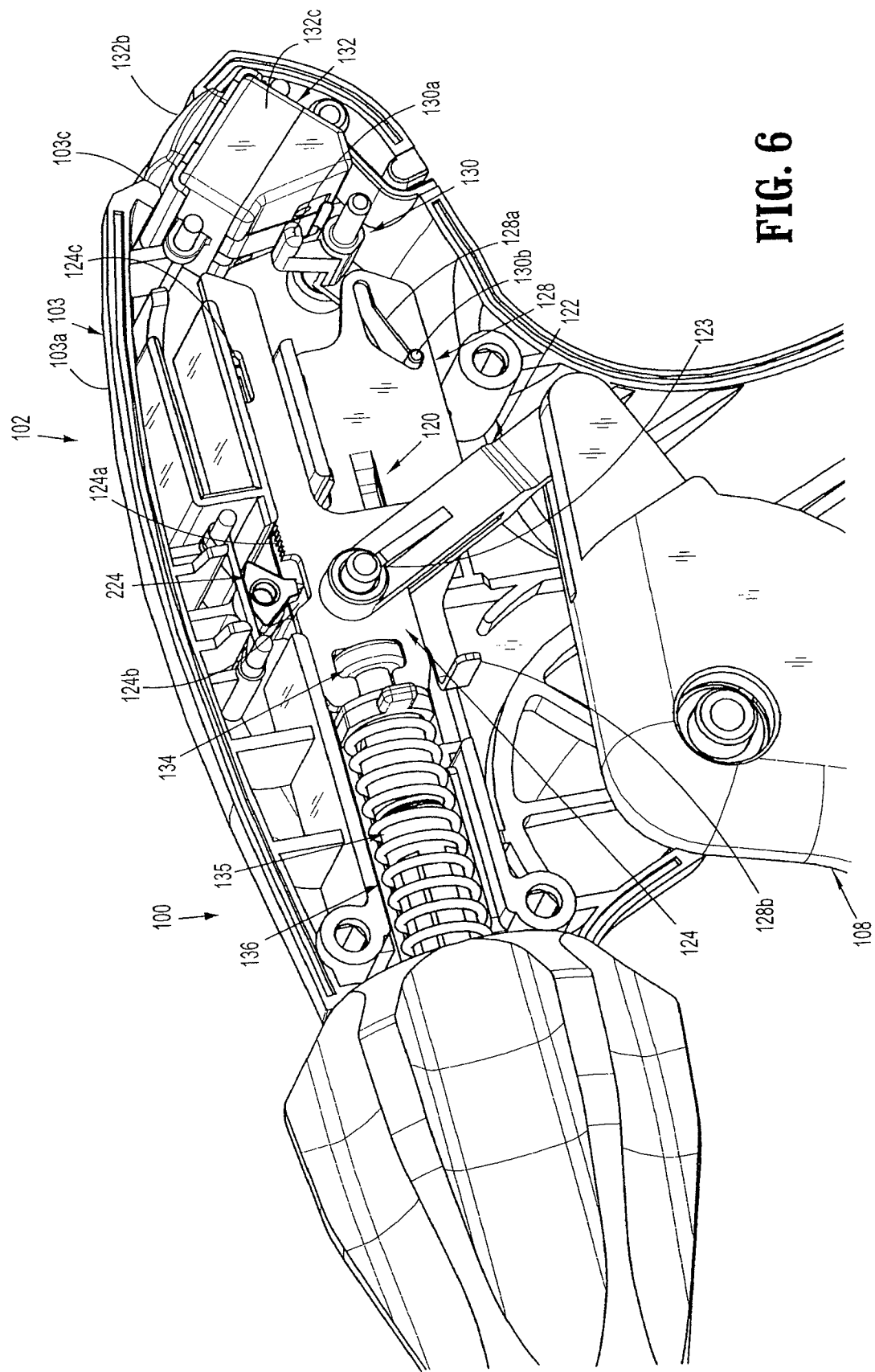
FIG. 6 is a perspective view of a handle assembly of the clip applier of FIG. 1-5, illustrated with a left side housing half-section removed therefrom.
Figure 7:
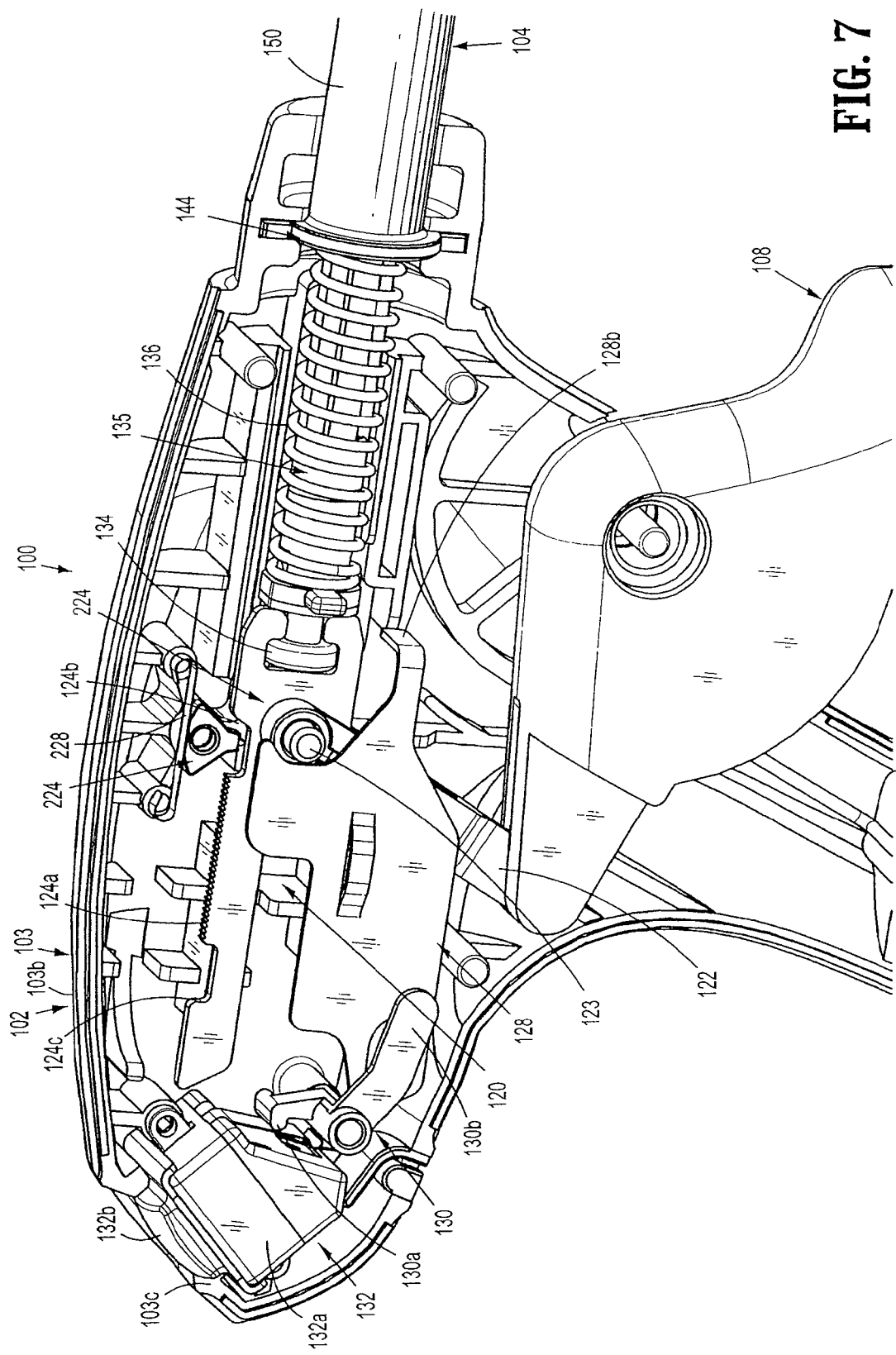
FIG. 7 is a perspective view of a handle assembly of the clip applier of FIG. 1-5, illustrated with a right side housing half-section removed therefrom.
Figure 8:
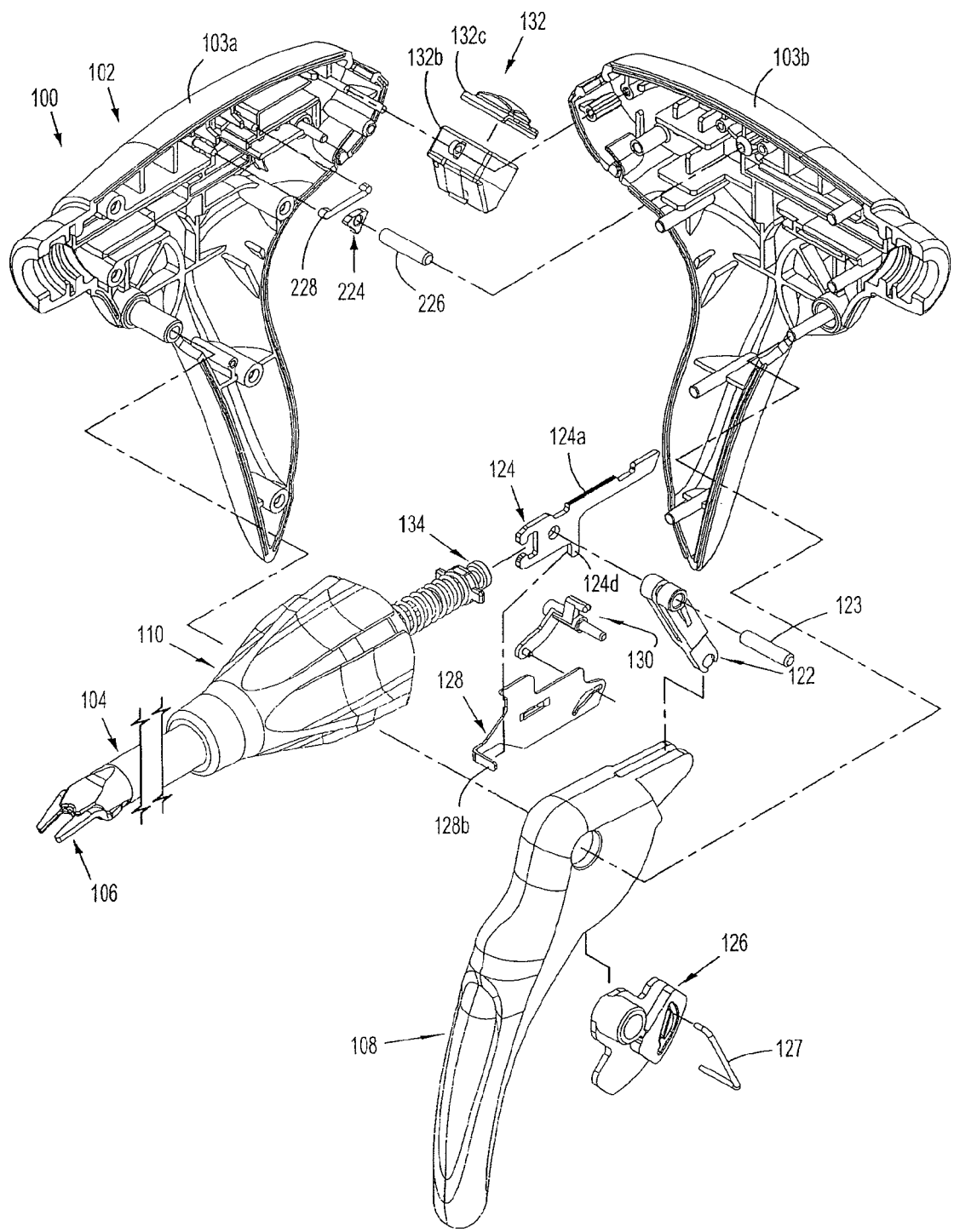
FIG. 8 is a perspective view, with parts separated, of the handle assembly of the clip applier of FIGS. 1-5.

As seen in FIGS. 6-8, handle assembly 102 further includes a rack 124a formed in/on crank plate 124 such that rack 124a is movable therewith. Rack 124a includes a plurality of teeth interposed between a distal recess 124b and a proximal recess 124c defined in crank plate 124. Recesses 124b and 124c are provided to allow pawl 224 to reverse and advance back over the teeth of rack 124a when crank plate 124 changes between proximal and distal movement.

Handle assembly 102 further includes a pawl 224 pivotally connected to housing 103 by a pawl pin 226 at a location wherein pawl 224 is in substantial operative engagement with rack 124a of crank plate 124. Pawl 224 includes a pawl tooth 224a which is selectively engageable with the teeth of rack 124a of crank plate 124. Pawl tooth 224a is engageable with the rack teeth to restrict longitudinal movement of rack 124a and, in turn, crank plate 124 within handle assembly 102. A pawl spring 228 is provided to bias pawl 224 into operative engagement with rack 124a of crank plate 124.

As seen in FIGS. 6-8, crank plate 124 is pivotably connected to wishbone link 122 via a pin 123. Crank plate 124 defines a series of ratchet teeth 124a formed therein for selective engagement with pawl 224.

Figure 8A:
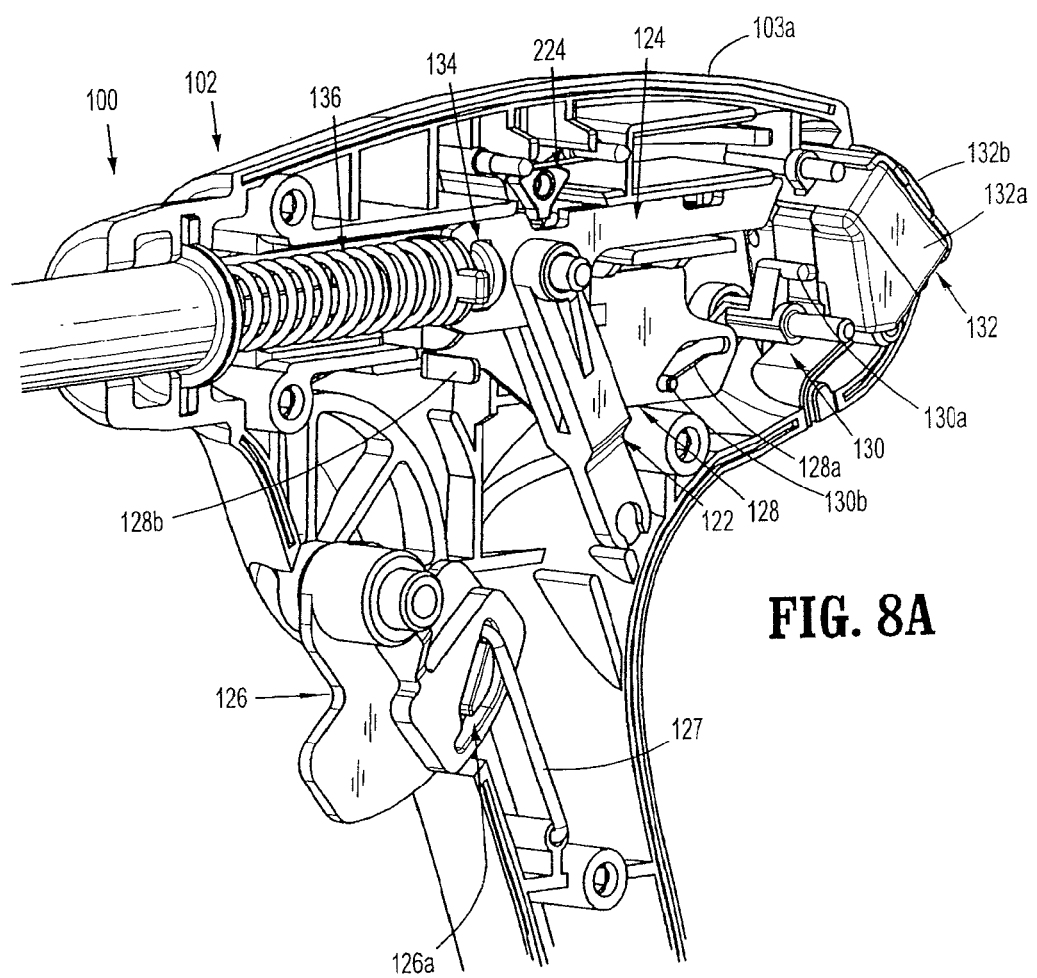
FIG. 8A is a perspective view of the handle assembly of FIGS. 6-8, with a trigger removed therefrom.
Figure 8B:
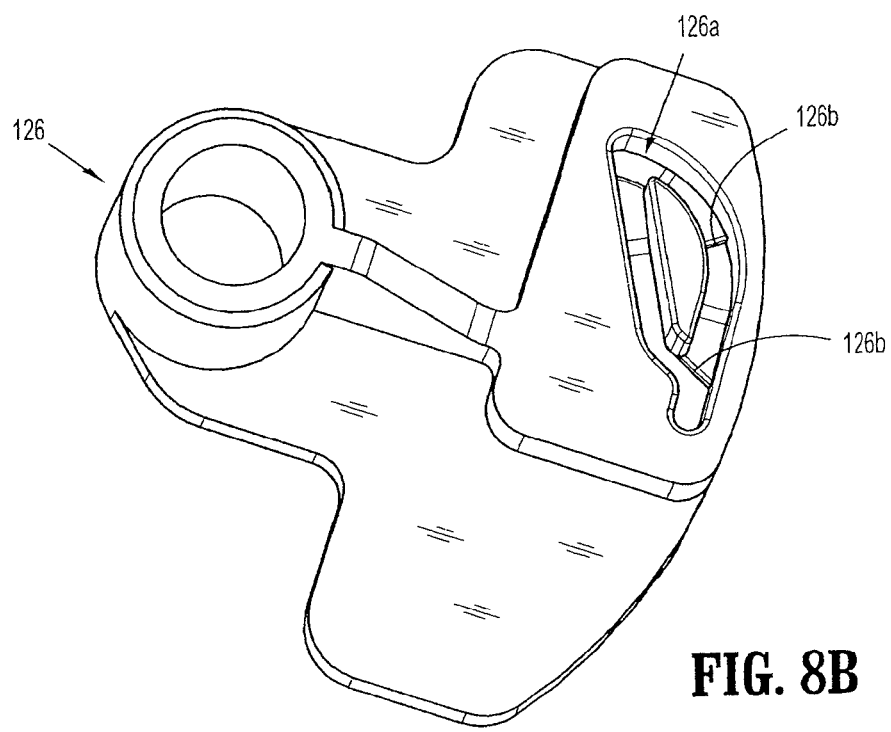
FIG. 8B is a perspective view of a feedback member of the handle assembly of FIGS. 6-8.

As seen in FIGS. 8, 8A and 8B, handle assembly 102 further includes an audible/tactile feedback member 126 operatively associated with trigger 108 so as to rotate together with and about a common axis as trigger 108 is actuated. Feedback member 126 defines a race 126a defining a plurality of ratchets or steps 126b. A deflectable arm 127 is provided and includes a first end operative connected or disposed in race 126a, in contact with steps 126b, of feedback member 126 and a second end connected to housing 103. In operation, as trigger 108 is actuated, arm 127 rides through and/or along race 126a formed in feedback member 126. As will be discussed in greater detail below, as arm 127 moves over steps 126b of feedback member 126, arm 127 snaps over steps 126b and creates an audible sound/click and/or a tactile vibration.

Audible/tactile feedback member 126 includes sufficient steps 126b so as to create an audible/tactile indication after a clip has been fully loaded into the jaws of surgical clip applier 100, after the loaded clip has been formed by the jaws of surgical clip applier 100, and when surgical clip applier 100 is reset to the home position and ready to fire/form another clip.

As seen in FIGS. 6, 7, 8 and 8A, handle assembly 102 of surgical clip applier 100 further includes a counter mechanism 132 supported in housing 103 and visible through window 103c defined in housing 103. Counter mechanism 132 includes a display 132a, a processor 132b, and an energy source (not shown) in the form of a battery or the like.

Display 132a may be any device known in the art to provide an indication of an event. The event may be related to the procedure or the operation of the clip applier 100. Display 132a is a liquid crystal display (LCD).

Display 132a displays one or more operating parameters of clip applier 100 to the surgeon. The operating parameter displayed by display 132a includes an amount or number of clips remaining, a number of clips that have been used, a position parameter, a surgical time of usage, or any other parameter of the procedure.

A Mylar or another polymeric insulating material is disposed between battery or energy source and a contact of processor 132b which prevents the battery or energy source from becoming drained during storage. The tab extends out of housing 103 of surgical clip applier 100 in order to allow for easy removal of the tab therefrom. Once the tab is removed, battery or energy source comes into electrical contact with the contact of processor 132b and in turn energizes display 132a.

As seen in FIGS. 6, 7, 8 and 8A, handle assembly 102 of surgical clip applier 100 further includes a counter actuation mechanism including a counter actuation lever 130 having a first arm 130a configured and adapted to operatively, selectively engage processor 132b of counter mechanism 132. Counter actuation lever 130 further includes a second arm 130b configured and adapted to operatively, slidably engage a slot 128a formed in an actuator plate 128 slidably supported in housing 103.

In operation, as will be described in greater detail below, as trigger 108 is squeezed, trigger 108 causes wishbone link 122 to be advanced distally, causing crank plate 124 to be advanced distally. When arm 124d of crank plate 124 is advanced a predetermined distance, arm 124d engages or contacts finger 128b of actuator plate 128. As crank plate 124 is further advanced distally, crank plate 124 forces or pulls actuator plate 128 in a distal direction thereby actuating counter actuation lever 130 to activate counter mechanism 132.

In particular, when actuator plate 128 is moved distally a sufficient distance, second arm 130b of counter actuation lever 130 is cammed within slot 128b thereof and rotates counter actuation lever 130 resulting in first arm 130a. When actuator plate 128 is moved proximally a sufficient distance, second arm 130b of counter actuation lever 130 is returned to a home position resulting in first arm 130a of counter actuation lever 130 disengaging counter mechanism 132.

Turning now to FIGS. 9-31A, shaft assembly 104 of surgical clip applier 100 is shown and described hereinbelow. Shaft assembly 104 and the components thereof may be formed of suitable biocompatible materials, such as, for example, stainless steel, titanium, plastics and the like. Shaft assembly 104 includes an outer tube 150 having a proximal end 150a supported within housing 103, a distal end 150b, and a lumen 150c extending therethrough. Outer tube 150 is secured within housing 103 by a flange projecting from an outer surface thereof. Shaft assembly 104 further includes an upper housing 152a and a lower housing 152b, each disposed within lumen 150c of outer tube 150. A rear upper housing 154 is disposed within outer tube 150 and proximal of upper housing 152a.

As seen in FIGS. 9, 12 and 13, shaft assembly 104 further includes a pusher bar 156 slidably disposed within upper housing 152a and a rear upper housing 154. Pusher bar 156 includes a distal end 156a defining a narrow-profile pusher 156c configured and adapted to selectively engage/move (i.e., distally advance) a distal-most clip "C1" of a stack of clips "C" and to remain in contact with the distal-most clip "C1" during an initial formation thereof. Pusher bar 156 further includes a proximal end 156b. Pusher bar 156 defines a distal window 156d having a catch 156e, a pair of recesses 156f located proximal of distal window 156d and formed in each side edge thereof, an elongate slot 156g located proximal of side recesses 156f, and a proximal-most window 156h located proximal of slot 156g.

As seen in FIGS. 9 and 14, pusher bar 156 supports a first snap clip 157a along an upper surface thereof at a location distal of side recesses 156f of pusher bar 156. First snap clip 157a is configured in such a manner that the tines thereof project or are spaced an amount from an upper surface of pusher bar 156.

As seen in FIGS. 9 and 15, pusher bar 156 supports a second snap clip 157b along a lower surface thereof at a location proximal of a proximal-most window 156h of pusher bar 156. Second snap clip 157b is oriented in such a manner that the tines thereof project an amount sufficient to overlie proximal-most window 156h of pusher bar 156. The tines of second snap clip 157b are spaced from one another by an amount that is less than a width of proximal-most window 156h of pusher bar 156.

As seen in FIGS. 9 and 16-20, shaft assembly 104 further includes an advancer plate 162 reciprocally supported beneath pusher bar 156. As seen in FIGS. 16 and 17, a fourth snap clip 157d is supported at a proximal end of advancer plate 162. Snap clip 157d includes a pair of tines that are detachably connected in proximal retaining grooves 152m and distal retaining grooves 152n formed in upper housing 152a. In this manner, in use, snap clip 157d detachably engage retaining grooves 152m and distal retaining grooves 152n to maintain advancer plate 162 in a proximal or a distal position. Upon distal advancement of advancer plate 162, the tines of snap clip 157d cam inward and allow advancer plate 162 to continue to move distally.

As seen in FIGS. 18-20, advancer plate 162 includes a series of windows 162a formed therein and extending along a length thereof. As seen in FIG. 19, each window 162a defines a proximal edge that extends below a surface of advancer plate 162 so as to define a lip or ledge 162c. Advancer plate 162 further includes a pair of side fin 162b extending from a side edge thereof, in a direction toward upper housing 152a. As seen in FIG. 15, a pair of side fins 162b are slidably disposed within side recesses 156f of pusher bar 156.

As seen in FIGS. 9 and 21-22, shaft assembly 104 further includes a clip carrier 164 disposed within upper housing 152a, and beneath advancer plate 162. Clip carrier 164 is generally a box-like structure having an upper wall, a pair of side walls and a lower wall defining a channel therethrough. Clip carrier 164 includes a plurality of spaced apart windows 164a (see FIG. 9) formed in the lower wall and extending longitudinally along a length thereof. Clip carrier 164 includes an elongate window formed in the upper wall and extending longitudinally along a length thereof.

As seen in FIGS. 9 and 21, a stack of surgical clips "C" is loaded and/or retained within the channel of clip carrier 164 in a manner so as to slide therewithin and/or therealong. The channel of clip carrier 164 is configured and dimensioned to slidably retain a stack or plurality of surgical clips "C" in tip-to-tail fashion therewithin.

As seen in FIG. 19, a distal end of clip carrier 164 includes a pair of spaced apart, resilient tangs 164b. Tangs 164b are configured and adapted to detachably engage a backspan of a distal-most surgical clip "C1" of the stack of surgical clips "C" retained within clip carrier 164.

As seen in FIGS. 9 and 21-24, shaft assembly 104 of clip applier 100 further includes a clip follower 166 slidably disposed within the channel of clip carrier 164. As will be described in greater detail below, clip follower 166 is positioned behind the stack of surgical clips "C" and is provided to urge the stack of clips "C" forward during an actuation of clip applier 100. As will be described in greater detail below, clip follower 166 is actuated by the reciprocating forward and backward motion of advancer plate 162.

Figure 23:
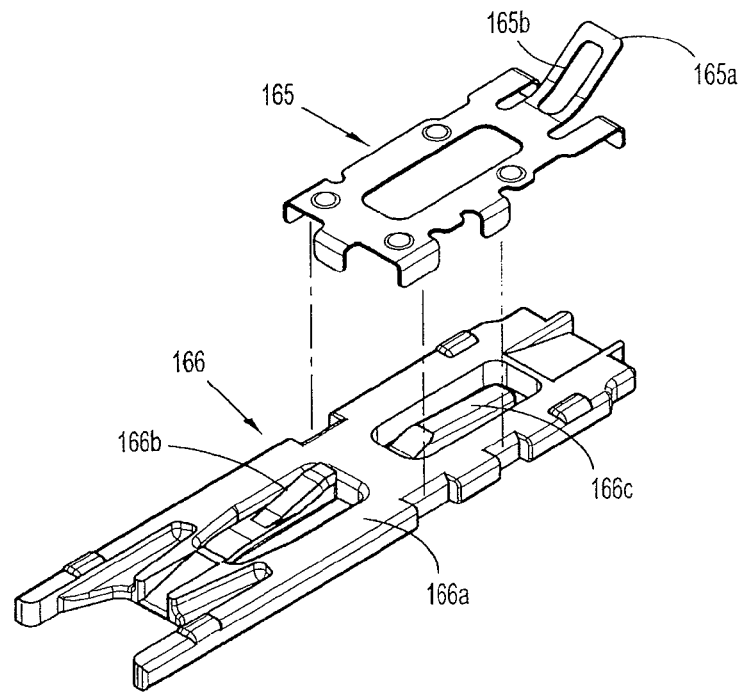
FIG. 23 is a perspective view, with parts separated, of a clip follower and lock-out plate.
Figure 23A:
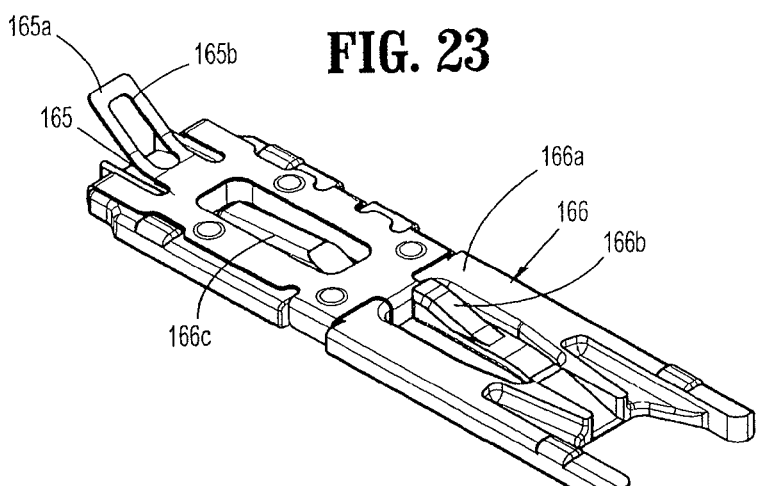
FIG. 23A is a top, perspective view of the assembled clip follower and lock-out plate of FIG. 23.
Figure 24:
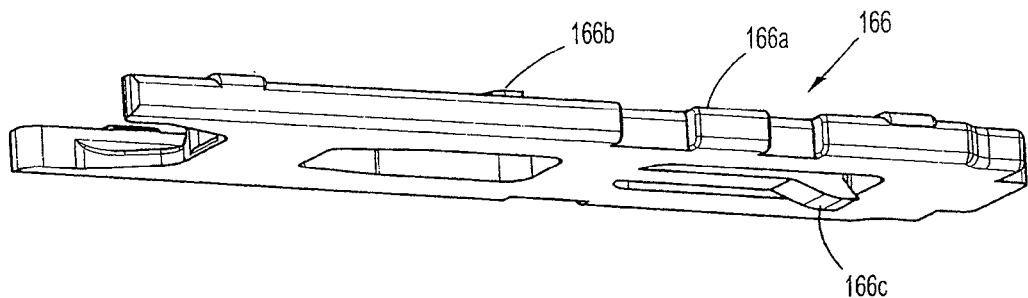
FIG. 24 is a bottom, perspective view of the clip follower of FIG. 23.

As seen in FIGS. 23, 23A and 24, clip follower 166 includes body portion 166a, a distal tab 166b extending substantially upwardly and rearwardly from body portion 166a, and a proximal tab 166c extending substantially downwardly and rearwardly from body portion 166a.

Distal tab 166b of clip follower 166 is configured and dimensioned to selectively engage ledges 162c of windows 162a of advancer plate 162. In use, engagement of distal tab 166b of clip follower 166 against ledges 162c of windows 162a of advancer plate 162 causes clip follower 166 to incrementally advance or travel distally as advancer plate 162 is advanced or moved in a distal direction.

Proximal tab 166c is configured and dimensioned to selectively engage windows 164a formed in clip carrier 164. In use, engagement of proximal tab 166c of clip follower 166 in a window 164a formed clip carrier 164 prevents clip follower 166 from traveling or moving in a proximal direction.

Clip follower 166 includes a lock-out plate 165 supported thereon or alternatively, integrally formed therewith. Lock-out plate 165 includes a resilient tail 165a, defining a window 165b, extending therefrom, in a direction upwardly and rearwardly from body portion 166a of clip follower 166.

Figure 25:
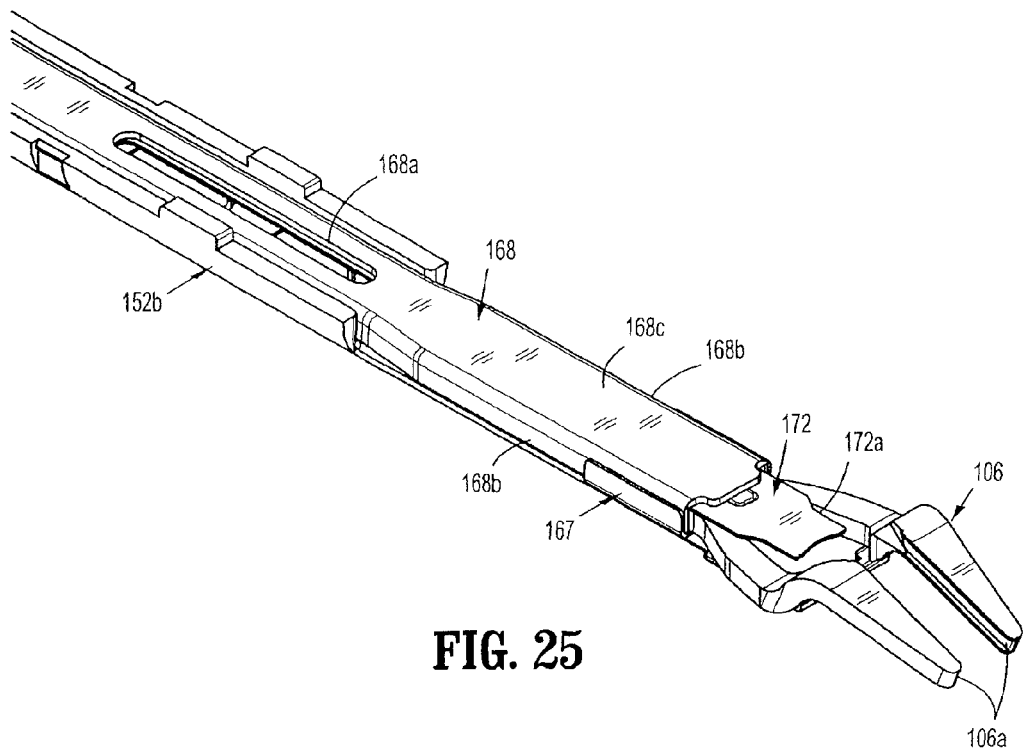
FIG. 25 is a right side, front perspective view of a distal end of the shaft assembly of FIGS. 9-23, shown with an upper housing, the pusher bar, the advancer plate and a clip carrier removed therefrom.

As seen in FIGS. 9, 25 and 38, shaft assembly 104 further includes a drive channel 168 reciprocally supported in channel assembly 104 at a location below clip carrier 164. Drive channel 168 is a substantially U-shaped channel including a pair of spaced apart side walls 168b extending from a backspan 168c thereof, in a direction away from clip carrier 164 and towards lower housing 152b. Drive channel 168 further includes a tab 168d projecting from backspan 168c, at a location proximal of slot 168a, and extending in the direction of side walls 168b. As seen in FIG. 41, drive channel 168 defines a slot or window 168e formed in one of side walls 168b for selectively receiving a tooth 194c of wedge plate release 194.

As seen in FIGS. 9 and 25, shaft assembly 104 of clip applier 100 includes a drive channel strap 167 secured to drive channel 168. Strap 167 is secured to side walls 168b of drive channel 168 so as to extend transversely thereacross. Strap 167 is secured to drive channel 168 at a location distal of elongate slot 168a. Strap 167 is secured to drive channel 168 such that wedge plate 172 extends between backspan 168c of drive channel 168 and jaws 106.

Figure 26:
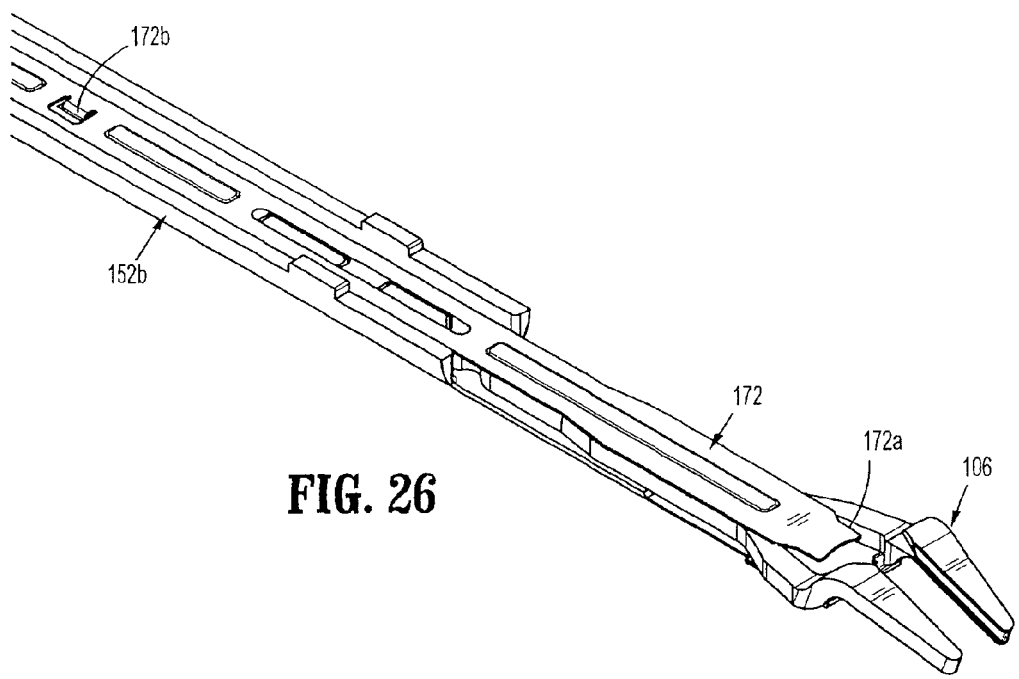
FIG. 26 is a right side, front perspective view of the distal end of the shaft assembly of FIG. 25, shown with an upper housing, the pusher bar, the advancer plate, the clip carrier and a drive channel removed therefrom.

As seen in FIGS. 9, 26 and 27, clip applier 100 includes a pair of jaws 106 mounted on or at a distal end of shaft assembly 104 and actuatable by trigger 108. Jaws 106 are formed of a suitable biocompatible material such as, for example, stainless steel or titanium.

Jaws 106 are mounted adjacent a distal end of drive channel 168, via bosses formed in lower housing 152b that engage receiving slots formed in jaws 106, such that jaws 106 are held stationary relative to drive channel 168. As seen in FIG. 25, jaws 106 define a channel 106a therebetween for receipt of a surgical clip "C" therein.

As seen in FIGS. 9, 25 and 26, shaft assembly 104 of clip applier 100 further includes a wedge plate 172 having a distal end interposed between drive channel 168 and jaws 106 and a proximal end extending through shaft assembly 104. Wedge plate 172 includes a substantially tapered distal end 172a for selective operative interposition between jaws 106. As seen in FIG. 26, wedge plate 172 defines a fin or tab 172b projecting from a lower surface thereof. As seen in FIG. 22, wedge plate 172 defines a proximal-most slot 172c formed therein for slidably receiving a second stem 174c of a connector plate 174 therein.

As seen in FIG. 22, a third snap clip 157c is supported at a proximal end of wedge plate 172. Third snap clip 157c is oriented in such a manner that the tines thereof project an amount sufficient to overlie proximal-most window 172c formed in wedge plate 172. The tines of third snap clip 157c are spaced from one another by an amount that is less than a width of proximal-most window 172c of wedge plate 172.

As seen in FIGS. 9, 18, 20 and 36, shaft assembly 104 of clip applier 100 further includes a connector plate 174 slidably interposed between pusher bar 156 and wedge plate 172 and detachably connectable to each of pusher bar 156 and wedge plate 172. Connector plate 174 includes a tapered distal end 174a, a first stem 174b extending from an upper surface thereof and a second stem 174c extending from a bottom surface thereof. Each stem 174b, 174c has a substantially tear-drop shaped profile wherein a distal end of each stem 174b, 174c is larger than a proximal end thereof.

In operation, first stem 174b of connector plate 174 is configured and dimensioned for detachable connection with second snap clip 157b that is secured to pusher bar 156, and second stem 174c of connector plate 174 is configured and dimensioned for detachable connection with third snap clip 157c that is secured to wedge plate 172.

As seen in FIGS. 22, 36 and 37, second stem 174c of connector plate 174 extends into a window 140b defined in drive bar 140. In this manner, as drive bar 140 is also reciprocated, connector plate 174 is reciprocated therewith.

As seen in FIG. 31A, a guard 198 is supported in lower housing 152b at a location so as to maintain the relative distance between the tines of the third snap-clip 157c during an initial distal advancement thereof. In this manner, second stem 174b of connector plate 174 can not prematurely disengage from third snap clip 157c until third snap clip 157c has surpassed guard 198.

As seen in FIGS. 9, 27, 29 and 41, shaft assembly 104 of clip applier 100 further includes a slider joint 180 slidably supported within a channel of lower housing 152b. Slider joint 180 includes a body portion 182 and a rod 184 extending therefrom. When properly positioned within the channel of lower housing 152b, rod 184 of slider joint 180 extends in a substantially distal direction. Rod 184 of slider joint 180 slidably passes through a stub 152d formed in and extending from the channel of lower housing 152b (see FIG. 29). Shaft assembly 104 further includes a biasing member 186, in the form of a compression spring, supported on rod 184 and interposed between stub 152d of lower housing 152b and body portion 182 of slider joint 180.

Body portion 182 of slider joint 180 includes a boss 182a formed near a proximal end thereof, and configured and adapted for slidable engagement in elongate slot 140a of drive bar 140 (see FIG. 29). Body portion 182 of slider joint 180 further includes a pocket 182b formed near a distal end thereof, and configured and adapted for receiving tab 168d of drive channel 168 therein (see FIGS. 38 and 39).

As seen in FIGS. 9, 27 and 28, shaft assembly 104 of clip applier 100 further includes a wedge plate lock 190 slidably supported in the channel of lower housing 152b and in drive channel 168. Wedge plate lock 190 includes a body portion 190a, a rod 190b extending distally from body portion 190a, a tail 190c extending proximally from body portion 190a, a pocket 190d formed in an upper surface of body portion 190a, and a stem or tooth 190e extending from tail 190c. Shaft assembly 104 further includes a biasing member 192, in the form of a compression spring, supported on rod 190b and interposed between lower housing 152b of and body portion 190a of wedge plate lock 190.

Shaft assembly 104 of clip applier 100 further includes a wedge plate release 194 rotatably supported in the channel of lower housing 152b. Wedge plate release 194 includes a stem 194a configured for engagement with tooth 190e extending from tail 190c of wedge lock plate 190, a hammer 194b extending outwardly from stem 194a in a direction toward tail 190c of wedge plate lock 190, and a tooth 194c extending outwardly from stem 194a in a direction away from tail 190c of wedge plate lock 190.

The operation of surgical clip applier 100, to form or crimp a surgical clip around a target tissue, such as, for example, a vessel, will now be described. With reference to FIGS. 32-43, surgical clip applier 100 is shown prior to any operation or use thereof. As seen in FIGS. 32 and 33, prior to use or firing of clip applier 100, trigger 108 is generally in an uncompressed or unactuated state. As such, crank plate 124 of drive assembly 120 is at a retracted or proximal-most position and thus, plunger 135 and drive bar 140 are also at a retracted position. When crank plate 124 is in the retracted position, pawl 224 is disposed within distal recess 124b defined in crank plate 124.

When drive assembly 120 and drive bar 140 are in the retracted position, as seen in FIGS. 35-37, connector plate 174 is located at a retracted or proximal-most position. With connector plate 174 at a retracted or proximal-most position, pusher bar 156 is also at a retracted or proximal-most position and first tear-drop stem 174b of connector plate 174 is disposed at a proximal end of proximal-most window 156h of pusher bar 156 and retained in snap-fit engagement in the tines of second snap clip 157b. Also, with connector plate 174 at a retracted or proximal-most position, wedge plate 172 is also at a retracted or proximal-most position and second tear-drop stem 174c of connector plate 174 is disposed at a proximal end of proximal-most window 172c of wedge plate 172 and retained in snap-fit engagement in the tines of third snap clip 157c.

As seen in FIGS. 36 and 37, when drive assembly 120 and drive bar 140 are in the retracted position, tab 182a of slider joint 182 is located at a distal-most position in elongate slot 140a of drive bar 140.

As seen in FIGS. 38 and 39, when drive assembly 120 and drive bar 140 are in the retracted position, clip follower 166 is located at a proximal-most end of the channel of clip carrier 164, wherein distal tab 166b of clip follower 166 is operatively disposed within a proximal-most window 162a of advancer plate 162 and proximal tab 166c is operatively disposed within a proximal-most window 164a of clip carrier 164.

With continued reference to FIGS. 38 and 39, when drive assembly 120 and drive bar 140 are in the retracted position, slider joint 180 is located at a proximal-most position and since tab 168d of drive channel 168 is disposed within pocket 182b of slider joint 180, drive channel 168 is also located at a proximal-most position. As seen in FIGS. 38 and 39, slider joint 180 abuts against a physical stop 152e (see FIG. 30) projecting from lower housing 152b.

As seen in FIGS. 40 and 41, when drive assembly 120 and drive bar 140 are in the retracted position, wedge plate lock 190 is located at a proximal-most position such that tooth 190e extending from tail 190c thereof is disposed proximal of a ramped ledge 152f formed in lower housing 152b (see FIGS. 30 and 31). As seen in FIG. 41, wedge plate lock 190 abuts against a physical stop 152g projecting from lower housing 152b. Also as seen in FIG. 41, wedge plate release 194 is disposed in a first position such that tooth 194c thereof projects into window 168e formed in side wall 168b of drive channel 168.

As seen in FIGS. 42 and 43, when drive assembly 120 and drive bar 140 are in the retracted position, pusher 156c of pusher bar 156 is disposed proximal of a backspan of a distal-most clip "C" retained in clip carrier 164. Distal-most clip "C" is retained within the channel of clip carrier 164 by tangs 164b thereof. Also, in this position, as described above, wedge plate 172 is located at a proximal-most position such that distal end 172a thereof is positioned proximal of jaws 106.

As seen in FIG. 43, with drive channel 168 at a proximal-most position, a distal end thereof is disengaged from proximal camming surfaces 106b of jaws 106.

Turning now to FIGS. 44-54, as trigger 108 is squeezed or actuated from the initial position, during a first stage of an initial stroke, trigger 108 causes wishbone link 122 to move crank plate 124 in a distal direction which, in turn, causes drive connector 134 and plunger 135 to move distally and to move drive bar 140 distally. As plunger 135 is moved distally, spring 136 is compressed an initial amount.

Simultaneously therewith, as crank plate 124 is moved distally the teeth of rack 124a engage tooth 224a of pawl 224 as pawl 224 is moved out or rotated of distal recess 124a of crank plate 124. In this manner, crank plate 124 can not return to a proximal-most position without completing a full distal stroke.

Figure 44:
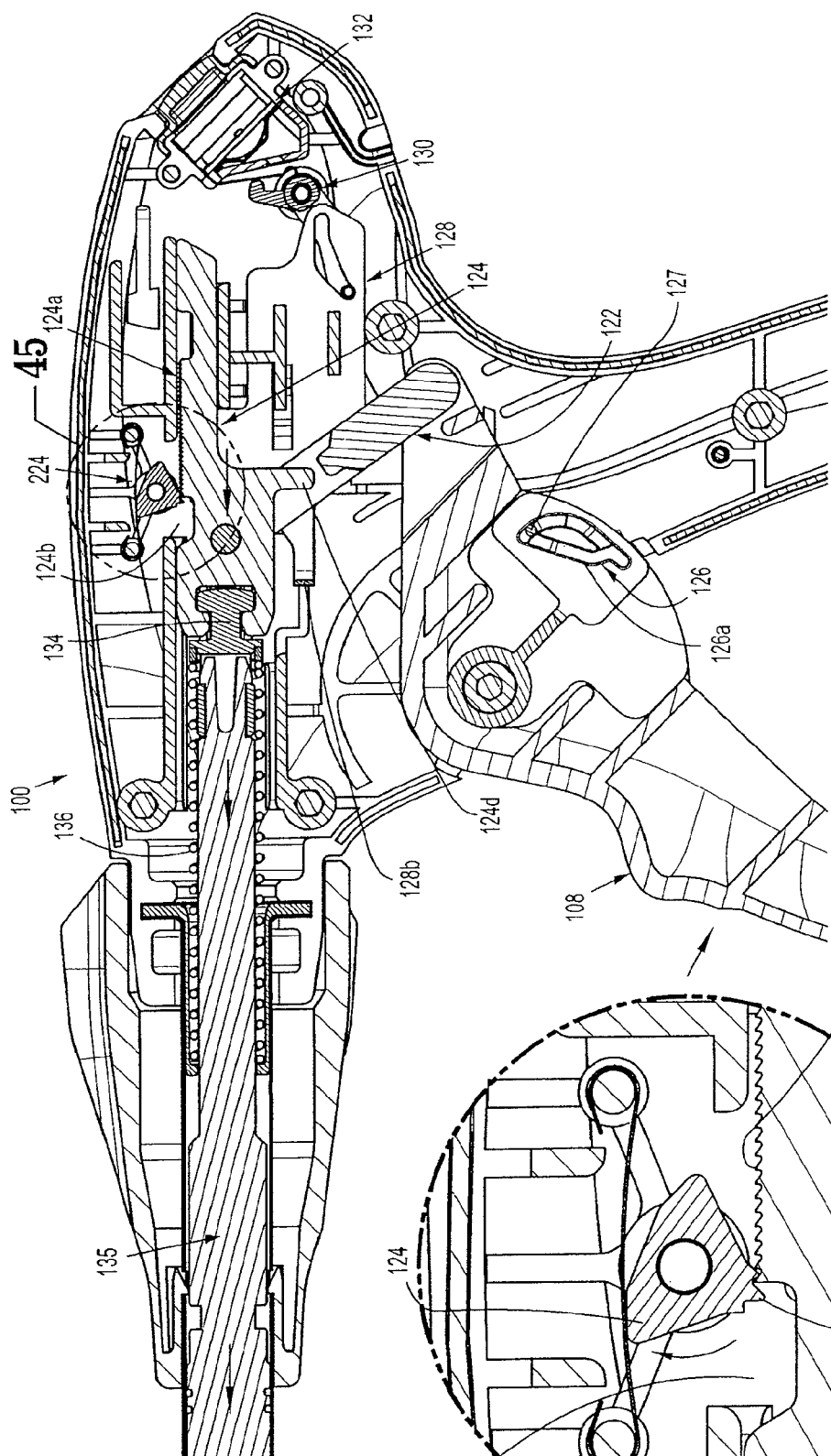
FIG. 44 is a longitudinal, cross-sectional view of the clip applier of FIGS. 1-43, illustrating the clip applier during an initial actuation thereof.
Figure 45:
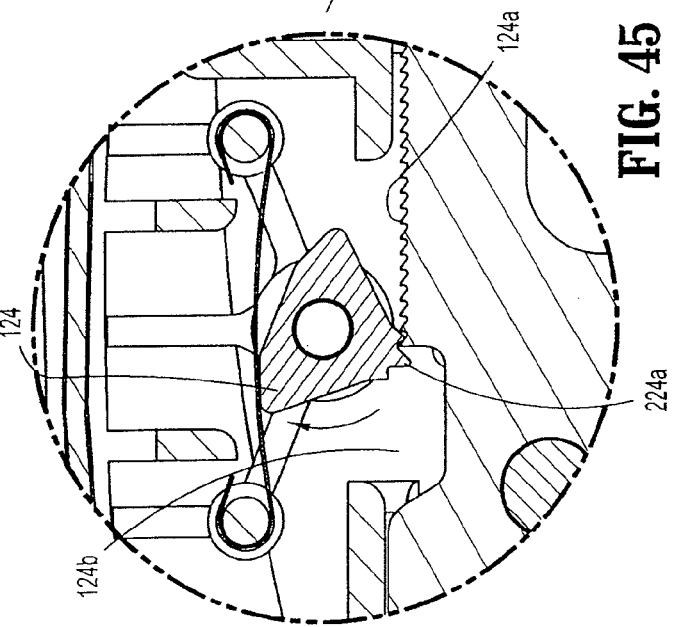
FIG. 45 is an enlarged view of the indicated area of detail of FIG. 44.

As seen in FIG. 44, as trigger 108 is squeezed an initial amount, arm 127 begins to translate through race 126a of feedback member 126.

Figure 46:
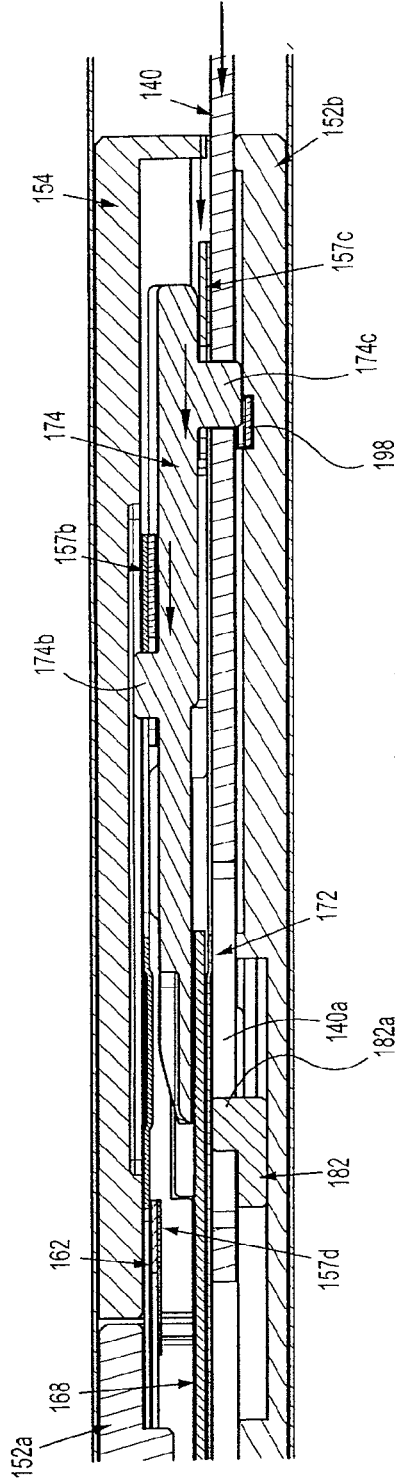
FIG. 46 is an enlarged view of the indicated area of detail 36 of FIG. 34, during the initial actuation of the clip applier.

As seen in FIG. 46, as drive bar 140 is moved in a distal direction, drive bar 140 pushes connector plate 174 in a distal direction. Since pusher bar 156 is selectively connected to connector plate 174 via second snap clip 157b, pusher bar 156 is advanced or pulled in a distal direction. Also, since wedge plate 172 is selectively connected to connector plate 174 via third snap clip 157c, wedge plate 172 is also advanced or dragged in a distal direction.

As drive bar 140 is moved in the distal direction, elongate slot 140a thereof is also moved in a distal direction such that tab 182a of slider joint 182 is translated in a proximal direction relative thereto.

Figure 47:
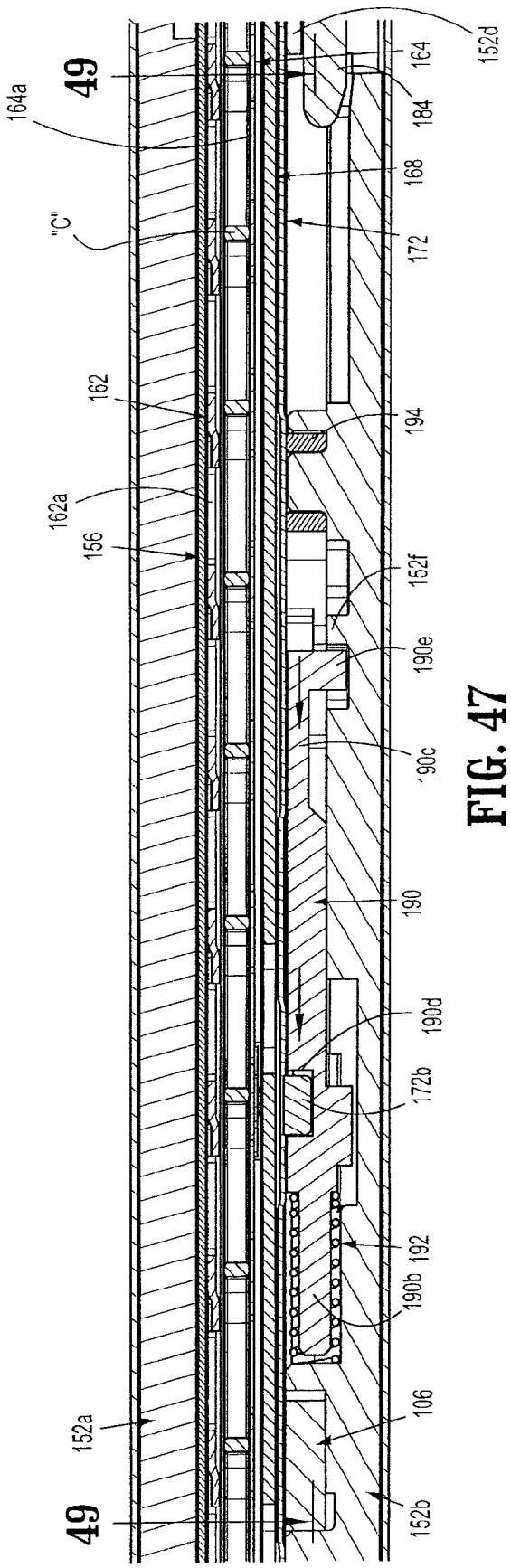
FIG. 47 is an enlarged view of the indicated area of detail 40 of FIG. 34, during the initial actuation of the clip applier.

As seen in FIG. 47-49, as wedge plate 172 is moved in a distal direction, since tab 172b of wedge plate 172 is retained in pocket 190d of wedge plate lock 190, wedge plate lock 190 is moved or dragged in a distal direction causing tooth 190e of tail 190c thereof to cam over ramped ledge 152f formed in lower housing 152b, thereby moving from a position proximal of ramped ledge 152f to a position distal of ramped ledge 152f. As wedge plate lock 190 is moved in a distal direction, biasing member 192 is compressed an initial amount. As seen in FIG. 49, wedge plate lock 190 is moved in a distal direction until wedge plate lock 190 abuts against a physical stop formed in lower housing 152b.

Figure 47A:
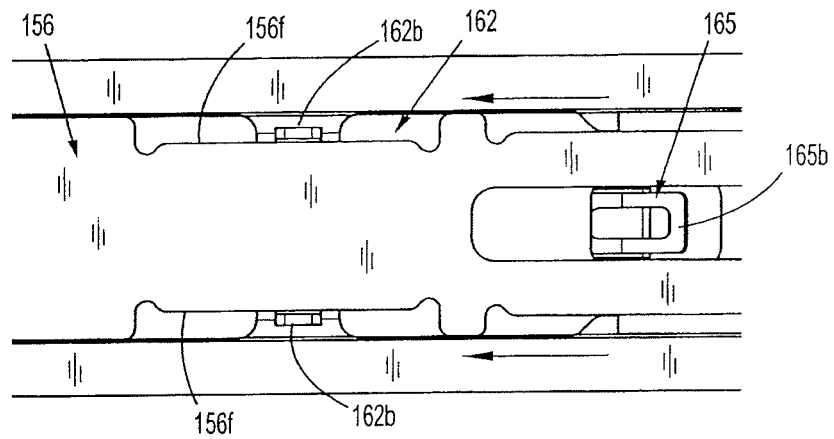
FIG. 47A is a top, plan view of the pusher bar, illustrating a movement of the pusher bar during the initial actuation of the clip applier.

As seen in FIG. 47A, as pusher bar 156 is moved in a distal direction, fins 162b of advancer plate 162 translate, a predetermined distance, within side recesses 156f of pusher bar 156 until fins 162b contact or engage a proximal end of side recesses 156f of pusher bar 156.

Figure 47B:
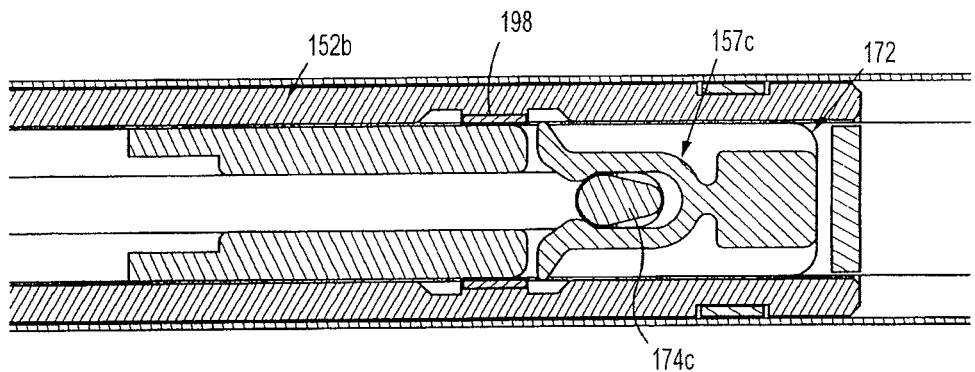
FIGS. 47B and 47C are each longitudinal, cross-sectional views of the shaft assembly, illustrating a movement of the wedge plate during the initial actuation of the clip applier.
Figure 47C:
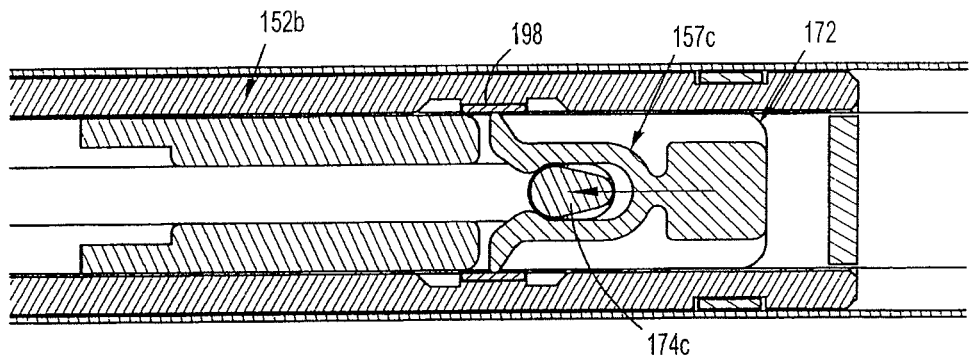

As seen in FIGS. 47B and 47C, as wedge plate 172 is moved in the distal direction, due to the connection of second stem 174c of connector plate 174 with third snap clip 157c, second stem 174c of connector plate 174 is prevented from prematurely disconnecting from third snap clip 157c by guard 198. In particular, guard 198 acts on the tips of the tines of third snap clip 157c to prevent the tines from splaying outward due to the forces acting thereon by the distal forces generated by second stem 174c as connector plate 174 is moved in the distal direction.

Figure 50:
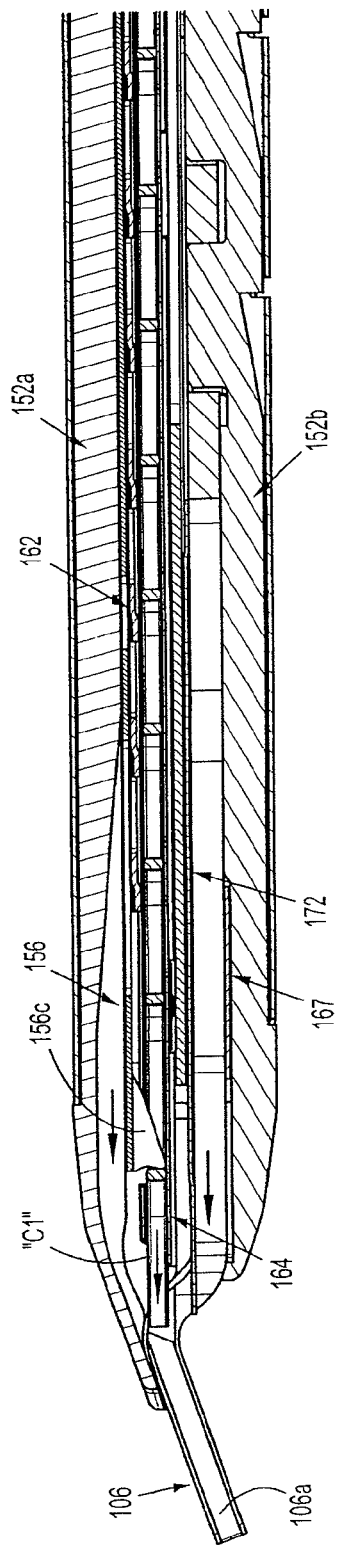
FIG. 50 is an enlarged view of the indicated area of detail 42 of FIG. 34, during the initial actuation of the clip applier.

As seen in FIG. 50, as pusher bar 156 is moved in a distal direction pusher 156c thereof engages a backspan of a distal-most clip "C" and begins to urge distal-most clip "C" in a distal direction. As pusher bar 156 moves distal-most clip "C" in a distal direction, distal-most clip "C" snaps out from behind tangs 164b of clip carrier 164 and begins to enter into channels 106a of jaws 106.

Figure 51:
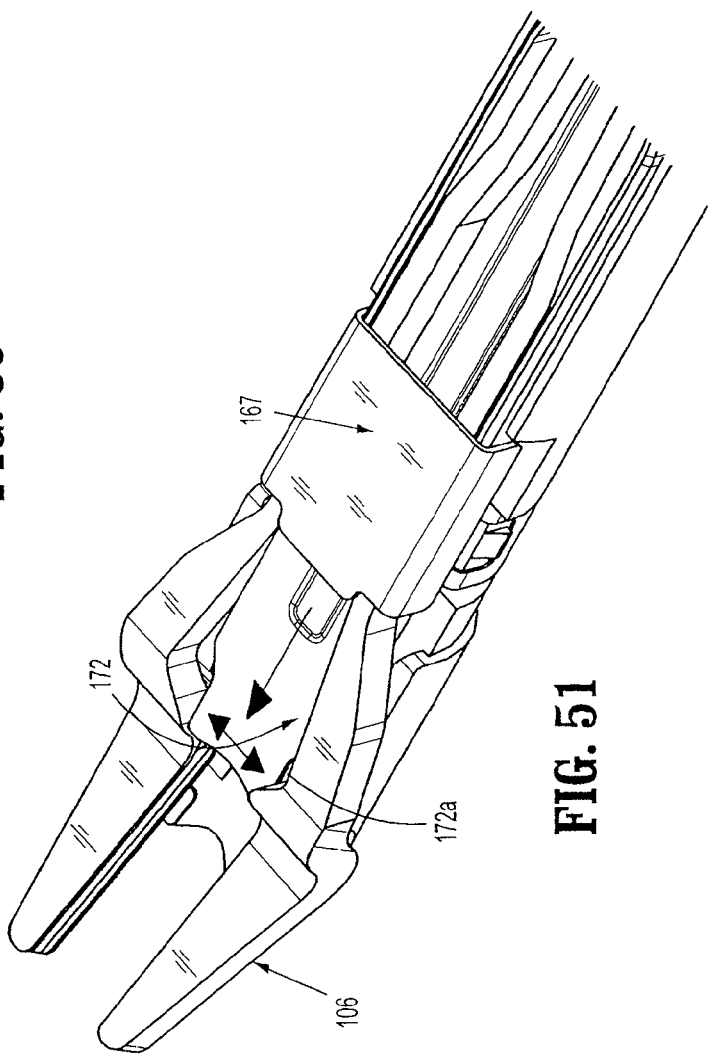
FIG. 51 is a bottom, left side perspective view of a distal end of the shaft assembly, during the initial actuation of the clip applier.

As seen in FIG. 51, as wedge plate 172 is moved in a distal direction, distal end 172a thereof enters between jaws 106 causing jaws 106 to splay outwardly.

Figure 52:
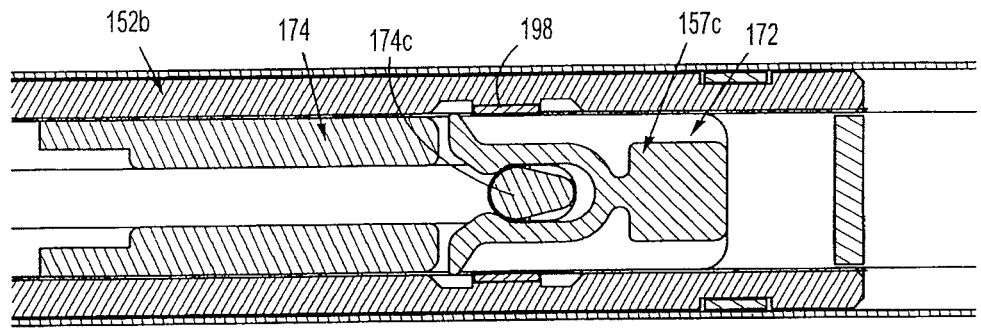
FIGS. 52-54 are each longitudinal, cross-sectional views of the shaft assembly, illustrating a further movement of the wedge plate during the initial actuation of the clip applier and a disengagement of a stem of a connector plate from a snap clip of the wedge plate.
Figure 53:
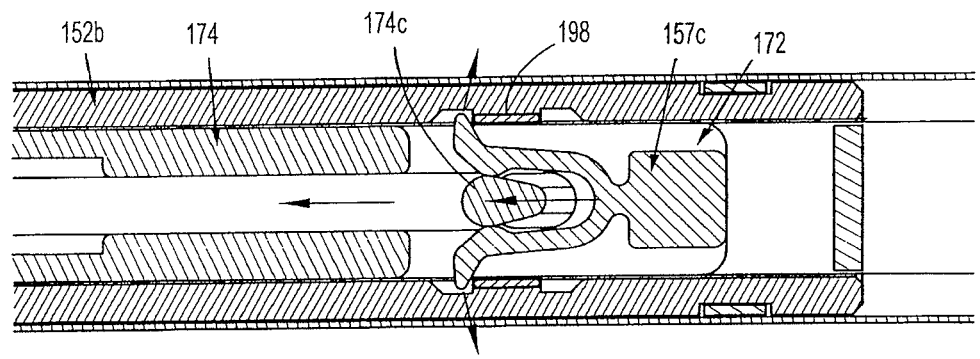
Figure 54:
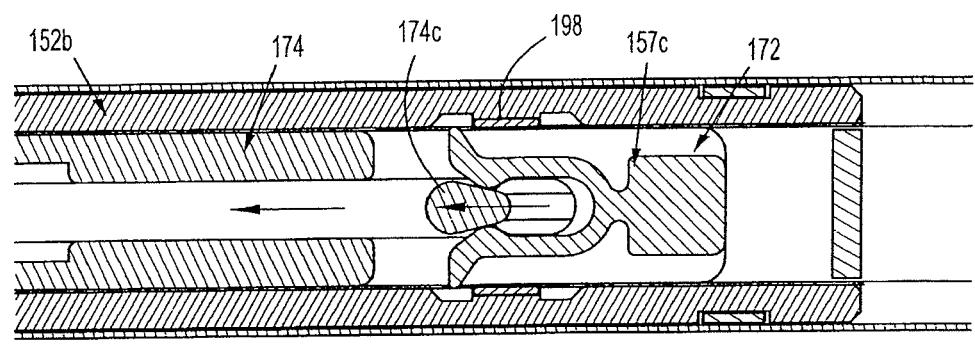

Wedge plate 172 is prevented from further movement in the distal direction, as seen in FIGS. 52-54, once wedge plate lock 190 abuts against the physical stop formed in lower housing 152b. However, drive bar 140 continues to move connector plate 174 in a distal direction. Since connector plate 174 is continued to be forced distally, once the tips of the tines of third snap clip 157c move distally beyond guard 198, the forces acting on second stem 174c are sufficient to cause the tines of third snap clip 157c to splay outward and allow second stem 174c to snap out from therebetween thereby allowing for connector plate 174 to continue to move in a distal direction.

Turning now to FIGS. 55-69, as trigger 108 is further squeezed or actuated from the first stage of the initial stroke through a second stage of the initial stroke, trigger 108 causes wishbone link 122 to further move crank plate 124 in a distal direction which, in turn, causes drive connector 134 and subsequently plunger 135 to further move distally and to further move drive bar 140 distally. As plunger 135 is moved distally, spring 136 is compressed a further amount.

Simultaneously therewith, as crank plate 124 is moved distally the teeth of rack 124a thereof move further proximally with respect to tooth 224a of pawl 224. As such, crank plate 124 still can not return to a proximal-most position without completing a full distal stroke.

As seen in FIG. 55, as crank plate 124 is moved distally, after a predetermine distance, arm 124d thereof engages or contacts finger 128b of actuator plate 128. As crank plate 124 is further advanced distally, crank plate 124 forces or pulls actuator plate 128 in a distal direction thereby actuating counter actuation lever 130 to activate counter mechanism 132.

In particular, when actuator plate 128 is moved distally a sufficient distance, second arm 130b of counter actuation lever 130 is cammed within slot 128b thereof and is urged to rotate resulting in first arm 130a of counter actuation lever 130 engaging counter mechanism 132 and thereby effectuating a change in the display thereof. In particular, the display, which displays the number of clips remaining in surgical clip applier 100, will reduce by one. Alternatively, the clip counter mechanism will increment by one or produce some other change.

As trigger 108 is squeezed further, arm 127 continues to translate through race 126a of feedback member 126. At this point in the squeezing of trigger 108, a surgical clip is loaded into the jaws 106. Accordingly, arm 127 will interact with a step 126b formed in race 126a of feedback member 126 and create an audible/tactile indication advising the user that a clip has been loaded into the jaws.

As seen in FIG. 57, as drive bar 140 is moved further in a distal direction, drive bar 140 continues to push connector plate 174 in a distal direction. Since pusher bar 156 is still selectively connected to connector plate 174 via second snap clip 157b, pusher bar 156 is further advanced or dragged in the distal direction. However, since third snap clip 157c of wedge plate 172 is disconnected from second stem 174c of connector plate 174, wedge plate 172 is not further advanced or dragged in the distal direction.

Figure 56A:
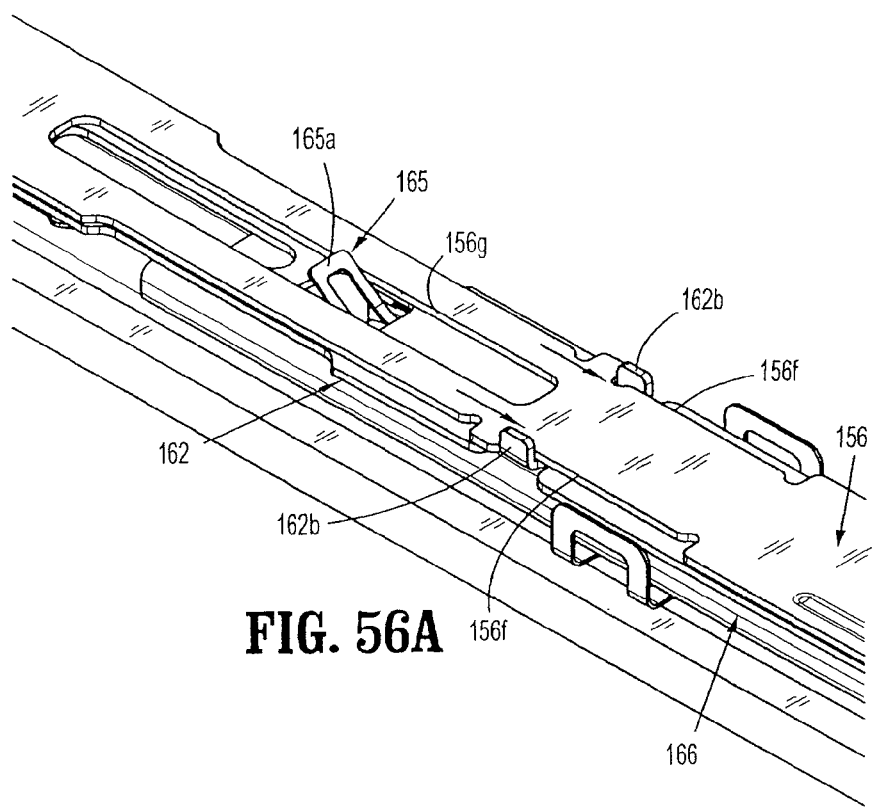
FIG. 56A is a right side, perspective view of the shaft assembly, with the upper housing removed, illustrating a movement of the pusher bar during the further actuation of the clip applier.
Figure 56B:
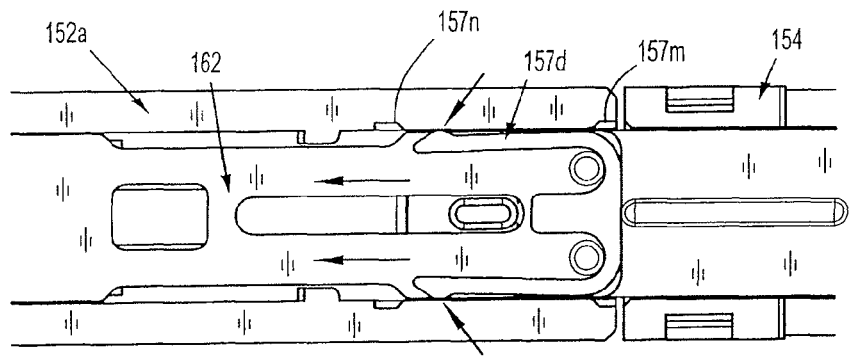
FIGS. 56B and 56C are each bottom plan views of the advancer plate illustrating a movement of the advancer plate during the further actuation of the clip applier.
Figure 56C:
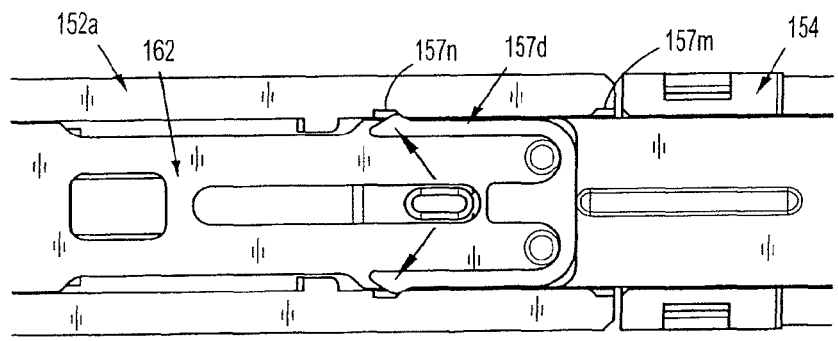

As seen in FIGS. 56A to 56C, as pusher bar 156 is continued to be moved in a distal direction, with the pair of fins 162b of advancer plate 162 engaged by the proximal end of side recesses 156f of pusher bar 156, pusher bar 156 advances or drags advancer plate 162 in a distal direction.

As seen in FIGS. 56B and 56C, as advancer plate 162 is advanced distally, snap clip 157d disengages proximal retaining grooves 152m and engages distal retaining grooves 152n formed in upper housing 152a.

As seen in FIG. 57, drive bar 140 is moved in the distal direction until tab 182a of slider joint 182 is relatively translated to a proximal-most position in elongate slot 140a of drive bar 140.

As pusher bar 156 continues to move in a distal direction, pusher bar 156 continues to urge advancer plate 162 in a distal direction via fins 162b. As seen in FIG. 58, as advancer plate 162 is moved in a distal direction, distal tab 166b of clip follower 166 is engaged by a proximal edge of a window 162a receiving distal tab 166b of clip follower 166 in order to urge clip follower 166 in a distal direction, relative to clip carrier 164, and thereby advance the stack of clips "C" by an incremental amount. As clip follower 166 is moved in a distal direction, proximal tab 166c thereof is caused to be advanced distally, one window 164a, from a relatively proximal window 164a of clip carrier 164 to a relatively distal window 164a of clip carrier 164.

As seen in FIGS. 58-60, as pusher bar 156 is moved in a distal direction, first snap clip 157a, supported on pusher bar 156, snaps onto boss 152h of upper housing 152a, thus maintaining pusher bar 156 in a forward position.

Additionally, as seen in FIG. 61, as pusher bar 156 continues to move in a distal direction, the stack of clips "C" is caused to move in a distal direction.

As seen in FIG. 62, as pusher bar 156 is moved in a distal direction pusher 156c thereof continues to move a distal-most clip "C1" in a distal direction until distal-most clip "C1" completely enters into channels 106a of jaws 106. In operation, pusher 156c of pusher bar 156 remains in contact with the backspan of the loaded clip "C" during the formation of said clip "C" in order to provide stability thereto and to maintain the proper position thereof.

Figure 63:
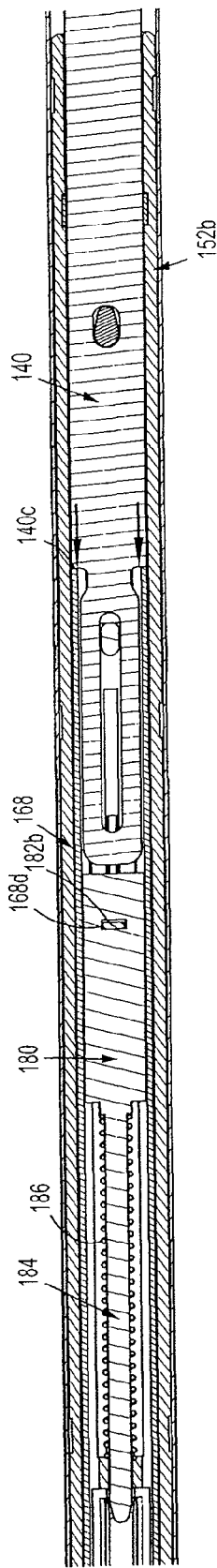
FIG. 63 is a longitudinal cross-sectional view of the shaft assembly illustrating a movement of the drive bar during a further actuation of the clip applier.

As seen in FIG. 63, as drive bar 140 is moved further in the distal direction, shoulders 140c thereof contact a proximal-most end of drive channel 168. In this manner, as drive bar 140 is moved further in the distal direction, drive bar 140 moves or urges drive channel 168 in the distal direction.

Figure 64:
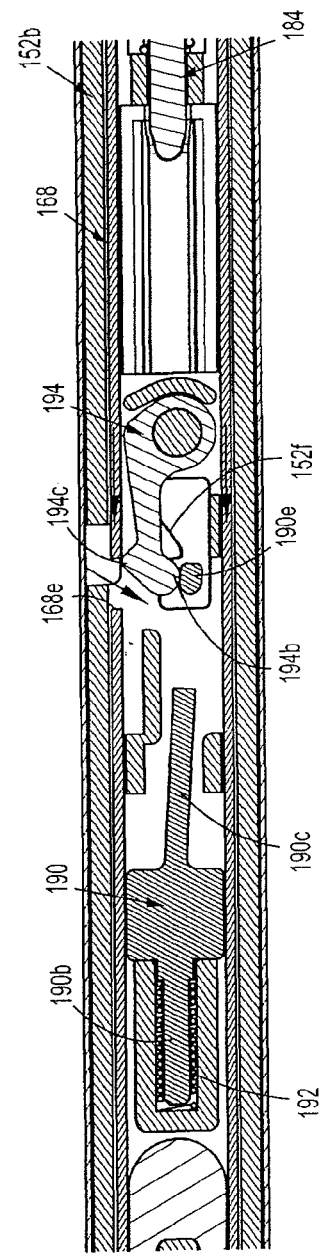
FIGS. 64 and 65 are enlarged views of the cross-section taken through 41-41 of FIG. 40 of the shaft assembly, during the further actuation of the clip applier.
Figure 65:
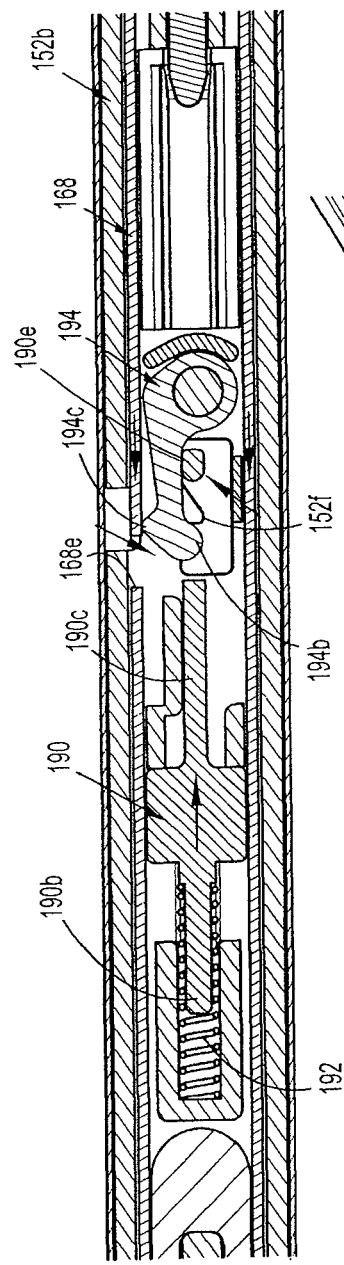
Figure 66:
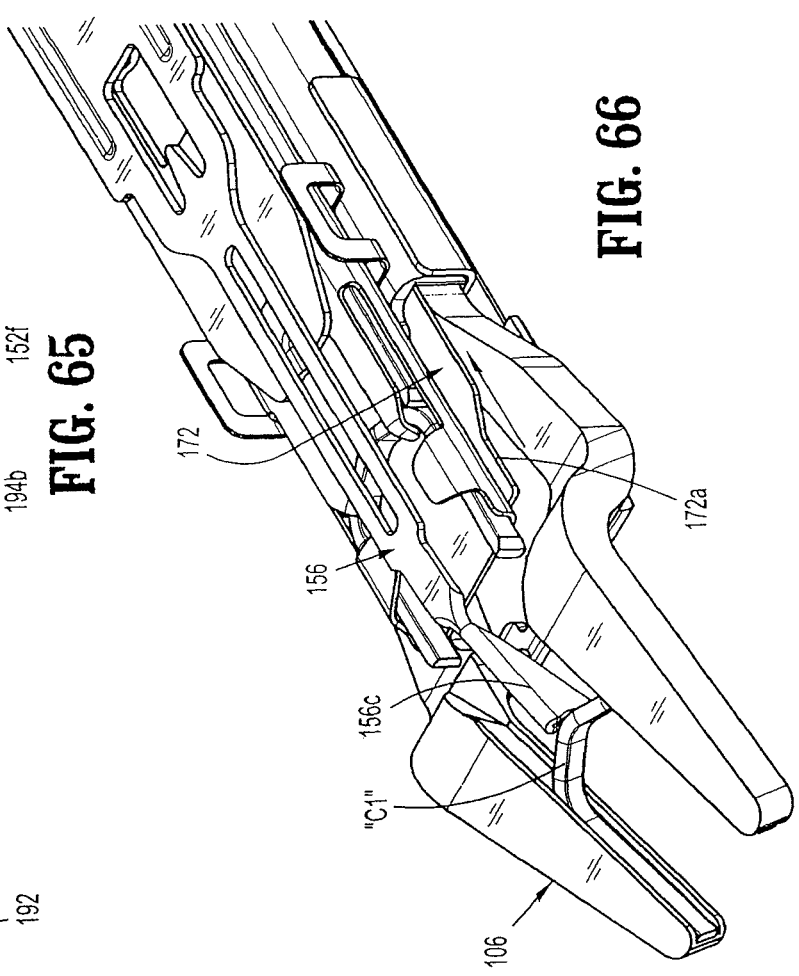
FIG. 66 is a top, left side perspective view of a distal end of the shaft assembly, during the further actuation of the clip applier.

As seen in FIG. 64, as drive channel 168 is moved in a distal direction, a proximal edge of window 168e formed in side wall 168b of drive channel 168 contacts against tooth 194c of wedge plate release 194 causing wedge plate release 194 to rotate. As wedge plate release 194 rotates, hammer 194b thereof, presses against tooth 190e of wedge plate lock 190 to urge or kick tooth 190e out from behind ramped ledge 152f. In so doing, as seen in FIG. 65, biasing member 192 is permitted to decompress thus moving wedge plate lock 190 in a proximal direction. As seen in FIG. 66, as wedge plate lock 190 is moved in a proximal direction, and since wedge plate 172 is connected thereto, wedge plate 172 is moved in a proximal direction to withdraw distal end 172a thereof out of engagement from jaws 106.

As seen in FIGS. 58 and 67-69, since pusher bar 156 is maintained in the distal position by the connection of first snap clip 157a with boss 152h, as drive bar 140 is moved further in a distal direction, the forces acting on connector plate 174 cause second snap clip 157b to disengage from first stem 174b of connector plate 174 thereby allowing for connector plate 174 to continue to move in a distal direction.

As seen in FIGS. 67A-69A, in an embodiment, the tips of the tines of second snap clip 157b may be configured to project outwardly so as to engage a surface of rear upper housing 154 (see FIG. 9), thereby preventing premature disengagement of second snap clip 157b from first stem 174b of connector plate 174. In this embodiment, recesses may be formed in the surfaces of rear upper housing 154 coinciding with locations at which the tines of second snap clip 157b may splay outward thus allowing first stem 174b of connector plate 174 to disengage an to continue to move in a distal direction.

As seen in FIGS. 70-75, as trigger 108 is actuated through a final stage of the initial stroke, trigger 108 causes wishbone link 122 to further move crank plate 124 in a distal direction which, in turn, causes drive connector 134 and plunger 135 to further move distally and to further move drive bar 140 distally. As drive connector 134 is moved distally, spring 136 is compressed a further amount.

Simultaneously therewith, as crank plate 124 is moved distally the teeth of rack 124a thereof move further proximally with respect to tooth 224a of pawl 224 to a position where the teeth of rack 124a disengage from tooth 224a of pawl 224 as tooth 224a of pawl 224 enters proximal recess 124c of crank plate 124 and thus resets itself. As such, crank plate 124 may return to a proximal-most position upon a release of trigger 108.

As seen in FIGS. 72-74, during the final stage of the initial stroke of trigger 108, drive channel 168 and strap 167 are moved in a distal direction relative to jaws 106 such that a distal edge of drive channel 168 engages against camming surfaces 106b of jaws 106 causing jaws 106 to close and form the clip "C1" positioned therebetween. As seen in FIG. 74, pusher 156c of pusher bar 156 remains at a distal position, in contact with a backspan of said clip "C" during the formation thereof.

As seen in FIG. 55, as trigger 108 is squeezed a final amount, arm 127 continues to translate through race 126a of feedback member 126. At this point in the squeezing of trigger 108, surgical clip "C1" has been fully formed by jaws 106. Accordingly, arm 127 will interact with another step 126b formed in race 126a of feedback member 126 and create an audible/tactile indication advising the user that surgical clip "C1" has been formed by jaws 106.

Figure 75:
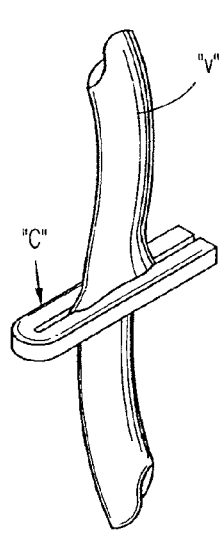
FIG. 75 is a perspective view illustrating a surgical clip applied to a vessel.

As seen in FIG. 75, surgical clip "C1" may be formed or crimped onto a vessel "V" or any other biological tissue.

Figure 76:
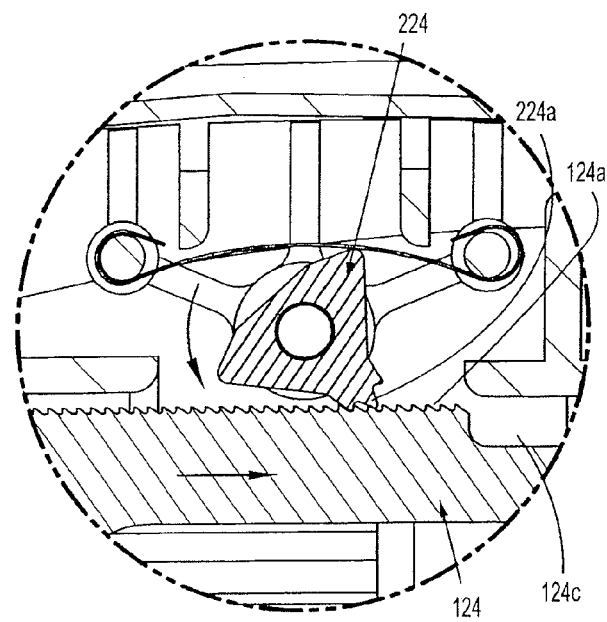
FIG. 76 is an enlarged view of the indicated area of detail 71 of FIG. 70, during a release of the trigger of the clip applier.

Turning now to FIGS. 76-84, the operation of clip applier 100 as trigger 108 is returned to an un-squeezed or unactuated position, is shown. As seen in FIG. 76, as the trigger is returned to the un-squeezed position, the spring is permitted to uncompress, thus urging crank plate 124 to move in a proximal direction which, in turn, causes the plunger to move proximally and to move the drive bar proximally. Since pawl 224 has been reset, crank plate 124 is now permitted to move proximally until tooth 224a of pawl 224 re-enters the distal recess of crank plate 124.

Figure 76A:
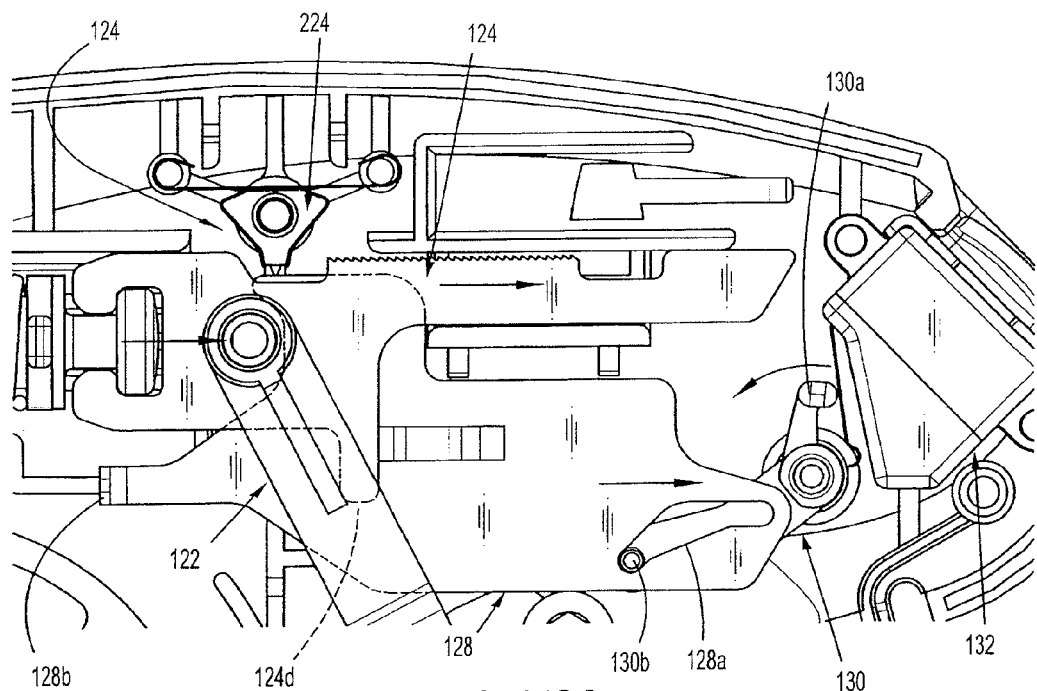
FIG. 76A is a side, elevational view of the handle assembly during a release of the trigger following a full actuation thereof.

As seen in FIG. 76A, as crank plate 124 is moved proximally, arm 124d thereof disengages finger 128b of actuator plate 128 allowing actuator plate 128 to move in a proximal direction. As actuator plate 128 is moved proximally, second arm 130b of counter actuation lever 130 is cammed within slot 128b thereof and is urged to rotate resulting in first arm 130a of counter actuation lever 130 disengaging from counter mechanism 132.

Figure 77:
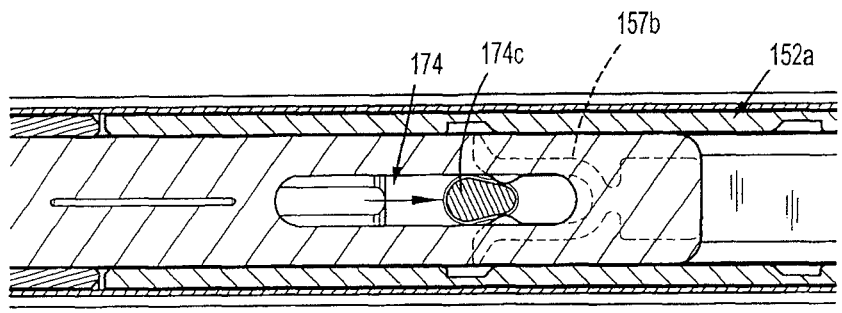
FIG. 77 is a longitudinal cross-sectional view of the shaft assembly illustrating a movement of the connector plate during the release of the trigger.

As seen in FIG. 77, as drive bar 140 is moved in a proximal direction, drive bar 140 pulls on connector plate 174, via first stem 174b. As connector plate 174 is moved in a proximal direction, first stem 174b engages the tines of second snap clip 157b and urges pusher bar 156 in a proximal direction via second snap clip 157b.

Figure 78:
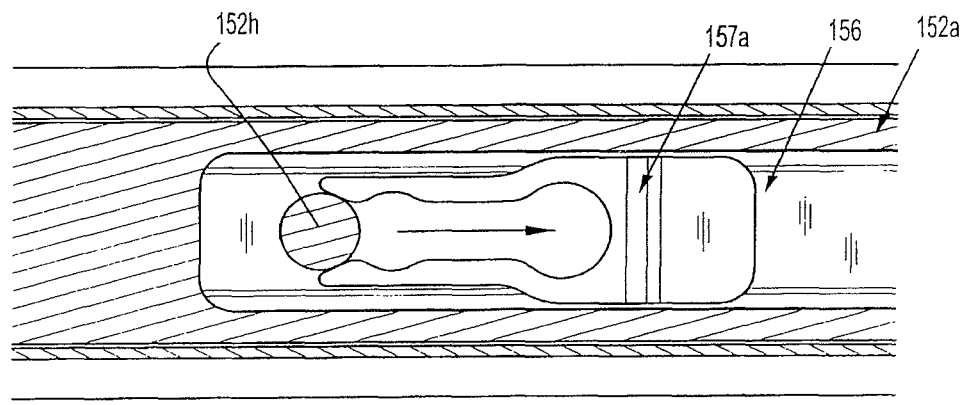
FIG. 78 is a longitudinal, cross-sectional view of the shaft assembly illustrating a movement of the pusher bar during the release of the trigger, and a disconnection of the clip supported thereon from the boss of the upper housing.

As seen in FIG. 78, as forces act on pusher bar 156 to move pusher bar 156 in a proximal direction, said forces overcome the retention force of first snap clip 157a with boss 152h of upper housing 152a, thus releasing first snap clip 157a from boss 152h and allowing pusher bar 156 to move in the proximal direction.

Figure 79:
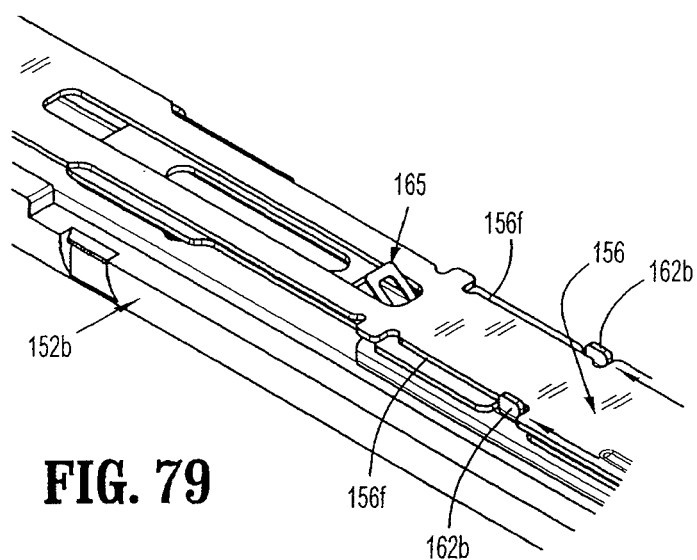
FIG. 79 is a right side, perspective view of the shaft assembly, with the upper housing removed, illustrating a movement of the pusher bar during the release of the trigger.

As seen in FIG. 79, as pusher bar 156 continues to move in the proximal direction, a distal end of side recesses 156f thereof engage fins 162b of advancer plate 162 and cause advancer plate 162 to move in a proximal direction. As pusher bar 156 moves in the proximal direction, pusher bar nose 156c snaps behind a distal-most clip of the remaining stack of clips "C" and thus becomes the new distal-most clip "C1."

Figure 80:
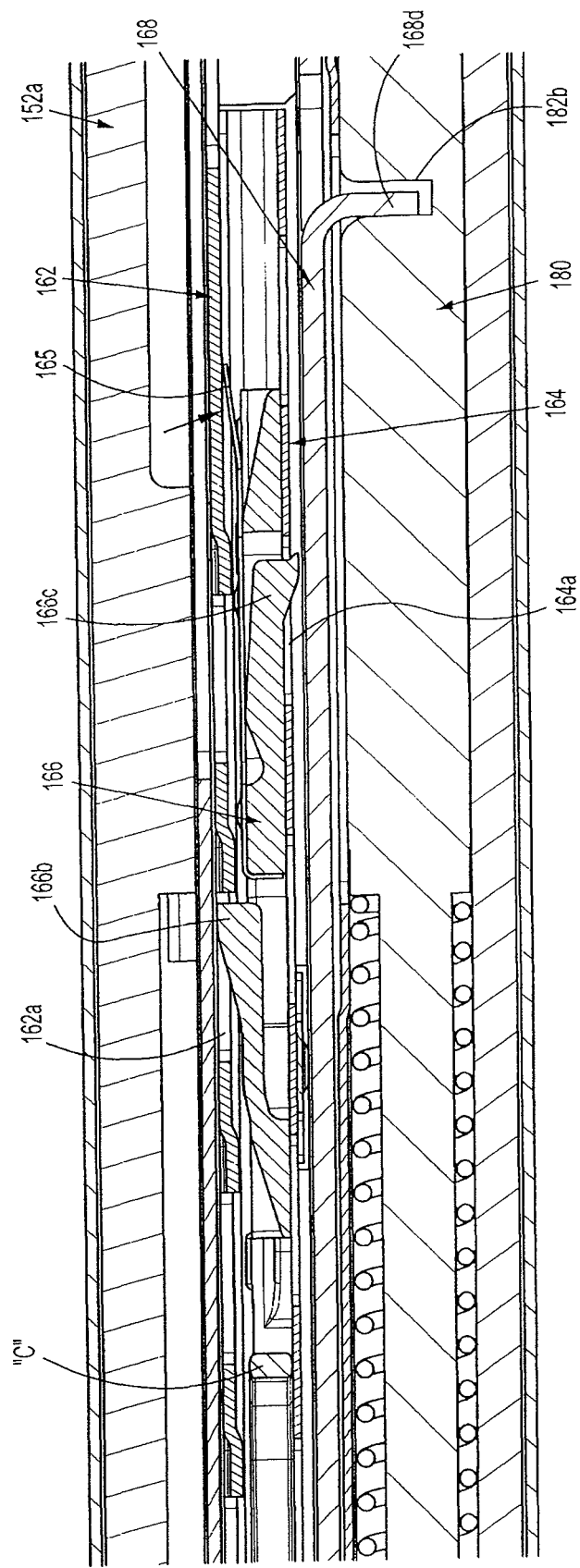
FIG. 80 is an enlarged view of the indicated area of detail 40 of FIG. 34, during the release of the trigger.

As seen in FIG. 80, as advancer plate 162 is moved in a proximal direction, proximal tab 166c of clip follower 166 engages a proximal edge of a window 164a of clip carrier 164 in order to maintain the relative position of clip follower 166 in clip carrier 164. As advancer plate 162 is moved in a proximal direction, distal tab 166b thereof is caused to be advanced distally, one window 162a, from a relatively proximal window 162a of advancer plate 162 to a relatively distal window 162a of advancer plate 162.

Figure 81:
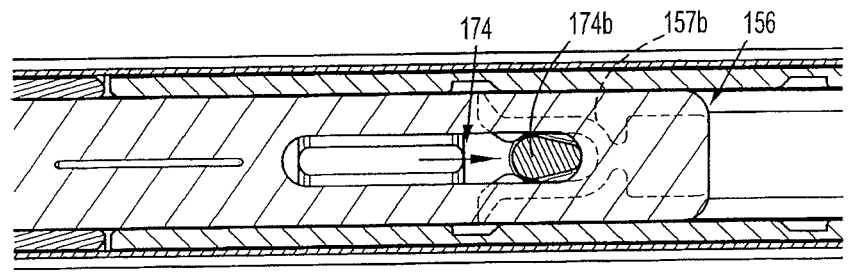
FIG. 81 is a longitudinal cross-sectional view of the shaft assembly illustrating a reconnection of a stem of the connector plate to a snap clip of the pusher bar, during the release of the trigger.

As seen in FIG. 81, when pusher bar 156 stops its proximal movement, upon engagement thereof with a boss protruding from an inner surface of upper housing half 152a, continued proximal movement of connector plate 174 will cause first stem 174b to re-engage with second snap clip 157b. With proximal movement of pusher bar 156 stopped, continued proximal movement of connector plate 174 will cause first stem 174b to re-engage with second snap clip 157b.

Figure 82:
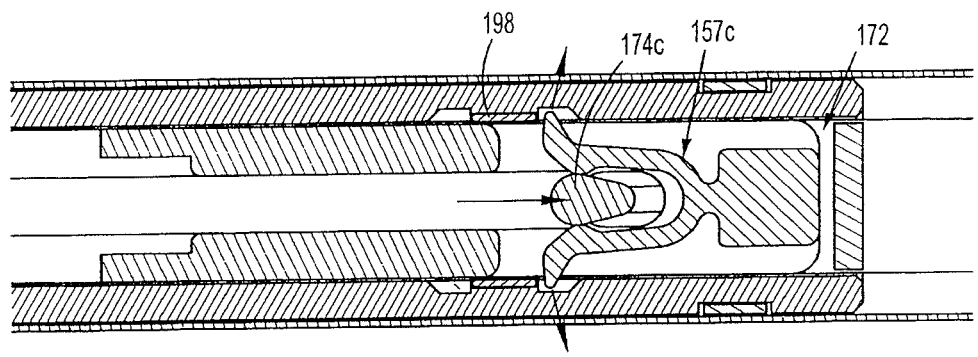
FIGS. 82 and 83 are each longitudinal, cross-sectional views of the shaft assembly, illustrating a movement of the wedge plate during the release of the trigger and a reengagement of the stem of the connector plate to a snap clip of the wedge plate.
Figure 83:
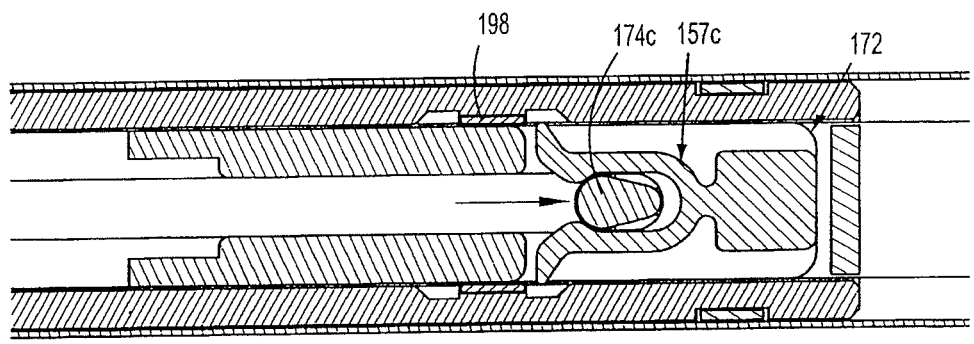

As seen in FIGS. 82 and 83, as connector plate 174 is moved in a proximal direction, as a result of the proximal movement of drive bar 140, second stem 174c engages the tines of third snap clip 157c and urges wedge plate 172 in a proximal direction via third snap clip 157c. As wedge plate 172 is moved in a proximal direction, wedge plate lock 190 is moved in a proximal direction until wedge plate lock 190 contacts a physical stop in lower housing half 152b, thereby stopping proximal movement of wedge plate 172. Once the tips of the tines of third snap clip 157c move proximally past guard 198, when wedge plate 172 stops its proximal movement, continued proximal movement of connector plate 174 will cause second first stem 174c to re-engage with third snap clip 157c.

When trigger 108 is returned to the unactuated position, arm 127 will translate through race 126a of feedback member 126 and interact with another step 126b formed in race 126a of feedback member 126 and create an audible/tactile indication advising the user that surgical clip applier 100 has been reset and is ready to fire again.

Turning now to FIGS. 84-85, the configuration of surgical clip applier 100, following application of the last surgical clip "C", is shown. As seen in FIGS. 84 and 85, when the last surgical clip has been advanced and formed, with pusher bar 156 still in an advanced or distal position, clip follower 166 has been incrementally advanced, by indexer plate 158, an amount sufficient that lock-out plate 165 thereof biases upwardly through a window 162a of advancer plate 162 and into distal window 156d of pusher bar 156. Positioning of lock-out plate 165 in distal window 156d of pusher bar 156 allows for the catch 156e thereof to enter and engage in window 165b of lock-out plate 165. In this manner, since clip follower 166 is maintained in the distal position by proximal tab 166c thereof engaging in distal window 164a of clip carrier 164, lock-out plate 165 engages catch 156e of pusher bar 156 and prevents pusher bar 156 from returning to a proximal-most position to reset pawl 224.

Since pusher bar 156 can not or is prevented from moving to its fully proximal position, as seen in FIG. 86, pawl 224 remains engaged with rack 124a of crank plate 124 and is not permitted to enter proximal recess 124c and thus reset itself. Since pawl 224 can not reset itself, crank plate 124 is locked or stopped from distal or proximal movement.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An apparatus for application of surgical clips to body tissue, the apparatus comprising:
   a handle assembly including a trigger and a drive bar reciprocally translatable by the trigger upon an actuation thereof;
   a shaft assembly extending distally from the handle assembly and defining a longitudinal axis, the shaft assembly including:
   a housing;
   a plurality of surgical clips disposed within the housing;
   a jaw mounted adjacent a distal end portion of the housing, the jaw being movable between an open spaced-apart condition and a closed approximated condition;
   a pusher bar disposed within the housing for reciprocal movement between a proximal position and a distal position defining a stroke having a length, the pusher bar being configured to load a distal-most surgical clip into the jaws upon a movement from the proximal position to the distal position;
   an advancer plate disposed within the housing for reciprocal movement between a proximal position and a distal position, wherein the advancer plate is engaged by the pusher bar during a distal and a proximal movement of the pusher bar to effectuate one of a distal and proximal movement of the advancer plate, wherein the advancer plate moves a distance less than the length of the stroke; and a snap clip supported on the advancer plate and detachably engagable to the housing to releasably maintain the advancer plate in one of the proximal position and the distal position.

2. The apparatus according to claim 1, further comprising:
a wedge plate reciprocally disposed within the housing, the wedge plate being movable between a position where a distal end thereof is disposed in the jaws and a position where the distal end thereof is free from said jaws; and
a connector plate reciprocally disposed within the housing, wherein the connector plate detachably connects to at least one of the pusher bar and the wedge plate during at least a portion of a firing stroke of the apparatus.

3. The apparatus according to claim 2, wherein the connector plate detachably connects to each of the pusher bar and the wedge plate during at least a portion of the firing stoke of the apparatus.

4. The apparatus according to claim 2, wherein the pusher bar includes a spring clip supported thereon for detachably connecting to a first feature provided on the connector plate, and the wedge plate includes a spring clip supported thereon for detachably connecting to a second feature provided on the connector plate.

5. The apparatus according to claim 4, wherein the spring clip of the pusher bar is connected to the first feature of the connector plate during an initial distal movement of the connector plate to pull the pusher bar in a distal direction.

6. The apparatus according to claim 4, wherein the housing includes a stationary feature blocking distal movement of the pusher bar beyond the initial distal movement, and wherein the first feature of the connector plate disconnects from the spring clip of the pusher bar upon continued distal movement beyond the initial distal movement.

7. The apparatus according to claim 6, wherein the pusher bar includes a further spring clip supported thereon for detachably connecting to the stationary feature of the housing when the pusher bar is at a distal-most position.

8. The apparatus according to claim 7, wherein the connection of the further spring clip of the pusher bar and the stationary feature of the housing maintains the pusher bar at the distal-most position thereof during a firing of the apparatus.

9. The apparatus according to claim 4, wherein the spring clip of the wedge plate is connected to the second feature of the connector plate during an initial distal movement of the connector plate to pull the wedge plate in a distal direction such that the distal end thereof is disposed in the jaws.

10. The apparatus according to claim 9, wherein the second feature of the connector plate disconnects from the spring clip of the wedge plate following an initial distal movement of the wedge plate.

11. The apparatus according to claim 9, wherein the wedge plate is moved in a proximal direction at a time prior to an approximation of the jaws to free the jaws of the distal end of the wedge plate.

12. The apparatus according to claim 4, wherein the pusher bar and the wedge plate each disconnect from the connector plate following an initial distal movement of each of the pusher bar and the wedge plate.

13. The apparatus according to claim 12, wherein each of the pusher bar and the wedge plate re-connect with the connector plate upon a respective proximal movement thereof.

14. The apparatus according to claim 1, wherein the advancer plate is disposed adjacent to the pusher bar, the advancer plate including at least one fin engageable by a shoulder of the pusher bar, wherein the shoulder of the pusher bar engages the at least one fin of the advancer plate during a distal and a proximal movement of the pusher bar to effectuate one of a distal and proximal movement of the advancer plate.

15. The apparatus according to claim 1, wherein the shaft assembly includes a clip carrier disposed within the housing adjacent the advancer plate, wherein the clip carrier is configured to retain the plurality of surgical clips.

16. The apparatus according to claim 15, wherein the shaft assembly includes a clip follower slidably supported in the clip carrier at a location proximal of the plurality of surgical clips, the clip follower being configured to urge the plurality of surgical clips in a distal direction, the clip follower including a first tab projecting from a first surface thereof and a second tab projecting from a second surface thereof, wherein the first tab of the clip follower engages the advancer plate as the advancer plate is moved distally such that the clip follower is moved distally to advance the plurality of surgical clips, and wherein the second tab of the clip follower engages the clip follower as the advancer plate is moved proximally such that the clip follower remains stationary.

17. The apparatus according to claim 16, wherein the shaft assembly includes a drive channel reciprocally disposed within the housing adjacent the clip carrier, wherein the drive bar selectively engages the drive channel to effect translation of the drive channel, wherein a distal end of the drive channel engages a surface of the jaws upon distal advancement thereof to effectuate approximation of the jaws.

18. The apparatus according to claim 16, wherein the clip follower is incrementally advanced through the shaft assembly.

19. The apparatus according to claim 16, wherein the clip follower includes a catch extending from a surface thereof, wherein the catch engages the pusher bar following firing of a last surgical clip and prevents movement of the pusher bar in a proximal direction.

20. The apparatus according to claim 1, wherein the snap clip includes a pair of tines configured for detachable engagement with the housing.

21. The apparatus according to claim 20, wherein the housing includes a first set of opposed retaining grooves configured to detachably receive the tines of the snap clip to releasably maintain the advancer plate in the proximal position.

22. The apparatus according to claim 21, wherein the housing includes a second set of opposed retaining grooves configured to detachably receive the tines of the snap clip to releasably maintain the advancer plate in the distal position.

* * * * *